(12) United States Patent
McCall et al.

(10) Patent No.: US 11,270,792 B2
(45) Date of Patent: Mar. 8, 2022

(54) HEMODYNAMIC MONITORING SYSTEM WITH DETACHABLE DISPLAY UNIT

(71) Applicant: ICU Medical, Inc., San Clemente, CA (US)

(72) Inventors: Tom McCall, San Clemente, CA (US); David Snider, Cincinnati, OH (US); Timothy John Hughes, Palo Alto, CA (US); Lina Derderian, San Clemente, CA (US); James Cobb, Vista, CA (US); Alison D. Burcar, San Clemente, CA (US)

(73) Assignee: ICU Medical, Inc., San Clemente, CA (US)

( * ) Notice: Subject to any disclaimer, the term of this patent is extended or adjusted under 35 U.S.C. 154(b) by 822 days.

(21) Appl. No.: 15/954,218

(22) Filed: Apr. 16, 2018

(65) Prior Publication Data

US 2018/0228386 A1    Aug. 16, 2018

Related U.S. Application Data

(63) Continuation of application No. PCT/US2016/057553, filed on Oct. 18, 2016.
(Continued)

(51) Int. Cl.
*G16H 40/63* (2018.01)
*A61B 5/00* (2006.01)
(Continued)

(52) U.S. Cl.
CPC ............ *G16H 40/63* (2018.01); *A61B 5/002* (2013.01); *A61B 5/0205* (2013.01);
(Continued)

(58) Field of Classification Search
None
See application file for complete search history.

(56) References Cited

U.S. PATENT DOCUMENTS

| | | |
|---|---|---|
| 3,618,592 A | 11/1971 | Stewart |
| 3,868,679 A | 2/1975 | Arneson |

(Continued)

FOREIGN PATENT DOCUMENTS

| | | |
|---|---|---|
| JP | 62-129032 | 6/1987 |
| JP | 2011-10112 | 1/2011 |

(Continued)

OTHER PUBLICATIONS

US 8,613,701 B2, 12/2013, Rao et al. (withdrawn)
(Continued)

*Primary Examiner* — Michael R Bloch
(74) *Attorney, Agent, or Firm* — Knobbe Martens Olson & Bear LLP

(57) ABSTRACT

A patient monitor configured to receive patient-information electrical signals from an invasive patient sensor and a minimally invasive patient sensor, the patient monitor including a base unit and a detachable user interface unit for displaying hemodynamic parameters determined by the base unit. The base unit and user interface unit can be docked together, tethered together through a cabled connection, or physically separated from one another using wireless communication to transmit and receive information. The base unit and the user interface unit may pair before the user interface unit displays data to link the base unit with the user interface unit. The patient monitor can be configured to switch between invasive and minimally invasive monitoring of hemodynamic parameters of a patient, using invasive measurements to calibrate minimally invasive measurements.

10 Claims, 30 Drawing Sheets

Related U.S. Application Data

(60) Provisional application No. 62/243,555, filed on Oct. 19, 2015.

(51) Int. Cl.

| | | |
|---|---|---|
| *A61B 5/0205* | (2006.01) | |
| *G16H 50/30* | (2018.01) | |
| *G16H 50/20* | (2018.01) | |
| *G16H 40/40* | (2018.01) | |
| *A61B 5/0215* | (2006.01) | |
| *A61B 5/021* | (2006.01) | |
| *A61M 25/00* | (2006.01) | |

(52) U.S. Cl.
CPC ........ *A61B 5/0215* (2013.01); *A61B 5/02108* (2013.01); *A61B 5/02156* (2013.01); *A61B 5/7225* (2013.01); *A61B 5/7278* (2013.01); *A61B 5/7405* (2013.01); *A61B 5/746* (2013.01); *A61B 5/7435* (2013.01); *A61B 5/7445* (2013.01); *G16H 40/40* (2018.01); *G16H 50/20* (2018.01); *G16H 50/30* (2018.01); *A61B 2560/0209* (2013.01); *A61B 2560/0266* (2013.01); *A61B 2560/045* (2013.01); *A61B 2560/0456* (2013.01); *A61M 2025/0003* (2013.01)

(56) References Cited

U.S. PATENT DOCUMENTS

| | | |
|---|---|---|
| 4,465,075 A | 8/1984 | Swartz |
| 4,501,531 A | 2/1985 | Bilstad et al. |
| 4,550,611 A | 11/1985 | Czarnocki |
| 4,557,269 A | 12/1985 | Reynolds et al. |
| 4,581,940 A | 4/1986 | Merrick et al. |
| 4,611,601 A | 9/1986 | Bowman |
| 4,659,235 A | 4/1987 | Gilmore, Jr. et al. |
| 4,679,567 A | 7/1987 | Hanlon et al. |
| 4,683,894 A | 8/1987 | Kodama et al. |
| 4,685,469 A | 8/1987 | Keller |
| 4,817,022 A | 3/1989 | Jomod et al. |
| 4,825,876 A | 5/1989 | Beard |
| 4,883,992 A | 11/1989 | Koglin et al. |
| 4,926,674 A | 5/1990 | Fossum et al. |
| 4,950,235 A | 8/1990 | Slate et al. |
| 5,135,002 A | 8/1992 | Kirchner et al. |
| 5,269,311 A | 12/1993 | Kirchner et al. |
| 5,400,793 A | 3/1995 | Wesseling |
| 5,526,817 A | 6/1996 | Pfeiffer et al. |
| 5,579,771 A | 12/1996 | Bonnefous |
| 5,623,925 A | 4/1997 | Swenson et al. |
| 5,640,953 A | 6/1997 | Bishop et al. |
| 5,685,314 A | 11/1997 | Geheb et al. |
| 5,712,795 A | 1/1998 | Layman et al. |
| 5,713,856 A | 2/1998 | Eggers et al. |
| 5,746,698 A | 5/1998 | Bos et al. |
| 5,781,442 A | 7/1998 | Engleson et al. |
| 5,800,387 A | 9/1998 | Duffy et al. |
| 5,803,917 A | 9/1998 | Butterfield et al. |
| 5,822,185 A | 10/1998 | Cavello |
| 5,827,223 A | 10/1998 | Butterfield et al. |
| 5,836,910 A | 11/1998 | Duffy et al. |
| 5,848,988 A | 12/1998 | Davis |
| 5,904,708 A | 5/1999 | Goedeke |
| 5,908,027 A | 6/1999 | Butterfield et al. |
| 5,941,846 A | 8/1999 | Duffy et al. |
| 5,954,641 A | 9/1999 | Kehr et al. |
| 5,957,885 A | 9/1999 | Bollish et al. |
| 5,961,487 A | 10/1999 | Davis |
| 6,045,512 A | 4/2000 | Roteliuk et al. |
| 6,050,951 A | 4/2000 | Friedman et al. |
| 6,071,244 A | 6/2000 | Band et al. |
| 6,085,752 A | 7/2000 | Kehr et al. |
| 6,102,855 A | 8/2000 | Kehr et al. |
| 6,113,543 A | 9/2000 | Bonnefous |
| 6,158,965 A | 12/2000 | Butterfield et al. |
| 6,159,151 A | 12/2000 | Bonnefous |
| 6,181,549 B1 | 1/2001 | Mills et al. |
| 6,183,417 B1 | 2/2001 | Geheb et al. |
| 6,185,095 B1 | 2/2001 | Helot et al. |
| 6,200,301 B1 | 3/2001 | Pfeiffer et al. |
| 6,213,972 B1 | 4/2001 | Butterfield et al. |
| 6,224,585 B1 | 5/2001 | Pfeiffer |
| 6,231,498 B1 | 5/2001 | Pfeiffer et al. |
| 6,270,252 B1 | 8/2001 | Siefert |
| 6,290,650 B1 | 9/2001 | Butterfield et al. |
| 6,315,735 B1 | 11/2001 | Joeken et al. |
| 6,348,777 B1 | 2/2002 | Brown et al. |
| 6,358,213 B1 | 3/2002 | Friedman et al. |
| 6,358,225 B1 | 3/2002 | Butterfield |
| 6,394,961 B1 | 5/2002 | Pfeiffer et al. |
| 6,416,291 B1 | 7/2002 | Butterfield et al. |
| 6,485,431 B1 | 11/2002 | Campbell |
| 6,485,481 B1 | 11/2002 | Pfeiffer |
| 6,506,163 B1 | 1/2003 | Farrell et al. |
| 6,532,381 B2 | 3/2003 | Bayer et al. |
| 6,537,214 B1 | 3/2003 | Hood et al. |
| 6,562,012 B1 | 5/2003 | Brown et al. |
| 6,570,758 B1 | 5/2003 | Maeda |
| 6,575,901 B2 | 6/2003 | Stoycos et al. |
| 6,582,370 B2 | 6/2003 | Jibiki |
| 6,583,985 B2 | 6/2003 | Nguyen et al. |
| 6,584,336 B1 | 6/2003 | Ali et al. |
| 6,589,264 B1 | 7/2003 | Barbut et al. |
| 6,591,135 B2 | 7/2003 | Palmer et al. |
| 6,592,546 B1 | 7/2003 | Barbut |
| 6,594,146 B2 | 7/2003 | Frangesch et al. |
| 6,602,191 B2 | 8/2003 | Quy |
| 6,609,023 B1 | 8/2003 | Fischell et al. |
| 6,611,206 B2 | 8/2003 | Eshelman et al. |
| 6,645,177 B1 | 11/2003 | Shearn |
| 6,648,828 B2 | 11/2003 | Friedman et al. |
| 6,671,547 B2 | 12/2003 | Lyster et al. |
| 6,671,563 B1 | 12/2003 | Engelson et al. |
| 6,673,018 B2 | 1/2004 | Friedman |
| 6,698,921 B2 | 3/2004 | Siefert |
| 6,699,203 B2 | 3/2004 | Starr et al. |
| 6,705,992 B2 | 3/2004 | Gatzke |
| 6,731,973 B2 | 5/2004 | Voith |
| 6,731,989 B2 | 5/2004 | Engleson et al. |
| 6,736,782 B2 | 5/2004 | Pfeiffer et al. |
| 6,746,431 B2 | 6/2004 | Pfeiffer et al. |
| 6,758,822 B2 | 7/2004 | Romano |
| 6,801,802 B2 | 10/2004 | Sitzman et al. |
| 6,829,501 B2 | 12/2004 | Nielsen et al. |
| 6,840,904 B2 | 1/2005 | Goldberg |
| 6,862,472 B2 | 3/2005 | Mikula et al. |
| 6,870,475 B2 | 3/2005 | Fitch et al. |
| 6,904,306 B1 | 6/2005 | Wu et al. |
| 6,915,170 B2 | 7/2005 | Engleson et al. |
| 6,997,877 B2 | 2/2006 | Band et al. |
| 7,011,672 B2 | 3/2006 | Barbut et al. |
| 7,022,322 B2 | 4/2006 | Koll et al. |
| 7,054,679 B2 | 5/2006 | Hirsh |
| 7,074,205 B1 | 7/2006 | Duffy et al. |
| 7,092,751 B2 | 8/2006 | Erkkila |
| 7,209,780 B2 | 4/2007 | Pfeiffer et al. |
| 7,220,230 B2 | 5/2007 | Roteliuk et al. |
| D552,741 S | 10/2007 | Zhou et al. |
| 7,280,864 B2 | 10/2007 | Jenkins |
| 7,297,129 B2 | 11/2007 | Kinouchi et al. |
| 7,298,613 B2 | 11/2007 | Yin et al. |
| 7,306,575 B2 | 12/2007 | Barbut et al. |
| 7,314,449 B2 | 1/2008 | Pfeiffer et al. |
| 7,319,894 B2 | 1/2008 | Higgins |
| 7,344,551 B2 | 3/2008 | Barbut et al. |
| 7,384,410 B2 | 6/2008 | Eggers et al. |
| 7,390,302 B2 | 6/2008 | Friedman et al. |
| 7,407,486 B2 | 8/2008 | Huiku et al. |
| 7,422,562 B2 | 9/2008 | Hatib et al. |
| 7,452,333 B2 | 11/2008 | Roteliuk |
| 7,465,273 B2 | 12/2008 | Friedman |
| 7,468,035 B2 | 12/2008 | Bonan et al. |

(56) References Cited

U.S. PATENT DOCUMENTS

| | | | |
|---|---|---|---|
| 7,468,038 B2 | 12/2008 | Ye et al. |
| 7,507,208 B2 | 3/2009 | Bennett et al. |
| 7,542,795 B2 | 6/2009 | Brodnick |
| 7,553,291 B2 | 6/2009 | Duffy et al. |
| 7,559,896 B2 | 7/2009 | Torp |
| 7,569,015 B2 | 8/2009 | Donaldson et al. |
| 7,572,223 B2 | 8/2009 | Donaldson |
| 7,572,230 B2 | 8/2009 | Neumann et al. |
| 7,588,542 B2 | 9/2009 | Pfeiffer et al. |
| 7,590,449 B2 | 9/2009 | Mann et al. |
| 7,594,892 B2 | 9/2009 | Cen et al. |
| 7,604,602 B2 | 10/2009 | Roteliuk et al. |
| 7,608,060 B2 | 10/2009 | Gillepsie, Jr. et al. |
| 7,611,467 B2 | 11/2009 | Zhang |
| 7,650,291 B2 | 1/2010 | Rosenfeld et al. |
| 7,651,466 B2 | 1/2010 | Hatib et al. |
| 7,666,151 B2 | 2/2010 | Sullivan et al. |
| 7,678,059 B2 | 3/2010 | Friedman et al. |
| 7,695,512 B2 | 4/2010 | Lashinski et al. |
| 7,698,156 B2 | 4/2010 | Martucci et al. |
| 7,704,209 B2 | 4/2010 | Bennett et al. |
| 7,766,863 B2 | 8/2010 | Giiiepsie, Jr. et al. |
| 7,775,987 B2 | 8/2010 | Hersh et al. |
| 7,783,339 B2 | 8/2010 | Lee et al. |
| 7,785,263 B2 | 8/2010 | Roteliuk et al. |
| 7,803,122 B2 | 9/2010 | Pfeiffer et al. |
| 7,805,181 B2 | 9/2010 | Breeuwer |
| 7,815,576 B2 | 10/2010 | Wellnhofer |
| 7,815,578 B2 | 10/2010 | Cohen et al. |
| 7,837,628 B2 | 11/2010 | Secora et al. |
| 7,850,617 B2 | 12/2010 | Goedje et al. |
| 7,873,416 B2 | 1/2011 | Guo et al. |
| D632,698 S | 2/2011 | Judy et al. |
| D632,699 S | 2/2011 | Judy et al. |
| 7,927,269 B2 | 4/2011 | Ten Eyck et al. |
| 7,935,062 B2 | 5/2011 | Karamanoglu et al. |
| 7,966,678 B2 | 6/2011 | Ten Eyck et al. |
| 7,967,749 B2 | 6/2011 | Hutchinson et al. |
| 7,967,757 B2 | 6/2011 | Roteliuk |
| 7,979,111 B2 | 7/2011 | Acquista |
| 7,991,625 B2 | 8/2011 | Rosenfeld et al. |
| 7,993,274 B2 | 8/2011 | Pruvot et al. |
| 8,000,937 B2 | 8/2011 | Zeng et al. |
| 8,016,766 B2 | 9/2011 | Goedje et al. |
| 8,025,674 B2 | 9/2011 | Barbut et al. |
| RE42,803 E | 10/2011 | Lipson et al. |
| D649,556 S | 11/2011 | Judy et al. |
| 8,047,489 B2 | 11/2011 | Watanabe |
| 8,050,748 B2 | 11/2011 | Ali et al. |
| 8,060,203 B2 | 11/2011 | Järverud et al. |
| 8,070,677 B2 | 12/2011 | Ali |
| D652,051 S | 1/2012 | Judy et al. |
| D652,052 S | 1/2012 | Judy et al. |
| 8,096,947 B2 | 1/2012 | Saigo et al. |
| 8,115,101 B2 * | 2/2012 | Balji .................. G16H 40/63 174/75 C |
| 8,125,484 B2 | 2/2012 | Gering |
| 8,137,273 B2 | 3/2012 | Everett et al. |
| 8,170,887 B2 | 5/2012 | Rosenfeld et al. |
| 8,175,895 B2 | 5/2012 | Rosenfeld et al. |
| 8,182,429 B2 | 5/2012 | Mason |
| 8,211,030 B2 | 7/2012 | Donehoo et al. |
| 8,233,272 B2 | 7/2012 | Fidacaro et al. |
| 8,234,128 B2 | 7/2012 | Martucci et al. |
| 8,235,938 B2 | 8/2012 | Eggers et al. |
| 8,246,546 B2 | 8/2012 | Huiku |
| 8,257,273 B2 | 9/2012 | Pfeiffer |
| 8,266,349 B2 | 9/2012 | Eaton et al. |
| 8,279,586 B2 | 10/2012 | Fidacaro et al. |
| 8,282,567 B2 | 10/2012 | Kolluri |
| 8,285,360 B2 | 10/2012 | Kabasawa |
| 8,315,682 B2 | 11/2012 | Such et al. |
| RE43,869 E | 12/2012 | Lewandowski et al. |
| 8,326,649 B2 | 12/2012 | Rosenfeld |
| 8,343,058 B2 | 1/2013 | Pfeiffer et al. |
| 8,343,062 B2 | 1/2013 | Fortin et al. |
| 8,344,847 B2 | 1/2013 | Moberg et al. |
| 8,396,537 B2 | 3/2013 | Baiji et al. |
| 8,401,874 B2 | 3/2013 | Rosenfeld |
| 8,465,424 B2 | 6/2013 | Aggarwal |
| 8,465,435 B2 | 6/2013 | Van Goudoever et al. |
| 8,469,887 B2 | 6/2013 | Haider |
| 8,471,697 B2 | 6/2013 | Judy et al. |
| 8,483,789 B2 | 7/2013 | Higgins |
| 8,484,393 B2 | 7/2013 | Eaton et al. |
| 8,489,427 B2 | 7/2013 | Simpson et al. |
| 8,515,531 B2 | 8/2013 | Costa Ribalta et al. |
| 8,517,939 B2 | 8/2013 | Parnagian |
| 8,521,556 B2 | 8/2013 | Chbat et al. |
| 8,548,577 B2 | 10/2013 | Muhlsteff et al. |
| 8,562,526 B2 | 10/2013 | Heneghan |
| 8,566,738 B2 | 10/2013 | Van Vlimmeren et al. |
| 8,568,327 B2 | 10/2013 | O'Brien |
| 8,574,156 B2 | 11/2013 | Uutela et al. |
| 8,574,157 B2 | 11/2013 | Hoctor et al. |
| 8,602,985 B2 | 12/2013 | Ali |
| 8,622,913 B2 | 1/2014 | Dentinger et al. |
| 8,639,521 B2 | 1/2014 | Eggers et al. |
| 8,641,757 B2 | 2/2014 | Pintor et al. |
| 8,645,154 B2 | 2/2014 | Eggers et al. |
| 8,649,586 B2 | 2/2014 | Wang et al. |
| 8,665,096 B2 | 3/2014 | Rantala et al. |
| 8,690,786 B2 | 4/2014 | Hersh et al. |
| 8,696,632 B2 | 4/2014 | Giiiepsie, Jr. et al. |
| 8,715,193 B2 | 5/2014 | Takala et al. |
| 8,721,543 B2 | 5/2014 | Saffarian |
| 8,721,556 B2 | 5/2014 | Roteliuk |
| 8,730,243 B2 | 5/2014 | Wenholz et al. |
| 8,734,339 B2 | 5/2014 | Rao et al. |
| 8,737,048 B2 | 5/2014 | Fidacaro et al. |
| 8,737,971 B2 | 5/2014 | van Rooyen et al. |
| 8,740,807 B2 | 6/2014 | Banet et al. |
| 8,744,875 B2 | 6/2014 | Eaton et al. |
| 8,761,851 B2 | 6/2014 | Benni et al. |
| 8,771,197 B2 | 7/2014 | Hatib et al. |
| 8,771,198 B2 | 7/2014 | Kumar et al. |
| 8,773,259 B2 | 7/2014 | Judy et al. |
| 8,775,196 B2 | 7/2014 | Simpson et al. |
| 8,797,714 B2 | 8/2014 | Balji et al. |
| 8,805,019 B2 | 8/2014 | Jeanne et al. |
| 8,808,191 B2 | 8/2014 | Hirsh |
| 8,836,514 B2 | 9/2014 | Rantala |
| 8,840,636 B2 | 9/2014 | Barbut |
| 8,852,094 B2 | 10/2014 | Al-Ali et al. |
| 8,878,677 B2 | 11/2014 | Nielsen |
| 8,882,666 B1 | 11/2014 | Goldberg et al. |
| 8,888,738 B2 | 11/2014 | Gillepsie, Jr. et al. |
| 8,905,939 B2 | 12/2014 | Hatib et al. |
| 8,911,377 B2 | 12/2014 | Al-Ali |
| 8,922,330 B2 | 12/2014 | Moberg et al. |
| 8,923,918 B2 | 12/2014 | Kreger et al. |
| 8,992,431 B2 | 3/2015 | Merilainen |
| 9,024,781 B2 | 5/2015 | Zhang et al. |
| 9,047,648 B1 | 6/2015 | Lekutai et al. |
| 9,070,184 B2 | 6/2015 | Wang et al. |
| 9,101,264 B2 | 8/2015 | Acquista |
| 9,101,335 B2 | 8/2015 | Coffeng |
| 9,125,630 B2 | 9/2015 | Menzel |
| 9,149,188 B2 | 10/2015 | Eng et al. |
| 9,152,268 B2 | 10/2015 | Li et al. |
| 9,153,112 B1 | 10/2015 | Kiani et al. |
| 9,167,968 B2 | 10/2015 | Saeed et al. |
| 9,167,973 B2 | 10/2015 | Steiner et al. |
| 9,189,941 B2 | 11/2015 | Eschelman et al. |
| 9,196,046 B2 | 11/2015 | Meyer |
| 9,198,620 B2 | 12/2015 | Balji et al. |
| 9,204,857 B2 | 12/2015 | Dentinger |
| 9,220,421 B2 | 12/2015 | Woehrle |
| 9,254,104 B2 | 2/2016 | Judy et al. |
| 9,259,187 B2 | 2/2016 | Peyton |
| 9,299,240 B2 | 3/2016 | Anson et al. |
| 9,300,356 B2 | 3/2016 | Winward et al. |
| 9,307,913 B2 | 4/2016 | O'Brien et al. |
| 9,345,641 B2 | 5/2016 | Kraus et al. |

(56) References Cited

U.S. PATENT DOCUMENTS

| | | |
|---|---|---|
| 9,351,640 B2 | 5/2016 | Tran |
| 9,364,153 B2 | 6/2016 | Merritt et al. |
| 9,393,384 B1 | 7/2016 | Kapur et al. |
| 9,433,348 B2 | 9/2016 | Eshelman et al. |
| 9,433,386 B2 | 9/2016 | Mestha et al. |
| 9,445,764 B2 | 9/2016 | Gross et al. |
| 9,460,596 B1 | 10/2016 | Moses |
| 9,462,955 B2 | 10/2016 | Zhou et al. |
| 9,554,740 B2 | 1/2017 | Saeed et al. |
| 9,554,756 B2 | 1/2017 | Menzel |
| 9,607,495 B2 | 3/2017 | Tivig et al. |
| 9,610,060 B2 | 4/2017 | Jaeschke et al. |
| 9,659,365 B2 | 5/2017 | Groth et al. |
| 9,761,100 B2 | 9/2017 | Anson et al. |
| 10,405,757 B2 | 9/2019 | Hughes et al. |
| 2002/0014951 A1 | 2/2002 | Kramer et al. |
| 2005/0020887 A1 | 1/2005 | Goldberg |
| 2005/0197585 A1 | 9/2005 | Brockway et al. |
| 2006/0009699 A1 | 1/2006 | Roteliuk et al. |
| 2006/0076463 A1 | 4/2006 | Drew |
| 2006/0142808 A1 | 6/2006 | Pearce et al. |
| 2006/0235309 A1 | 10/2006 | McIntyre |
| 2006/0281980 A1 | 12/2006 | Randlov et al. |
| 2007/0002791 A1 | 1/2007 | Kasprzyk et al. |
| 2007/0255114 A1* | 11/2007 | Ackermann ..... G01N 33/48792 600/300 |
| 2007/0282208 A1 | 12/2007 | Jacobs et al. |
| 2007/0287924 A1 | 12/2007 | Glocker et al. |
| 2008/0030468 A1 | 2/2008 | Ali et al. |
| 2008/0045814 A1 | 2/2008 | Busch |
| 2008/0058614 A1 | 3/2008 | Banet et al. |
| 2008/0108884 A1 | 5/2008 | Kiani |
| 2008/0154100 A1 | 6/2008 | Thalmeler et al. |
| 2008/0214903 A1 | 9/2008 | Orbach |
| 2008/0214904 A1 | 9/2008 | Saeed et al. |
| 2008/0221461 A1 | 9/2008 | Zhou et al. |
| 2008/0235058 A1 | 9/2008 | Friedman et al. |
| 2008/0255432 A1 | 10/2008 | Nielsen et al. |
| 2008/0288180 A1 | 11/2008 | Hayter |
| 2009/0005703 A1 | 1/2009 | Fasciano |
| 2009/0216132 A1 | 8/2009 | Orbach |
| 2010/0081944 A1* | 4/2010 | Baker, Jr. ............ A61B 5/02125 600/485 |
| 2010/0099991 A1 | 4/2010 | Snyder |
| 2010/0168596 A1 | 7/2010 | Jaeschke et al. |
| 2010/0241013 A1 | 9/2010 | Hatib |
| 2010/0259395 A1 | 10/2010 | Nuthi |
| 2010/0261979 A1 | 10/2010 | Kiani |
| 2010/0261982 A1 | 10/2010 | Noury et al. |
| 2010/0312115 A1 | 12/2010 | Dentinger |
| 2010/0331708 A1 | 12/2010 | Hatib |
| 2011/0009714 A1 | 1/2011 | Zong |
| 2011/0029248 A1 | 2/2011 | Saeed et al. |
| 2011/0060234 A1 | 3/2011 | Zhou et al. |
| 2011/0208066 A1 | 8/2011 | Gnadinger |
| 2011/0263992 A1 | 10/2011 | Guelen et al. |
| 2011/0263994 A1 | 10/2011 | Burns et al. |
| 2011/0270069 A1 | 11/2011 | Acquista |
| 2011/0295085 A1 | 12/2011 | Goldberg |
| 2011/0316704 A1 | 12/2011 | Nielsen et al. |
| 2012/0078665 A1 | 3/2012 | Johnson et al. |
| 2012/0089034 A1 | 4/2012 | Woehrle |
| 2012/0116194 A1 | 5/2012 | Gross et al. |
| 2012/0116218 A1 | 5/2012 | Martin et al. |
| 2012/0123279 A1 | 5/2012 | Brueser et al. |
| 2012/0179017 A1 | 7/2012 | Satou et al. |
| 2012/0191467 A1 | 7/2012 | LaPlante et al. |
| 2012/0197146 A1 | 8/2012 | Tan et al. |
| 2012/0203076 A1 | 9/2012 | Fatta et al. |
| 2012/0253156 A1 | 10/2012 | Muhisteff |
| 2012/0277673 A1 | 11/2012 | Levin et al. |
| 2012/0296177 A1 | 11/2012 | Von Arx et al. |
| 2013/0006126 A1 | 1/2013 | Band et al. |
| 2013/0013331 A1 | 1/2013 | Horseman |
| 2013/0046197 A1 | 2/2013 | Dlugos, Jr. et al. |
| 2013/0053655 A1 | 2/2013 | Castellanos |
| 2013/0085357 A1 | 4/2013 | Huber et al. |
| 2013/0090566 A1 | 4/2013 | Muhisteffet |
| 2013/0109927 A1 | 5/2013 | Menzel |
| 2013/0109928 A1 | 5/2013 | Menzel |
| 2013/0109929 A1 | 5/2013 | Menzel |
| 2013/0204104 A1 | 8/2013 | Michard et al. |
| 2013/0245463 A1 | 9/2013 | Stuebe et al. |
| 2013/0262730 A1 | 10/2013 | Al-Ali et al. |
| 2013/0263855 A1 | 10/2013 | Tivig et al. |
| 2014/0018650 A1 | 1/2014 | Lord |
| 2014/0066765 A1 | 3/2014 | Fan |
| 2014/0073883 A1 | 3/2014 | Rao et al. |
| 2014/0074179 A1 | 3/2014 | Heldman et al. |
| 2014/0077967 A1 | 3/2014 | Alvarez Osuna et al. |
| 2014/0081089 A1 | 3/2014 | O'Neill |
| 2014/0148702 A1 | 5/2014 | Chen |
| 2014/0159921 A1 | 6/2014 | Qualey et al. |
| 2014/0163362 A1 | 6/2014 | Pahlevan et al. |
| 2014/0187941 A1 | 7/2014 | Shusterman |
| 2014/0206964 A1 | 7/2014 | Saffarian |
| 2014/0235963 A1 | 8/2014 | Edwards et al. |
| 2014/0236249 A1 | 8/2014 | Rao et al. |
| 2014/0257058 A1 | 9/2014 | Clarysse et al. |
| 2014/0275849 A1 | 9/2014 | Acquista |
| 2014/0286361 A1* | 9/2014 | Risher-Kelly ......... H02B 1/202 370/537 |
| 2014/0288947 A1 | 9/2014 | Simpson et al. |
| 2015/0097701 A1* | 4/2015 | Al-Ali ................... G06F 21/84 340/870.07 |
| 2015/0155912 A1 | 6/2015 | Winward et al. |
| 2015/0220696 A1 | 8/2015 | Lekutai et al. |
| 2015/0306313 A1 | 10/2015 | Baykal |
| 2015/0313505 A1 | 11/2015 | Acquista |
| 2015/0356255 A1 | 12/2015 | Simpson et al. |
| 2016/0081562 A1 | 3/2016 | Lachhman |
| 2016/0095976 A1 | 4/2016 | Simpson et al. |
| 2016/0125142 A1 | 5/2016 | Awad |
| 2016/0203288 A1 | 7/2016 | Meng et al. |
| 2016/0213924 A1 | 7/2016 | Coleman et al. |
| 2016/0278869 A1 | 9/2016 | Grunwald |
| 2019/0380595 A1 | 12/2019 | Hughes |

FOREIGN PATENT DOCUMENTS

| | | |
|---|---|---|
| WO | WO 1992/022240 | 12/1992 |
| WO | WO 1998/25532 | 6/1998 |
| WO | WO 2006/033812 | 3/2006 |
| WO | WO 2006/083933 | 8/2006 |
| WO | WO 2006/113366 | 10/2006 |
| WO | WO 2013/056160 | 4/2013 |
| WO | WO 2013088314 | 6/2013 |
| WO | WO 2013/158314 | 10/2013 |
| WO | WO 2013/173520 | 11/2013 |
| WO | WO 2013171620 | 11/2013 |
| WO | WO 2014020484 | 2/2014 |
| WO | WO 2015/130705 | 2/2015 |
| WO | WO 2017/070120 | 4/2017 |

OTHER PUBLICATIONS

Supplemental Partial European Search Report in European Application No. 16858074.4 dated May 9, 2019.

International Search Report and Written Opinion for International Application No. PCT/US2016/057553, Notification dated Feb. 16, 2017.

Anliker et al., "AMON: A Wearable Multiparameter Medical Monitoring and Alert System," IEEE Transaction on Information Technology in Biomedicine, Jan. 2005.

Philips M80001A and M80002A Data Sheet, "IntelliVue Patient Monitor MP20/MP20 Junior/MP30," 2004.

U.S. Appl. No. 14/630,399, filed Feb. 24, 2015, Hughes.

* cited by examiner

HEMODYNAMIC MONITORING SYSTEM WITH DETACHABLE DISPLAY UNIT

CROSS-REFERENCE TO RELATED APPLICATIONS

This application is a continuation of International Application No. PCT/US2016/057553, entitled "HEMODYNAMIC MONITORING SYSTEM WITH DETACHABLE DISPLAY UNIT" and on filed Oct. 18, 2016, which claims the benefit of U.S. Provisional Patent Application No. 62/243,555, entitled "HEMODYNAMIC MONITORING SYSTEM WITH DETACHABLE DISPLAY UNIT" and filed on Oct. 19, 2015. The entire contents of each of the above-identified patent applications are hereby incorporated by referenced herein and made a part of this specification.

BACKGROUND

Field

Certain embodiments disclosed herein relate generally to monitoring physiological parameters of a patient, and specifically to a patient monitor configured to monitor parameters of a patient.

Description of Related Art

In many healthcare settings, especially in the care of seriously afflicted cardiac patients, it is desirable or necessary for a healthcare practitioner to be able to monitor generally continuous information about a patient's physiology, such as a patient's cardiac performance or a patient's blood characteristics. Hemodynamic monitoring is typically performed to ensure tissue oxygenation in critically ill patients in different settings. A pulmonary artery catheter (PAC) can generally be used for this task in order to assess cardiac output, a primary determinant of oxygen delivery. Additionally, a variety of minimally invasive hemodynamic monitors are available to provide information of systemic flow and cardiac performance as well as intravascular fluid status. Patient monitoring devices typically include a user interface screen for displaying data acquired about the patient via sensors in communication with the patient monitoring device and with the patient.

SUMMARY

The systems, methods and devices of the disclosure each have innovative aspects, no single one of which is indispensable or solely responsible for the desirable attributes disclosed herein. Some of the advantageous features of some embodiments will now be summarized.

The embodiments disclosed herein describe a patient monitor configured to receive patient-information electrical signals from an invasive patient sensor and a minimally invasive patient sensor, the patient monitor including a base unit and a detachable user interface unit for displaying hemodynamic parameters determined by the base unit. Embodiments of the base unit and user interface unit can be docked together, tethered together through a cabled connection, or physically separated from one another using wireless communication to transmit and receive information. Embodiments of the patient monitor can be configured to switch between invasive and minimally invasive monitoring of hemodynamic parameters of a patient, using invasive measurements to calibrate minimally invasive measurements.

The embodiments disclosed herein describe various features of the patient monitor. For example, the patient monitor can be configured to switch between invasive and minimally invasive monitoring of hemodynamic parameters of a patient and adjust the display of hemodynamic parameters accordingly. As another example, the patient monitor can include a base unit and a detachable user interface unit, where the base unit determines hemodynamic parameters using measurements received from various sensors and the detachable user interface unit displays various user interfaces. Such user interfaces can include a user interface that displays trend data for one or more hemodynamic parameters, a user interface that displays a physiological schematic with corresponding hemodynamic parameter values, a user interface that displays current and historical hemodynamic parameter values in a table, a user interface that displays a bi-variant plot of two hemodynamic parameters, a user interface that displays a hemodynamic calculator for determining output parameter values given a set of input parameter values, and/or a user interface that displays a Bolus cardiac output graph. Because a location may include multiple base units and detachable user interface units, the base unit and the detachable user interface unit can implement a pairing process at startup or when the detachable user interface unit connects or disconnects from the base unit to link a particular base unit to a particular detachable user interface unit. The pairing process can be implemented using a wired or wireless connection source between the base unit and the detachable user interface unit. As another example, the detachable user interface unit is pole-mountable and can communicate with the base unit via a wired or wireless connection. If a connection between the base unit and the user interface unit is lost, the base unit can automatically indicate whether an alarm condition has occurred without the use of the user interface unit and can automatically lower the power of a heater coupled to the base unit if the heater is active. As another example, the base unit can prioritize data sources for heart rate and mean arterial pressure calculations. Such prioritization can include prioritizing sensors coupled to the base unit via an analog input over sensors coupled to the base unit via a digital input.

One aspect of the disclosure provides a patient monitor configured to receive patient-information electrical signals from an invasive patient sensor and a minimally invasive patient sensor. The patient monitor includes a base unit having a housing forming a docking base and a front plate, the docking base including a base unit connector; a plurality of sensor input connectors on an exterior portion of the housing, at least one sensor input connector configured to receive electrical signals from an invasive patient sensor and at least one sensor input connector configured to receive electrical signals from a minimally invasive patient sensor; a wireless communication system comprising an antenna and a transceiver enclosed within the housing; and a latch attached to the housing. The patient monitor further includes a user interface unit having a housing with a bottom portion and a rear portion; a display on a front portion of the user interface unit, the display configured to display hemodynamic parameters determined by the base unit based on the received patient-information electrical signals; a wireless communication system enclosed within the housing; and a user interface connector on the bottom portion of the housing, the user interface connector configured to mate with the base unit connector. In a docked configuration, the user interface connector is configured to directly couple to the base unit connector and the bottom portion of the housing of the user interface unit is configured to contact the docking base of the base unit and at least a portion of the rear portion of the housing of the user interface unit is configured to contact the front plate of the housing of the base unit, and the latch is configured to secure the user interface unit to the base unit. In a tethered configuration, the user interface connector is electrically coupled to the base unit connector using a cable, the cable conducting electrical power and electrical signals between the base unit and the user interface unit. In a detached configuration, the wireless communication system of the user interface unit is configured to wirelessly communicate with the wireless communication system of the base unit.

The patient monitor of the preceding paragraph can include any sub-combination of the following features: where the minimally invasive patient sensor comprises at least one pressure sensor configured to be in fluid communication with a patient's blood vessel through a fluid-receiving region in the pressure sensor and configured to be in electrical communication with the base unit, the pressure sensor being configured to sense a pressure wave in the patient's vasculature and being configured to transmit at least one patient-information electrical signal to the base unit that indicates a hemodynamic parameter of a patient; where the base unit is configured to determine a hemodynamic parameter of a patient based on the patient-information electrical signals received from the invasive patient sensor during a first time period and to determine the hemodynamic parameter of the patient based on the patient-information electrical signals received from the minimally invasive patient sensor during a second time period after the first time period, wherein the hemodynamic parameter based on the patient-information electrical signals received from the minimally invasive patient sensor is calibrated using the patient-information electrical signals received from the invasive patient sensor; where the patient monitor is configured to switch between determining the hemodynamic parameter of the patient based on the patient-information electrical signals received from the invasive patient sensor and determining the hemodynamic parameter of the patient based on the patient-information electrical signals received from the minimally invasive patient sensor; where the docking base is sloped so that liquid flows off of the docking base when the user interface unit is docked on the base unit; where the patient monitor further includes a plurality of analog signal input connectors configured to receive an analog input signal from an external patient monitor system; where the base unit is configured to automatically convert received signals to a physiological parameter based on a maximum expected value of the physiological parameter and a received maximum analog signal from the external patient monitor system; where the user interface unit receives an indication of the maximum expected value of the physiological parameter through an interaction of a user with the display; where the base unit further comprises a conducting portion configured to act as a ground plane for the antenna of the wireless communication system so that a resulting radiation pattern of the antenna preferentially transmits electromagnetic energy in a forward direction relative to the base unit; where the docking base and base unit connector are configured so that the user interface unit cannot be docked on the base unit with the display portion adjacent to the front plate; and where the user interface unit and the base unit are configured such that, in the tethered configuration, the user interface unit cannot be seated in the docking base so that the latch secures the user interface unit in place on the base unit.

Another aspect of the disclosure provides a method for providing an alarm for a patient monitoring system comprising a base unit and a detachable user interface unit when the detachable user interface unit is not electrically coupled to the base unit through a cable or connector. The method includes determining a presence of one or more alarm conditions based at least in part on a value of a hemodynamic parameter of a patient based on patient-information electrical signals received from an invasive patient sensor or a minimally invasive patient sensor. The method includes determining whether the user interface unit is in wireless communication with the base unit. The method includes signaling an alarm on the base unit if there is at least one alarm condition and there is no wireless communication between the user interface unit and the base unit. The method includes signaling an alarm on the user interface unit if there is at least one alarm condition and the user interface unit is wirelessly communicating with the base unit.

The method of the preceding paragraph can include any sub-combination of the following features: where the at least one alarm condition comprises an alarm indicating that at least one hemodynamic parameter is outside a tailored range of accepted values; where the method further includes not signaling the alarm on the base unit if there is at least one alarm condition and the user interface unit is wirelessly communicating with the base unit; where signaling the alarm comprises providing a visual indication of the alarm; and where signaling the alarm comprises providing an audible indication of the alarm.

Another aspect of the disclosure provides a method for controlling a heater coupled to a patient sensor for a patient monitoring system comprising a base unit and a detachable user interface unit when the detachable user interface unit is not electrically coupled to the base unit through a cable or connector. The method includes iteratively commanding the heater to be in a low power state for a first period of time and to be in a high power state for a second period of time. The method includes determining whether the user interface unit is in wireless communication with the base unit. The method includes monitoring a length of time where there is no wireless communication between the user interface unit and the base unit. The method includes setting the power of the heater to be in the low power state if the length of time exceeds a time threshold.

The method of the preceding paragraph can include any sub-combination of the following features: where the length of time is less than or equal to about 2 minutes; where the first period of time is less than or equal to about 20 seconds; where the first period of time is the same duration as the second period of time; where the low power state comprises providing less than or equal to about 200 mW of power to the heater; and where the high power state comprises providing at least about 7.5 W of power to the heater.

BRIEF DESCRIPTION OF THE DRAWINGS

The drawings are provided to illustrate example embodiments described herein and are not intended to limit the scope of the disclosure. Throughout the drawings, reference numbers may be re-used to indicate general correspondence between referenced elements.

DETAILED DESCRIPTION

Various aspects of the disclosure will now be described with regard to certain examples and embodiments, which are intended to illustrate but not to limit the disclosure. Nothing in this disclosure is intended to imply that any particular feature or characteristic of the disclosed embodiments is essential. The scope of protection of certain inventions is defined by the claims.

Example Critical-Care Patient Monitoring System

Figure 1A:
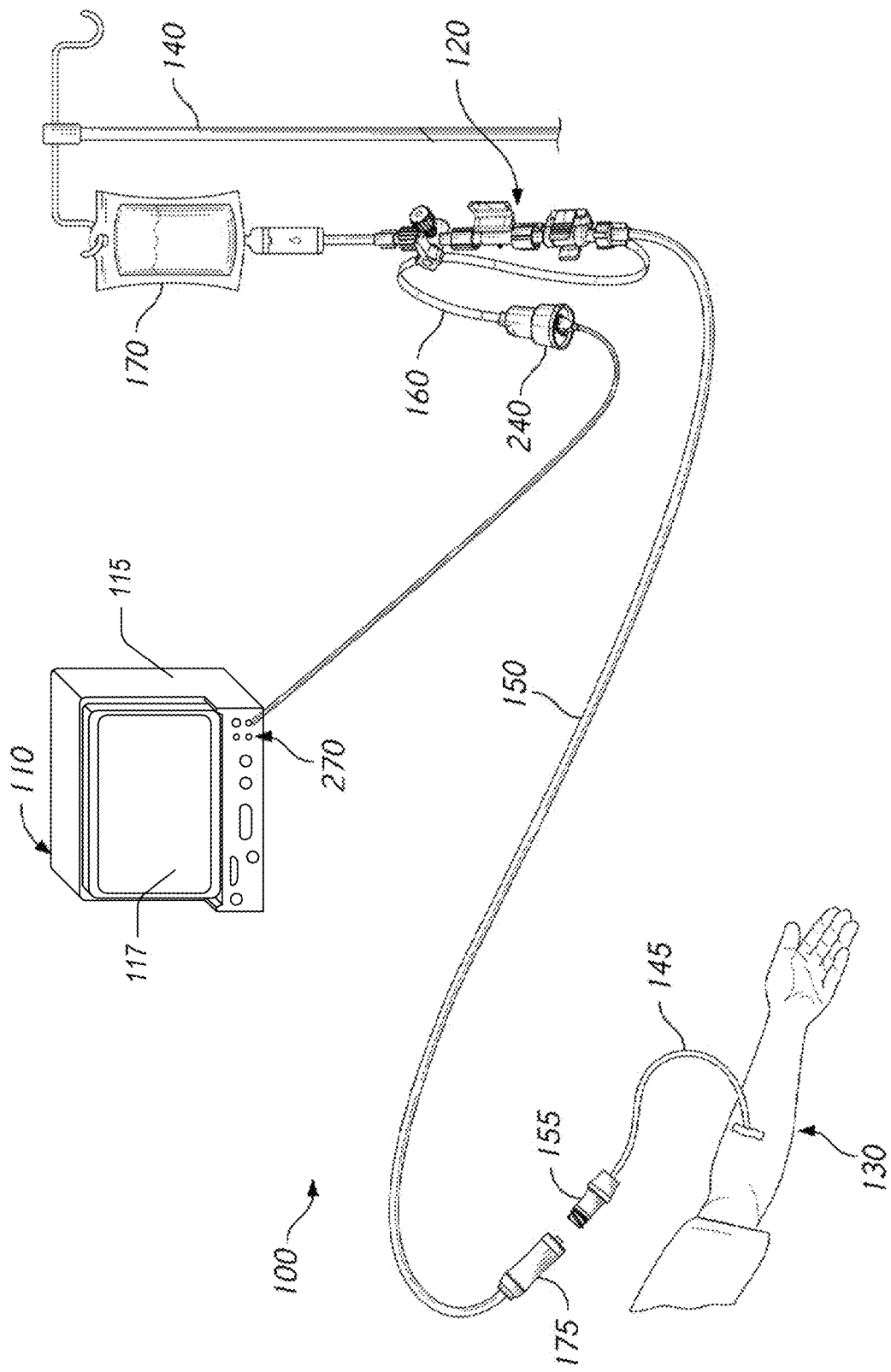
FIGS. 1A-1C illustrate an example critical-care patient monitoring system having a patient monitor comprising a base unit and a detachable user interface unit, the patient monitor placed in electrical communication with a patient sensor.
Figure 1B:
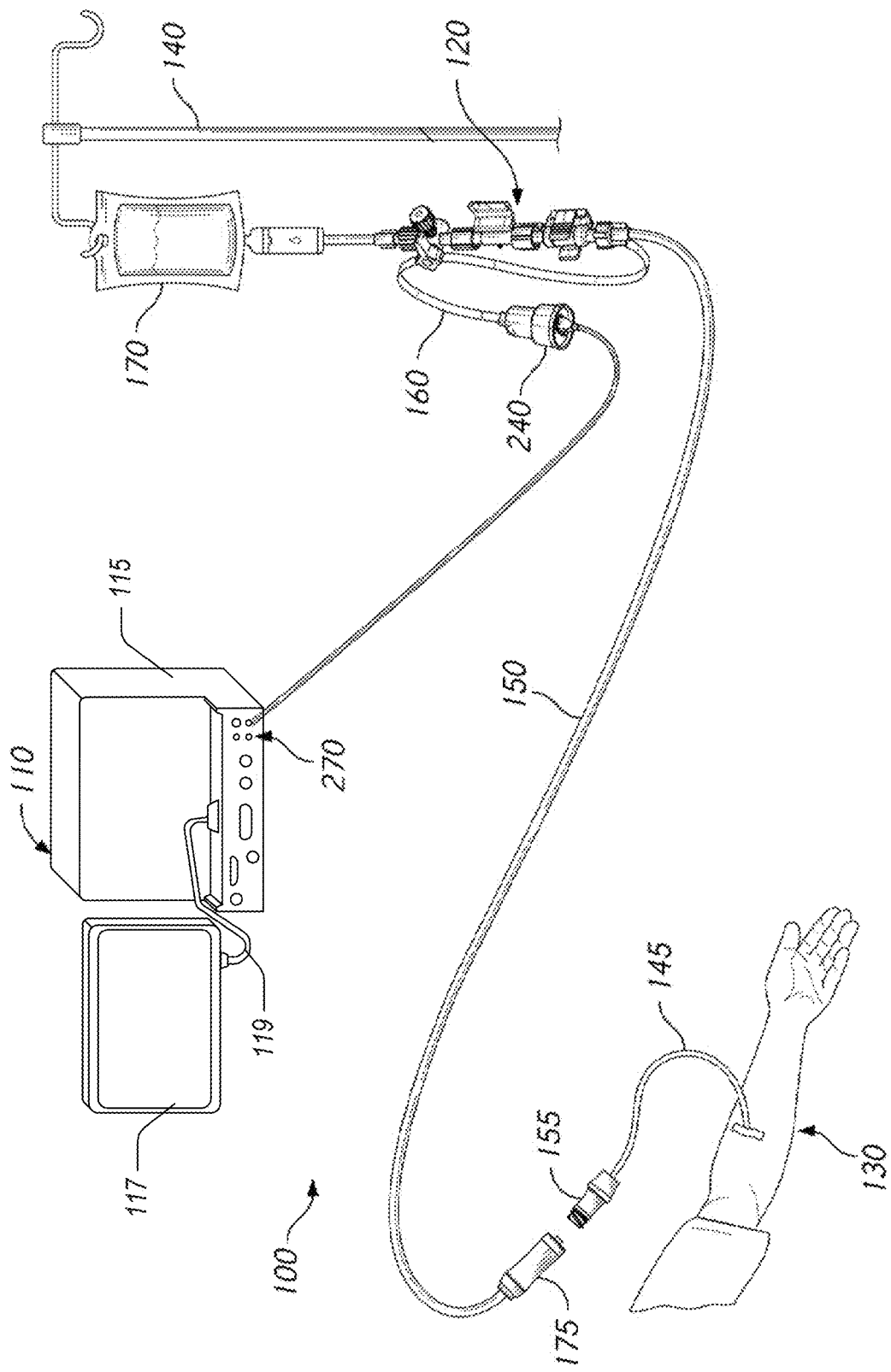
Figure 1C:
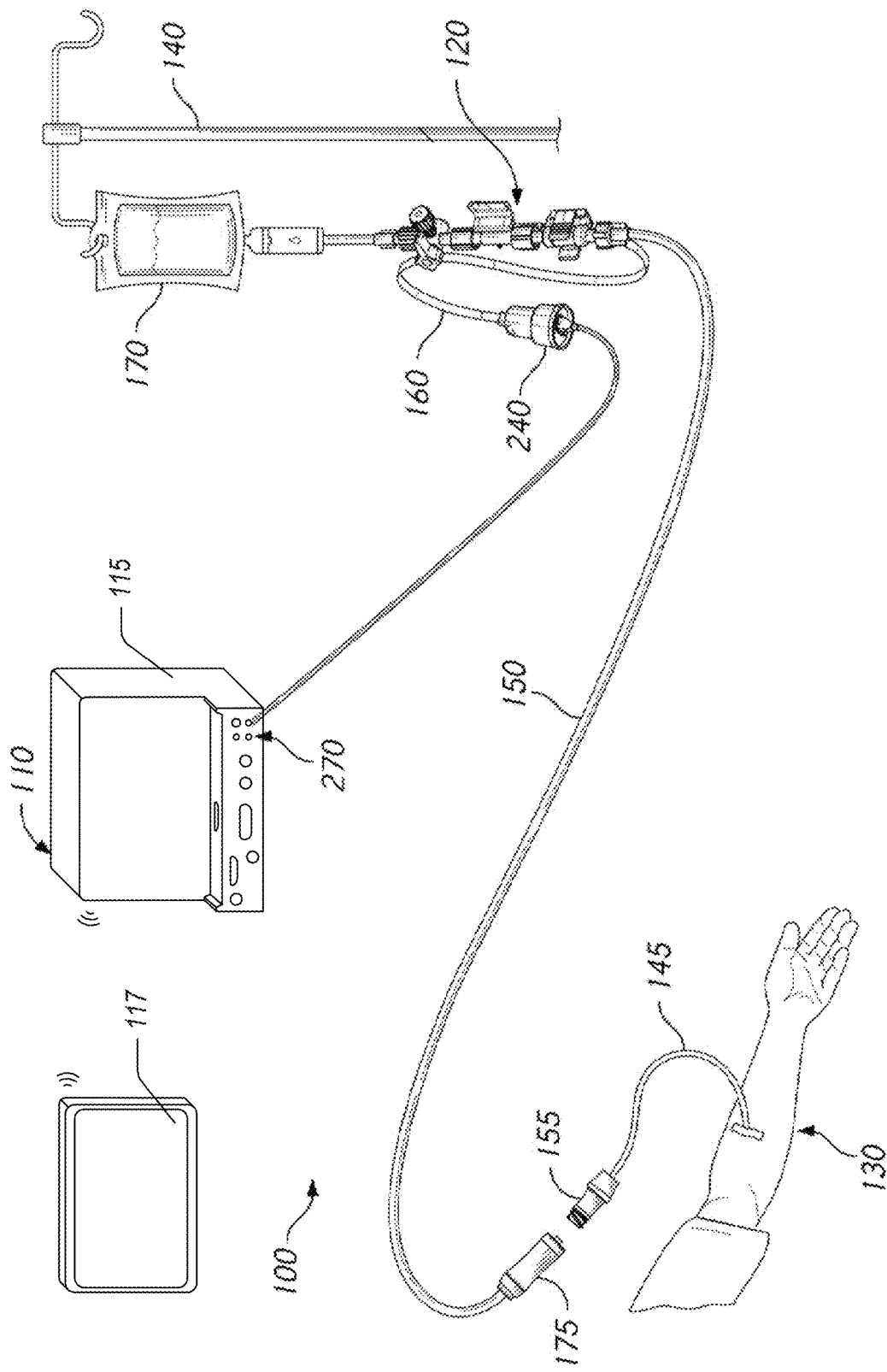
Figure 2A:
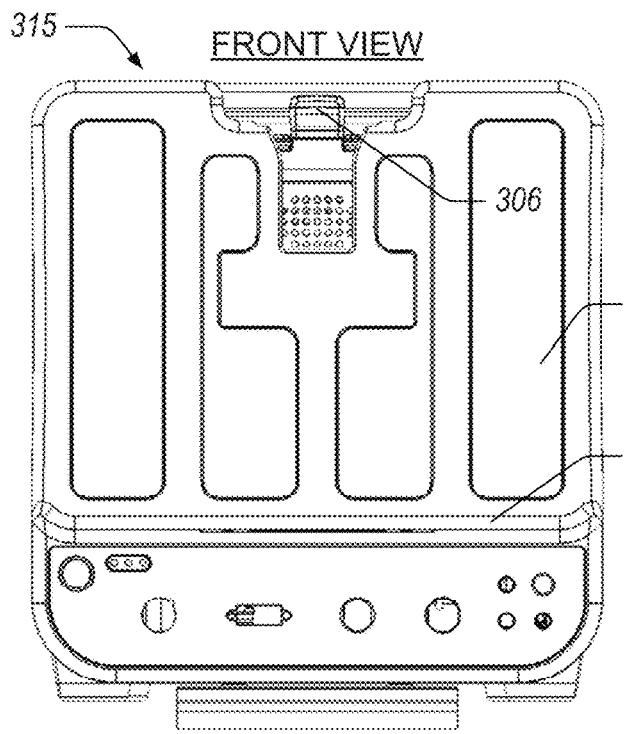
FIGS. 2A-2D illustrate front, side, and top views of an example base unit for a patient monitor.
Figure 2B:
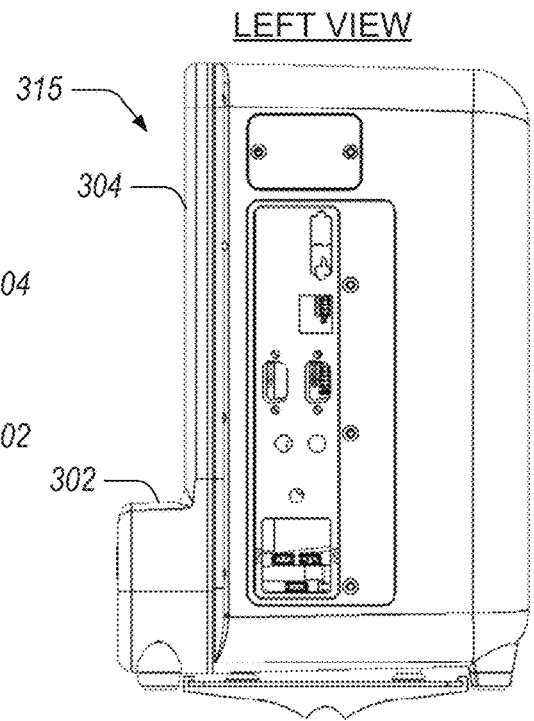
Figure 2C:
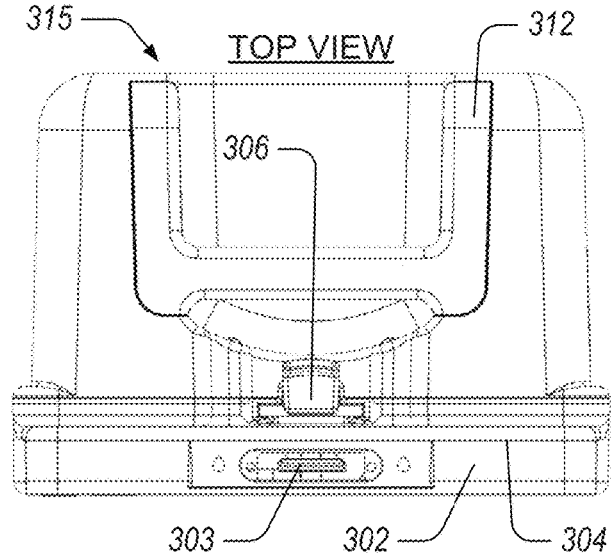
Figure 2D:
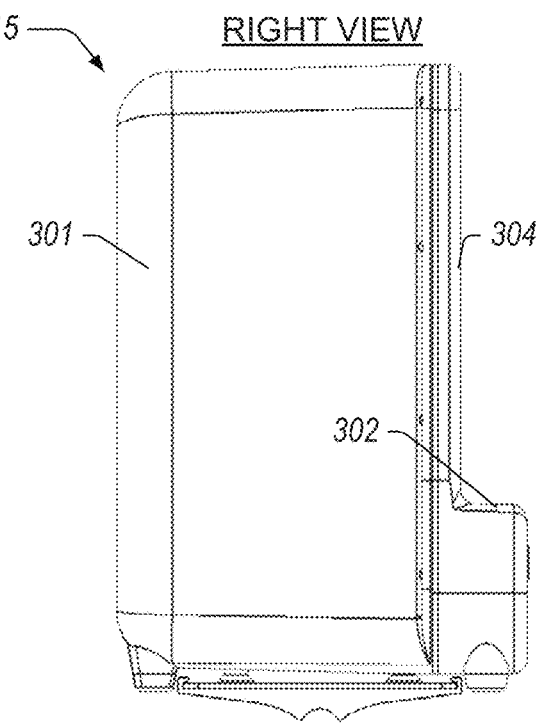

As illustrated in the example of FIGS. 1A-1C, in some embodiments, a critical-care patient monitoring system 100 can include a patient monitor 110, comprising a base unit 115 and a detachable user interface unit 117, placed in electrical communication with a patient sensor 120, such as a cardiac-monitoring sensor and/or a blood parameter sensor, which in turn is placed in fluid communication with a blood vessel of a patient 130, such as by way of a catheter 150. The patient monitoring system 100 can be configured to acquire, analyze, and/or display hemodynamic parameters acquired through both invasive and minimally invasive methods.

As a patient's heart beats, a pressure wave is transmitted through the patient's interconnected system of blood vessels (e.g., veins and arteries). The pressure wave provides information about the patient's cardiac performance, which can be electrically transmitted from the patient sensor 120 to the patient monitor 110, such as by way of a wired connection 160 or a wireless connection. The information about the patient's cardiac performance can be derived or calculated through a mathematical analysis performed by the patient monitor 110 (e.g., through the base unit 115) of the shape of the pressure wave, the ways in which the pressure wave changes over time, and/or the like. As shown, the patient sensor 120 can be positioned on a suitable holding structure 140, such as a pole stand or other holder, and the patient sensor 120 can be in fluid communication with a liquid source 170.

The patient sensor 120, such as a cardiac monitoring sensor, can be configured to transform mechanical motion into electrical energy, such as a pressure sensor that produces an electrical signal that changes over time in response to changes in fluid pressure. The patient sensor 120 can comprise a fluid channel that is in communication with the transducer. The fluid channel can form part of, or be attached to, or otherwise be positioned in fluid communication with, the medical catheter 150 or other tubing or device in fluid communication with a patient's vessel. A distal end of the medical catheter can be inserted into a patient's blood vessel, in contact with the patient's blood, in a conventional manner.

The medical catheter 150 can contain a column of biocompatible fluid, such as saline and/or blood, that interfaces with the blood flowing inside of a patient's blood vessel (e.g., a vein or an artery). The column of fluid can be provided by a liquid source 170, such as an IV bag, that is pressurized or that is gravity-fed into the patient sensor 120, which can be disposed in fluid communication with the patient sensor 120. As the pressure wave from the patient's beating heart is transmitted through the patient's blood vessel, the wave is communicated through fluid interaction with the blood into the column of fluid inside the medical catheter 150 at or near the transducer, where the fluid pressure wave can be converted into a cardiac monitoring electrical signal and transmitted by an electrical wire 160 or wirelessly to the patient monitor 110. The patient monitor 110 can be programmed to analyze the cardiac monitoring electrical signal to provide physiological information about the patient, such as cardiac performance information (e.g., pulse rate, blood pressure such as systolic pressure and/or diastolic pressure, cardiac output, etc.).

In addition to, or instead of, providing cardiac performance information, a blood parameter sensor can be provided with a medical catheter configured to convey information about one or more blood parameters, such as one or more of: a blood gas level (e.g., oxygen and/or carbon dioxide, etc.), a pH level, a hemoglobin level, a hematocrit level, a glucose level, a blood temperature, etc. In some embodiments, one or more blood parameters can be determined by measuring characteristics of light waves that are transmitted into and/or reflected from the blood or another substance in communication with the blood, such as through a system of one or more fiber optic light-transmitting and/or light-receiving cables. In some embodiments, one or more blood parameters can be determined by placing one or more sensors in close communication with the blood, such as a temperature-sensing thermistor suspended in the blood or positioned near the blood.

The patient sensor 120, whether a cardiac-monitoring sensor and/or a blood-parameter sensor, or some other form of patient sensor, can be structured, positioned, and/or oriented in a variety of different ways. The patient monitoring system 100 can be configured to switch, for example, from monitoring hemodynamic parameters derived from data provided by a patient sensor at a pulmonary artery catheter, to monitoring hemodynamic parameters derived from data provided by a patient sensor in a peripheral venous line or a peripheral arterial line. For example, cardiac output of a patient can be measured where an arterial blood pressure waveform of the patient is obtained from a blood pressure monitoring device over a period of time to determine the pulsatility and heart rate of the patient. The nominal stroke volume can then be calculated from the pulsatility and the heart rate. In some embodiments, the hemodynamic parameters derived using minimally invasive techniques (e.g., a sensor in a peripheral venous or arterial line), such as the nominal stroke value, can be calibrated based on the hemodynamic parameters derived using invasive techniques (e.g., thermodilution). Advantageously, this can allow the same patient monitor 110 to obtain, store, and apply calibration factors when switching from monitoring a patient using invasive techniques to minimally-invasive techniques. This can provide the benefit of the patient monitor 110 being able to display hemodynamic parameters obtained through minimally invasive techniques that are calibrated to more accurate measurements obtained using invasive techniques.

For example, the patient monitor 110 can be configured to acquire, derive, and display continuous cardiac output (CCO) and cardiac output derived from pulsatility data. Using the Stewart-Hamilton equation, the patient monitor 110 can calculate cardiac output by the use of an intravascular indicator (e.g., saline) injected into a central or peripheral vein and measured in a peripheral artery using a specialized sensor probe attached to the pressure line (referred to herein as lithium dilution). The patient monitor 110 can use the cardiac output obtained with lithium dilution to calibrate a nominal stroke volume value derived from the arterial blood pressure waveform using a PULSECO algorithm. Alternatively or in addition, the patient monitor 110 can measure cardiac output by implementing other techniques, such as by implementing the cardiac output measurement techniques provided in U.S. Pat. No. 6,071,244 to Band et al., and in U.S. Pat. No. 6,216,094 to Fox Linton et al., each of which is incorporated by reference herein in its entirety. The PULSECO algorithm method is based at least in part on the principles of conservation of mass and power. The patient monitor 110 can calculate stroke volume from an analysis of the stroke volume induced pulsatile change in the arterial blood pressure waveform. The PULSECO algorithm transforms the arterial blood pressure waveform from pressure to a volume equivalent through a compliance and aortic volume correction maneuver. For example, using a lookup table that maps arterial blood pressure values to arterial volume values and that is stored in memory of the patient monitor 110, the patient monitor 110 can use the arterial blood pressure waveform as the basis for calculating a continuous curve describing the general form of the arterial volume changes with every cardiac cycle for which arterial blood pressure is available. The patient monitor 110 can autocorrelate the volume waveform to derive the beat period (e.g., heart rate) and input pulsatile volume change (e.g., stroke volume). The patient monitor 110 can then determine cardiac output by multiplying the stroke volume by the heart rate.

The cardiac output determined by the patient monitor 110 based on the stroke volume and heart rate may be referred to as a pre-calibration cardiac output ($CO_{pre}$). The patient monitor 110 may use a calibration factor, C, to calibrate the stroke volume values derived from the autocorrelation of the volume waveform and, therefore, to calibrate the calculated pre-calibration cardiac output. The calibration factor, C, can be obtained by entering a known cardiac output, $CO_k$, such as a cardiac output obtained through invasive techniques (e.g., thermodilution) or lithium dilution. The calibration factor, C, can then be: $C=CO_k/CO_{pre}$. The calibration factor, C, may also be determined using a nomogram, which calculates the calibration factor using, at least in part, the patient's age, height, gender, and weight. The cardiac output displayed by the patient monitor 110, then, can be $CO=C*CO_{pre}$.

In some embodiments, when switching from determining cardiac output using invasive patient sensors (e.g., pulmonary artery catheters, central venous oximetry catheters, etc.) to determining cardiac output using minimally invasive patient sensors (e.g., CARDIOFLO™ cardiac output sensors, oximetry catheters, etc.), the patient monitor 110 can use the last measurement or a recent measurement of cardiac output determined using the invasive patient sensors to calibrate the cardiac output determined using the minimally invasive patient sensors. In some embodiments, the patient monitor 110 can display the cardiac output determined using the minimally invasive patient sensors as a trend without being calibrated. The display of the uncalibrated trend information can continue until calibration occurs, at which time the patient monitor 110 can adjust the display of the cardiac output to display calibrated cardiac output information. In certain implementations, the cardiac output measurements derived from minimally invasive patient sensors can be calibrated manually (e.g., the patient monitor 110 can receive a calibration factor from a user of the patient monitor 110, such as through the user interface unit 117).

In some embodiments, when switching from invasive to minimally invasive cardiac output monitoring, the patient monitor 110 uses parameters derived from invasive cardiac monitoring to calibrate the parameters derived from the minimally invasive cardiac monitoring. In certain implementations, the patient monitor 110 can update more frequently (e.g., from beat to beat of the heart, every 10 seconds, etc.) one or more of the parameters derived using minimally invasive patient sensors than one or more parameters derived using invasive patient sensors (e.g., which may be updated about every 2 minutes). For example, continuous cardiac output calculated using an invasive patient sensor can take about 2 minutes to acquire. This calculated cardiac output, however, can be a calibrated and accurate measurement of cardiac output. In comparison, cardiac output calculated using data from a minimally invasive patient sensor (e.g., a CARDIOFLO™ cardiac output sensor) can be updated from beat to beat of the heart, but is uncalibrated. In some embodiments, before switching between displaying calibrated and uncalibrated hemodynamic parameters, the patient monitor 110 can be configured to wait at least a predetermined period of time. In some embodiments, the predetermined period of time is about 2 minutes, at least about 4 minutes, or at least about 6 minutes.

In some embodiments, the patient monitor 110 can be configured to operate based on data from invasive patient sensors when an invasive patient sensor is connected to the patient monitor 110, excluding operations based on data and/or discarding data from minimally invasive patient sensors until the invasive patient sensor is disconnected. In some embodiments, the patient monitor 110 can display information derived from the invasive patient sensor after switching to a minimally invasive patient sensor until the parameters derived from the minimally invasive patient sensor are calibrated and/or after a tailored period of time (e.g., about 2 minutes, about 4 minutes, about 8 minutes, etc.). This can reduce potentially misleading changes in displayed hemodynamic parameters when switching between invasive patient sensors and minimally invasive patient sensors. In some embodiments, the patient monitor 110 can be configured to operate based on data from invasive patient sensors when the patient monitor 110 is operating in a mode that utilizes invasive patient sensors, excluding operations based on data and/or discarding data from minimally invasive patient sensors until the patient monitor 110 is operating in a mode that utilizes minimally invasive patient sensors. In some embodiments, the patient monitor 110 can be configured to display on the user interface unit 117 options for selecting which monitoring techniques are to be employed (e.g., choosing between measurements based on invasive or minimally invasive patient sensors).

The user interface unit 117 can be implemented with or without embedded processing capabilities and is releasably attached to the base unit 115. FIG. 1A illustrates the patient monitor 110 with the user interface unit 117 docked in the base unit 115, where the user interface unit 117 is electrically and mechanically coupled to the base unit 115. FIG. 1B illustrates the patient monitor 110 with the user interface unit 117 tethered to the base unit 115, where the user interface unit 117 is electrically coupled to the base unit 115 through tethering cable 119. FIG. 1C illustrates the patient monitor 110 with the user interface unit 117 separated from the base unit 115, where the user interface unit 117 and the base unit 115 are in communication with one another using wireless communication schemes (e.g., WIFI, BLUETOOTH®, ultra-wide band communications, near field communication, WIDI, and/or other forms of radio frequency communications).

As illustrated in FIG. 1A, the base unit 115 and the user interface unit 117 are docked together. The user interface unit 117 can be mechanically coupled to the base unit 115 through mechanical features, such as a latch system, an electronic connector, housing contour shaped to hold the user interface unit 117, and the like. The user interface unit 117 can be electrically coupled to the base unit 115 through mating connectors respectively on the user interface unit 117 and the base unit 115. When docked in the base unit 115, a connector of the user interface unit 117 can mate with a connector of the base unit 115 to establish an electrical connection between the units. This electrical connection can be used to provide power from the base unit 115 to the user interface unit 117 (e.g., to power the user interface unit 117 and/or charge a battery of the user interface unit 117) and/or to communicate information between the units. For example, the base unit 115 can transmit calculated hemodynamic parameters (e.g., cardiac output (CO), conventional filling pressures, pulmonary artery pressures, mixed venous oxygen saturation ($SvO_2$), central venous oxygen saturation ($ScvO_2$), stroke volume (SV), stroke volume variation (SVV), pulse pressure variation, continuous cardiac index (CCI), oxygen saturation ($SO_2$), stroke volume index (SVI), systemic vascular resistance index (SVRI), mean arterial pressure (MAP), mean pulmonary artery pressure (MPAP), arterial oxygen saturation ($S_pO_2$), central venous pressure (CVP), pulmonary artery occlusion pressure (PAOP), partial pressure of oxygen in arterial blood ($PaO_2$), Hemoglobin (Hgb), mixed venous oxygen tension ($PvO_2$), body surface area (BSA), pulmonary vascular resistance (PVR), pulmonary vascular resistance index (PVRI), arterial oxygen content ($CaO_2$), oxygen delivery ($DO_2$), oxygen delivery index ($DO_2I$), right ventricular stroke work index (RVSWI), left ventricular stroke work index (LVSWI), mixed venous oxygen content ($CvO_2$), oxygen volume ($VO_2$), oxygen volume index ($VO_2I$), arterio-jugular differences of oxygen ($avDO_2$), oxygen extraction ratio ($O_2ER$), oxygen extraction index ($O_2EI$), blood pressure, heart rate, etc.) to the user interface unit 117 for display through the electrical connection. As another example, the user interface unit 117 can transmit information (e.g., a user input, user selection, status of the user interface unit 117, etc.) to the base unit 115 through the electrical connection.

As illustrated in FIG. 1B, the base unit 115 and the user interface unit 117 are tethered together. As used herein, the base unit 115 and the user interface unit 117 can be referred to as tethered when the base unit 115 is electrically coupled to the user interface unit 117 through a cable 119 that connects the corresponding connectors on the units. In this configuration, the user interface unit 117 is not mechanically coupled to the base unit 115 in the sense that the base unit 115 does not provide mechanical support to the user interface unit 117 to maintain the unit in a fixed or secured position. The cable 119 can be configured to provide the same or similar functionality that exists when the base unit 115 and the user interface unit 117 are docked together. For example, the cable 119 can be configured to provide electrical power to the user interface unit 117 from the base unit 115. Moreover, the cable 119 can be configured to transmit electrical signals between the units. In some embodiments, when the base unit 115 is tethered to the user interface unit 117, the user interface unit 117 cannot be docked on the base unit 115 without first removing the cable 119. In this configuration, the user interface unit 117 can be mounted or positioned away from the base unit 115, but can still be configured to receive power from the base unit 115 rather than relying on battery power. The user interface unit 117 can be configured to mount to a post, a bed, a pole, or other similar structure, such as structures that are common in hospital rooms or other critical care rooms or areas. Thus, even if the base unit 115 is positioned somewhere inconvenient, the user interface unit 117 can be positioned in a desirable or suitable location for use by health professionals treating a patient.

As illustrated in FIG. 1C, the base unit 115 and the user interface unit 117 are physically separated (e.g., undocked and untethered) from one another. The base unit 115 and the user interface unit 117 can be configured to communicate wirelessly with one another using any number of suitable wireless communication protocols, as described herein. When the user interface unit 117 is not docked or tethered to the base unit 115, the user interface unit 117 can be powered by a battery. In some embodiments, the user interface unit 117 includes an electrical connection configured to receive power from a power cord or the like to provide external power to the unit. As described herein, a user interface unit 117 can be configured to wirelessly pair with multiple base units 115. In this way, if a user interface unit 117 gets damaged or otherwise fails to function properly, a new user interface unit 117 can be provided to maintain the ability to monitor the hemodynamic properties calculated and provided by the base unit 115.

The patient monitor 110 of the critical-care patient monitoring system 100 can comprise a computer processor housed in the base unit 115, memory housed in the base unit 115 that stores hemodynamic parameters determined for a current patient and one or more (e.g., 3, 4, 5, etc.) previous patients, wherein the base unit 115 can be configured to determine one or more hemodynamic parameters based at least in part on information obtained from the patient sensor 120, a user interface unit 117 configured to display physiological information about the patient (including one or any combination of any of the physiological information that the base unit 115 is configured to determine), a power source (such as a battery or a power cord), and one or more electrical connectors, 270, 240 configured to establish an electrical connection with the patient sensor 120, such as by way of an attachment with one or more electrical connectors 240 that form part of the patient sensor 120. The base unit 115 of the patient monitor 110 can be configured to receive one or more patient-information electrical signals that convey information about a patient's physiological conditions. The user interface unit 117 is detachable from the base unit 115. The base unit 115 includes the one or more processors and other electrical circuitry used in processing the signals to determine the monitored hemodynamic parameters. In certain implementations, the user interface unit 117 does not calculate any of the monitored hemodynamic parameters that it displays.

In some healthcare settings, the distance between the transducer portion of the patient sensor 120 and the patient monitor 110 can be significant, such as when the transducer is positioned on a pole stand 140 or in some other location relatively close to the entry point of the medical catheter into the patient's body (such as into the patient's arm 130 or some other location) and the patient monitor 110 is located on a stand in a hospital room several feet away from the entry point. A fluid catheter 145 attached to the patient can be connected to the fluid line 150 from the sensor 120 by way of a pair of fluid connectors, such as corresponding male and female fluid connectors 155, 175. The detachable user interface unit 117 can advantageously allow the user interface unit 117 to be mounted at a convenient location for hospital personnel, such as when the position of the base unit 115 is dictated or influenced by the patient sensor 120, geometry of the patient's room, access to power cords, or the like. This allows the healthcare professional to mount the user interface unit 117 somewhere more convenient or to leave the user interface unit 117 detached and unmounted (e.g., portable).

In some embodiments, the electrical connection with the patient sensor 120 is achieved by attaching an electrical connection portion 240 of the patient sensor 120 to a proximal electrical connection portion of the non-disposable cable, and then attaching a distal connection portion of the non-disposable cable 270 to an electrical connection portion of the computer monitor.

The electrical information can be conveyed in some embodiments wirelessly, such as by way of an electromagnetic short-range signal, such as over a Wi-Fi network or by way of a BLUETOOTH or ZigBee signal, or by some other wireless protocol that is acceptable or utilized in a healthcare setting. Any description or illustration in this specification of an electrical wire 160, 250, or electrical connection 240 can be accomplished in a wireless manner and such descriptions or illustrations of wires or electrical connections should be understood to also refer to and encompass wireless connections.

Example Base Unit of a Patient Monitor

FIGS. 2A-2D illustrate front, side, and top views of an example base unit 315 for a patient monitor, such as the patient monitor 110 described herein with reference to FIGS. 1A to 1C. The example base unit 315 includes a housing 301 generally enclosing electronic components configured to carry out the processes of the base unit 315, including but not limited to, receiving patient sensor electronic information, processing the received information to derive hemodynamic parameters, determining alarms based on the derived parameters, displaying information, and the like. The housing 301 of the base unit 315 forms a docking base 302 configured to support a rear portion of a user interface unit 117 when docked. The docking base 302 includes a docking connector 303 configured to electrically and mechanically couple to a mating connector on a rear portion of the user interface unit 117. The housing 301 of the base unit 315 forms a front plate 304 configured to support a rear portion of a user interface unit 117 when docked on the base unit 315.

The base unit 315 includes a latch 306 configured to secure the user interface unit 117 in place when docked on the base unit 315. The latch 306 can be configured to be actuated to alternately secure and release the user interface unit 117. When docked with the base unit 315, the latch 306 can be configured to sufficiently secure the user interface unit 117 to the base unit 315 so that a user can move the base unit 315 without having to independently secure or hold the user interface unit 117 against the base unit 315. In some embodiments, the latch 306 is configured to sufficiently secure the user interface unit 117 against the base unit 315 so that the units can be treated as a unitary patient monitor. For ease of handling, a handle 312 can be provided on the base unit 315. The handle 312 can be stowed in a first position so as to be substantially aligned with a top portion of the housing 301, and can be raised in a second position, raising above the top portion of the housing 301, to facilitate carrying and moving the base unit 315. The handle 312 can be configured to allow a user to carry the base unit 315 with one hand while the user interface unit 117 is docked on the base unit 315.

The docking base 302 can be configured to be generally tilted with respect to horizontal so that liquid tends to run off the docking base 302 rather than pooling. In addition, in some embodiments, the docking base 302 can generally slope from the exterior edges towards a central or mid-point so that liquids generally tend to run towards the mid-point and flow off of the docking base 302. For example, when the user interface unit 117 is docked on the base unit 315, the connectors of the units can mate and any liquid can run off the docking base 302 rather than pooling around and/or damaging the connector 303 or the electrical contacts of the connector 303 or the connector on the user interface unit 117.

Example Base Unit and User Interface Unit of a Patient Monitor

Figure 3:
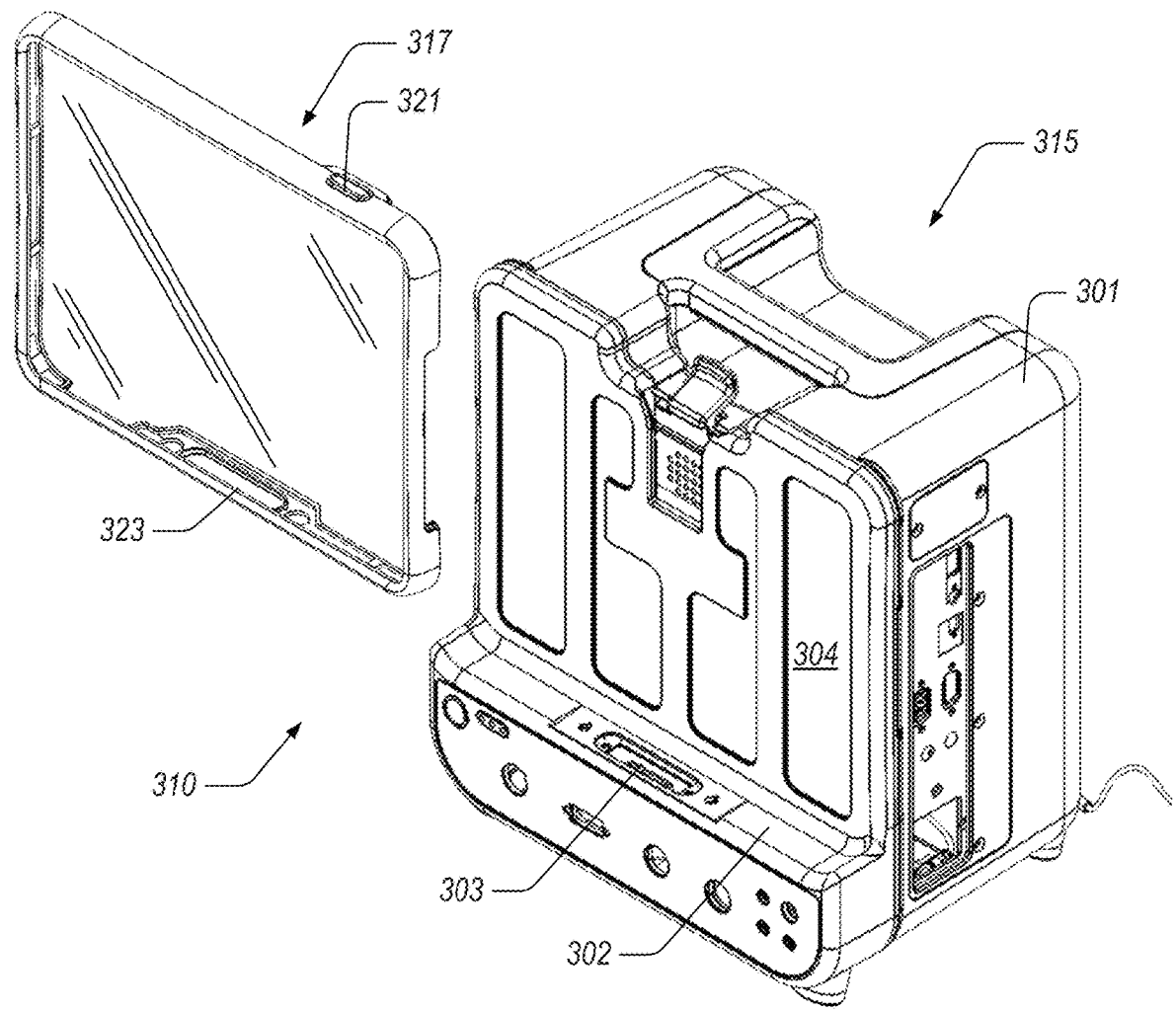
FIG. 3 illustrates an isometric view of an example user interface unit with the example base unit illustrated in FIGS. 2A-2D, together forming a patient monitor.

FIG. 3 illustrates an isometric view of an example user interface unit 317 with the example base unit 315 illustrated in FIGS. 2A-2D, together forming a patient monitor 310. The patient monitor 310 can be similar to the patient monitor 110 described herein with reference to FIGS. 1A to 1C. The example user interface unit 317 can include a display 319 for displaying hemodynamic parameter values and/or trends. Information displayed by the display 319 is discussed in greater detail below with respect to FIGS. 9-14. The display 319 can comprise a touchscreen configured to receive input from a user through contact with the touchscreen. The display 319 can be configured to display user interface features with which the user can interact to control the patient monitor 310. The user interface unit 317 can include one or more physical user interface elements 321 configured to allow user input from sources other than the display 319 (e.g., the touchscreen).

The user interface unit 317 can include a connector 323 configured to mate with the connector 303 on the base unit 315 when the user interface unit 317 is seated against the docking base 302. The connector 323 and connector 303 can be configured to mate together in one configuration so that the display 319 of the user interface unit 317 faces outward, away from the front plate 304 of the base unit 315. In some embodiments, the housing 301 of the base unit 315 includes one or more features that prevents the user interface unit 317 from being docked on the base unit 315 so that the display 319 faces the face portion 304 of the base unit 315. In some embodiments, the user interface unit 317 includes one or more features that prevents the user interface unit 317 from being docked on the base unit 315 so that the display 319 faces the face portion 304 of the base unit 315.

The connector 323 of the user interface unit 317 and the connector 303 of the base unit 315 can be configured to be electrically coupled using a cable that connects to both of the connectors. This configuration can be referred to as tethered, or the user interface unit 317 is tethered to the base unit 315 when the connectors are coupled using a cabled connection. When tethered, the configuration of the connectors can be such that the user interface unit 317 cannot be docked on the base unit 315 when tethered. For example, to dock the user interface unit 317 to the base unit 315 after being tethered, the cable coupling the connectors should be removed to allow the user interface unit 317 to seat correctly in the docking base 302 so that the connectors mate.

Example Wireless Communication System of a Base Unit

Figure 4A:
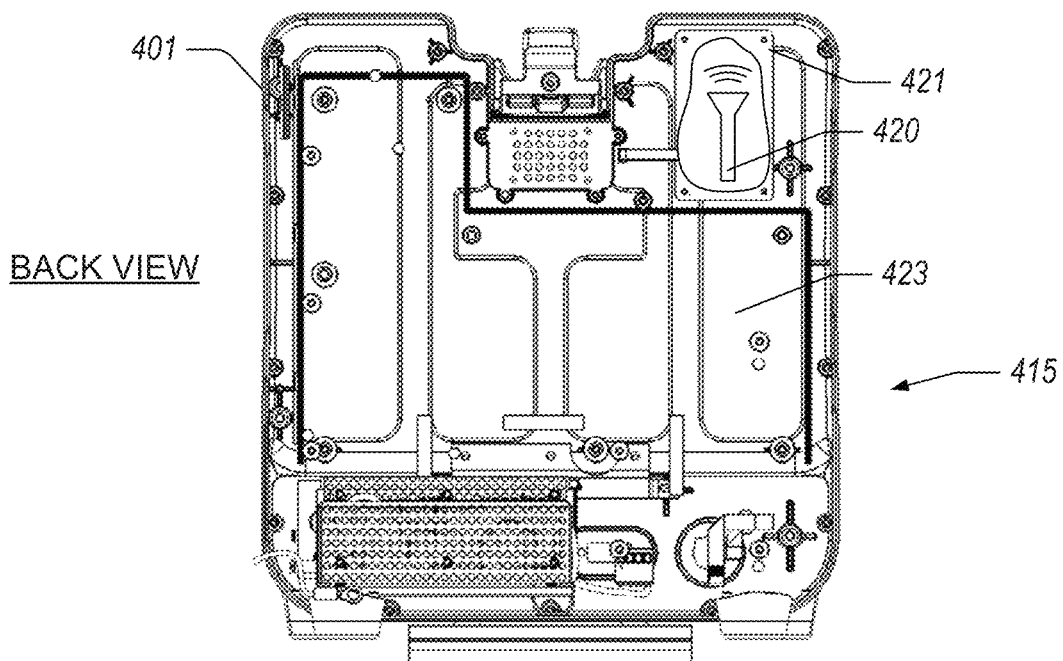
FIGS. 4A-4B illustrate partial cut-away views of a base unit having a wireless communication system comprising an omni-directional antenna.
Figure 4B:
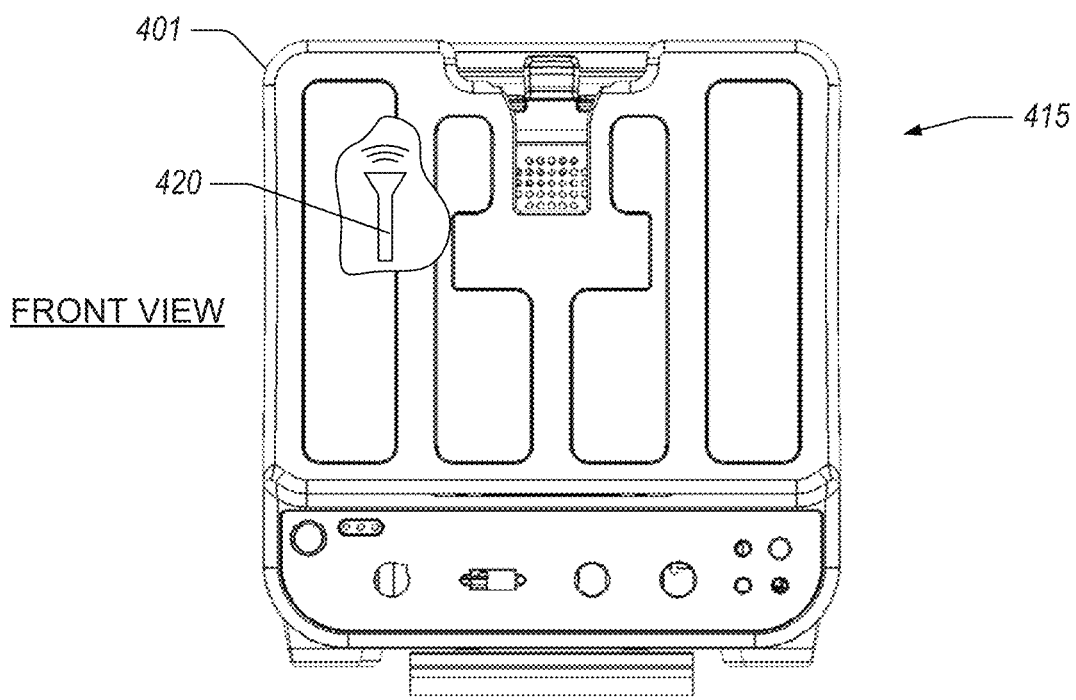

FIGS. 4A-4B illustrate partial cut-away views of a base unit 415 having a wireless communication system 421 comprising an omni-directional antenna 420. FIG. 4A illustrates a back view of the base unit 415 with a portion of the housing 401 removed to reveal internal components of the base unit 415. Positioned within the housing 401 can be a wireless communication system 421. A ground plane and/or RF reflector 423 can be positioned within the housing 401, wherein the ground plane and/or RF reflector 423 can be a piece of metal positioned on a back side of the housing 401. The ground plane 423 can be configured to provide electromagnetic shielding to components within the housing 401, protecting them from potential sources of electromagnetic interference from outside sources. Similarly, the ground plane 423 can be configured to reduce electromagnetic interference produced by the components of the base unit 415 within the housing 401.

The wireless communication system 421 can include an omni-directional antenna 420 configured to send and receive wireless communication from the user interface unit, for example. In certain implementations, the antenna 420 can interact with the ground plane 423 to provide a directional wireless signal. For example, the ground plane 423 can act to reduce electromagnetic waves produced by the antenna 420 that exit the housing 401 out of the rear of the housing 401. Similarly, the ground plane 423 can effectively act as an electromagnetic reflector for the antenna 420, redirecting radiated energy in a forward direction relative to the base unit 415. This can allow the effective radiation pattern of the antenna 420 to appear to be directional even though the antenna 420 is omni-directional. This can advantageously increase wireless range forward of the base unit 415, potentially allowing the user interface unit 317 to be used from farther away than if there were no ground plane configured to increase forward projection of radio frequency energy emitted by the antenna 420. This can also be advantageous because it is generally more likely that the user interface unit 317 is to be used while the user interface unit 317 is in front of the base unit 415 rather than when the user interface unit 317 is behind the base unit 415.

In some embodiments, the design of the wireless communication system 421 and/or antenna 420 is configured to transfer energy to the housing 401 so the housing 401 acts as a transmitter or acts to enhance the transmission and reception capabilities of the antenna 420. This may occur due at least in part to the proximity of the antenna 420 to the housing 401, the housing including one or more electrically conducting plates. In this way, the housing 401 can act to enhance the way radio frequency energy is radiated by effectively reflecting the RF signal produced by the antenna 420. In some embodiments, the antenna 420 is a stamped metal antenna having a ground plane on a printed circuit board. The housing 401 of the base unit 415 can at least partially be a metal housing. The metal housing, in some implementations, can increase the effective size of the ground plane which thereby increases the reflective properties of the housing 401 and antenna 420, thereby increasing radiation strength.

Using a Detachable User Interface Unit Separated from a Base Unit

Figure 5:
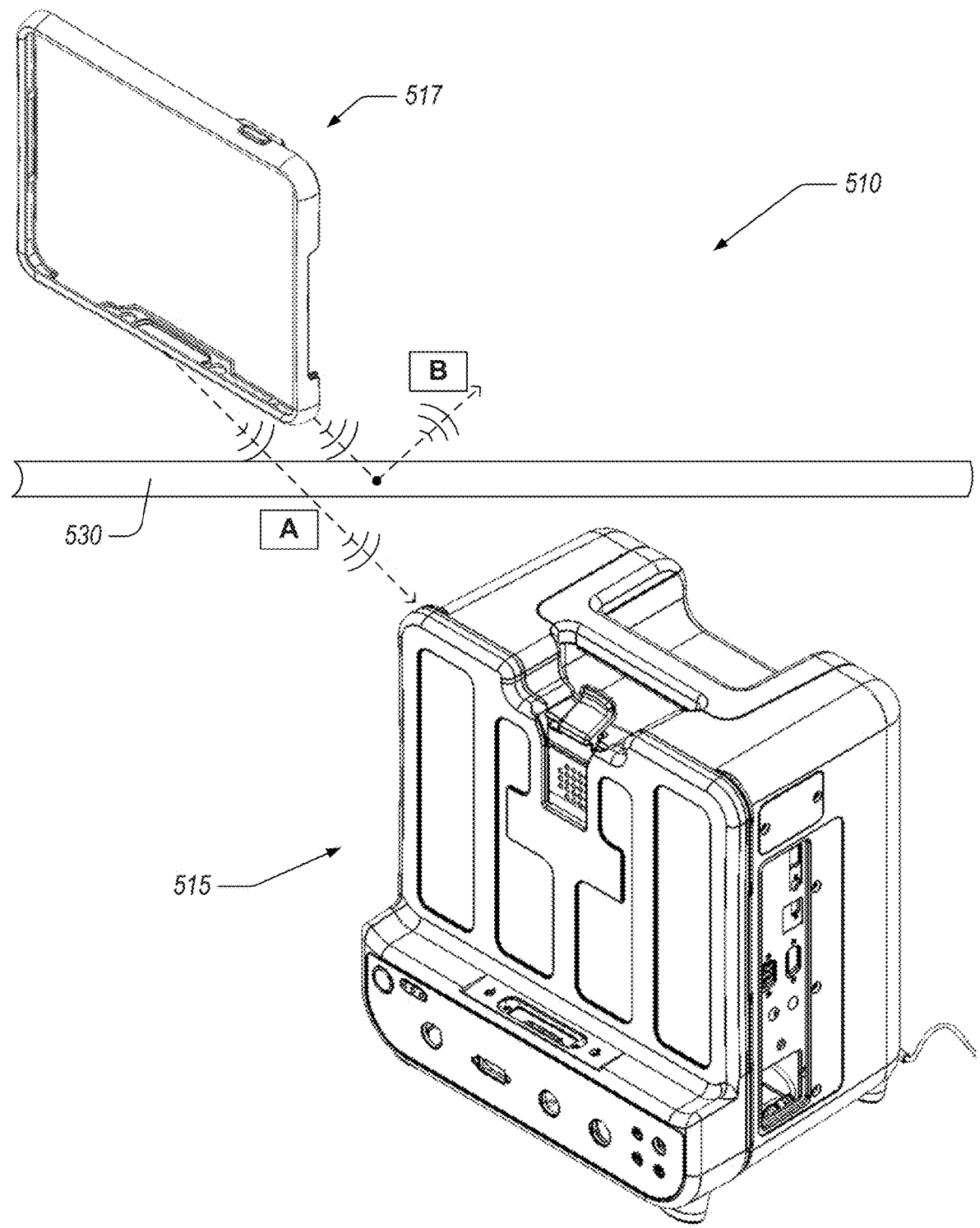
FIG. 5 illustrates a user interface unit separated from a base unit of a patient monitor, the units being separated by a barrier.

FIG. 5 illustrates a user interface unit 517 separated from a base unit 515 of a patient monitor 510, the units being separated by a barrier 530, such as a wall or other obstruction. In the illustrated scenario "A," the wireless signal from the user interface unit 517 is sufficient to travel through the barrier 530 to the base unit 515. In the illustrated scenario "B," the wireless signal from the user interface unit 517 is reflected and/or attenuated by the barrier 530 such that the wireless signal does not reach the base unit 515. When the wireless signal does not reach the base unit 515, such as for a tailored length of time, the base unit 515 can be configured to signal a loss of signal on the base unit 515 itself. For example, audible alarms or alerts can sound indicating that the base unit 515 does not detect a compatible user interface unit 517. As another example, a display on the base unit 515 can be used to indicate that the user interface unit 517 is out of range.

In some embodiments, the base unit 515 can use the strength or presence of the wireless signal from the user interface unit 517 as a proxy for a proximity sensor. For example, when the base unit 515 detects a wireless signal from the user interface unit 517, the base unit 515 can indicate that a compatible or suitable user interface unit 517 is sufficiently close to the base unit 515 to function properly or adequately.

In some embodiments, when the base unit 515 determines that the user interface unit 517 is too far from the base unit 515 (e.g., because no wireless signal is detected or a wireless signal below a threshold strength is detected), one or more alarms can be provided at the base unit 515. In addition, in such circumstances, specialized control functions can be implemented to increase safety of the patient. Examples of processes or methods related to the relative positions of the base unit 515 and the user interface unit 517 are described in greater detail herein with reference to FIGS. 7 and 8.

Example Features of a Base Unit

Figure 6A:
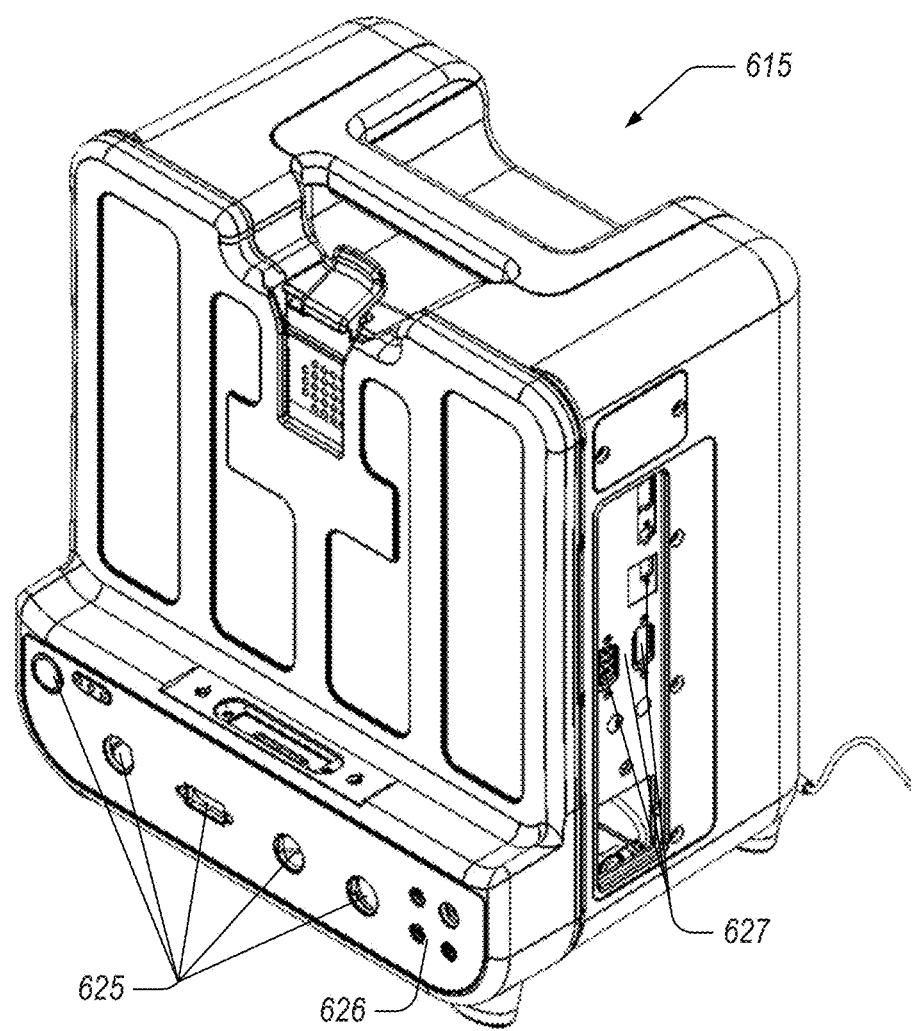
FIG. 6A illustrates an example base unit having a plurality of analog inputs configured to receive analog signals from an external monitoring system.

FIG. 6A illustrates an example base unit 615 having a plurality of analog inputs 626 configured to receive analog signals from one or more external monitoring systems, the analog signals corresponding to measured parameters. The base unit 615 can be configured to automatically scale and display the received signals for display on a user interface unit 517. The base unit 615 can include a number of connectors 625 for receiving patient sensor electrical information directly from one or more patient sensors, such as pulse oximeters, thermodilution sensors, pressure sensors, and the like. The base unit 615 can also include connectors 627 for connecting to one or more peripheral devices, to connect to communications networks, and/or to connect diagnostic or test devices (e.g., USB sticks). In some embodiments, the base unit 615 includes a network connection for connecting to an internal hospital network to relay and/or retrieve information from one or more databases related to the patient being monitored.

The analog signal inputs 626 can be configured to receive an analog signal from one or more external monitoring systems. The base unit 615 can be configured to receive the analog signals for conversion into an appropriate parameter for display. For example, an external monitor system can be configured to measure end-systolic volume in mL. The external monitor system can include an analog output that outputs an analog voltage signal correlated to the measured end-systolic volume. When coupling the analog output from the external monitor system to the base unit 615, the base unit 615 can be configured to expect a max voltage signal corresponding to a maximum voltage that may be put out by the external monitor unit. A user can use the user interface unit 517 to input a maximum measured value (e.g., 150 mL for the end-systolic volume) corresponding to the maximum voltage sent by the external monitor system. The base unit 615 can use this information to subsequently scale the received analog voltage to map it to an appropriate value for the measured parameter, as measured by the external monitoring system. As a particular example, if the user inputs that the maximum measured value is 150 mL, and the external monitor sent a 10 V signal to indicate the maximum output voltage corresponding to the maximum measured voltage, the base unit 615 can be configured to multiply the received analog voltage by 15 mL/V to convert the analog signal into the appropriate measured value for display. This can allow the base unit 615 to incorporate measurements from external systems for display on the user interface unit 517. In some embodiments, the base unit 615 can include 2 analog inputs, 2 or more analog inputs, 3 or more analog inputs, 4 or more analog inputs, 5 or more analog inputs, or 6 or more analog inputs. In some embodiments, the base unit 615 can be configured to receive both a high signal and a low signal to indicate the upper and lower bounds of potential signals on the analog signal inputs 625.

In some embodiments, the base unit 615 can be configured to read a sufficiently large dynamic range of input voltages at the analog signal inputs 626 so that an expected voltage range does not need to be entered into the base unit 615. Rather, the base unit 615 can be configured to receive input indicating a largest (and smallest) expected measured value and that value can be correlated with analog input signal(s) received from an external monitor system, wherein the received analog signal(s) corresponds to a maximum (minimum) analog voltage corresponding to the largest (smallest) expected measured value.

In some embodiments, not shown, the base unit 615 includes one or more digital inputs and/or one or more serial inputs in place of the one or more analog inputs 626 or in addition to the one or more analog inputs 626. The base unit 615 may prioritize data sources if more than one sensor is coupled to the base unit 615. For example, if a cardiac output sensor (e.g., a CARDIOFLO™ sensor) is coupled to the base unit 615, a second sensor is coupled to an analog input, and/or a third sensor is coupled to a digital input, the base unit 615 may process data received via the cardiac output sensor first, process data received via the analog input 626 second, and process data received via the digital input third. In some embodiments, the base unit 615 ignores or discards data received via the analog input 626 and the digital input while data continues to be received from the cardiac output sensor. If an error occurs and/or data is no longer received from the cardiac output sensor (e.g., the cardiac output sensor malfunctions or is disconnected), then the base unit 615 may begin to process data received via the analog input 626 and ignore or discard data received via the digital input. If an error occurs and/or data is no longer received from the cardiac output sensor and the analog input 626 (e.g., the cardiac output sensor and/or the sensor coupled to the analog input 626 malfunction or are disconnected), then the base unit 615 may begin to process data received via the digital input. As another example, if a thermal coil cable (e.g., to perform thermodilution) and a cardiac output sensor are both coupled to the base unit 615, the base unit 615 may cause the user interface unit 517 to display a user interface requesting a practitioner to select either the PA catheter cables or the cardiac output sensor cable for use in determining the hemodynamic parameter values. Thus, in some embodiments, the base unit 615 can allow the user to elect fully or minimally invasive measurements. Once elected, the base unit 615 may further require the unelected input to be disconnected from the base unit 615 (e.g., via a prompt presented on the user interface unit 517).

Figure 6B:
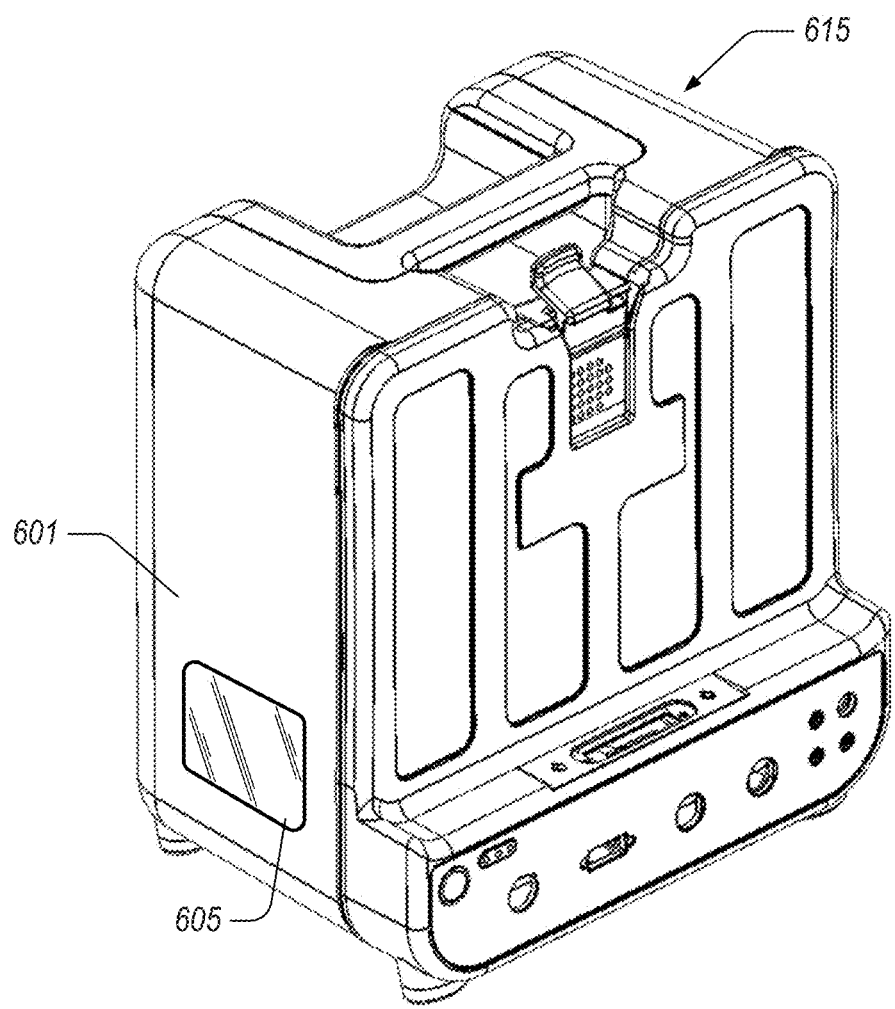
FIG. 6B illustrates the example base unit having a display screen configured to display one or more hemodynamic parameters, an alarm status, a status of a user interface unit, or other similar information.

FIG. 6B illustrates the example base unit 615 having a display screen 605 configured to display one or more hemodynamic parameters, an alarm status, a status of a user interface unit 517, or other similar information. The display screen 605 can be configured to display information at least in part as a redundant display system in case a corresponding user interface unit 517 breaks, is lost, or otherwise fails to operate properly. The display screen 605 can be configured to be flush with the housing 601 and integrated with it. The display screen 605 can be a non-touchscreen display. In some embodiments, the display screen 605 is configured to display a single measured value, multiple measured values, alarm statuses, connection states, wireless communication states, or the like.

In some embodiments, when the base unit 615 loses a wireless connection with the user interface unit 517, the display screen 605 of the base unit 615 can be activated and/or configured to display this information. In some embodiments, such as where the user interface unit 517 is separated and no longer in wireless communication with the base unit 615, the display screen 605 can be configured to display alarm statuses or current alarms. This can be advantageous where a user interface unit 517 is misplaced, broken, or otherwise unavailable so that the healthcare professionals can sufficiently monitor the patient.

The display screen 605 of the base unit 615 can be configured to indicate a state of a heater used in patient monitoring (e.g., power state, power level, etc.). The display screen 605 can be configured to indicate a connection state between the base unit 615 and the user interface unit 517. The display screen 605 can be configured to provide a reduced or minimal display for selected, predetermined, and/or critical hemodynamic parameters.

Figure 7:
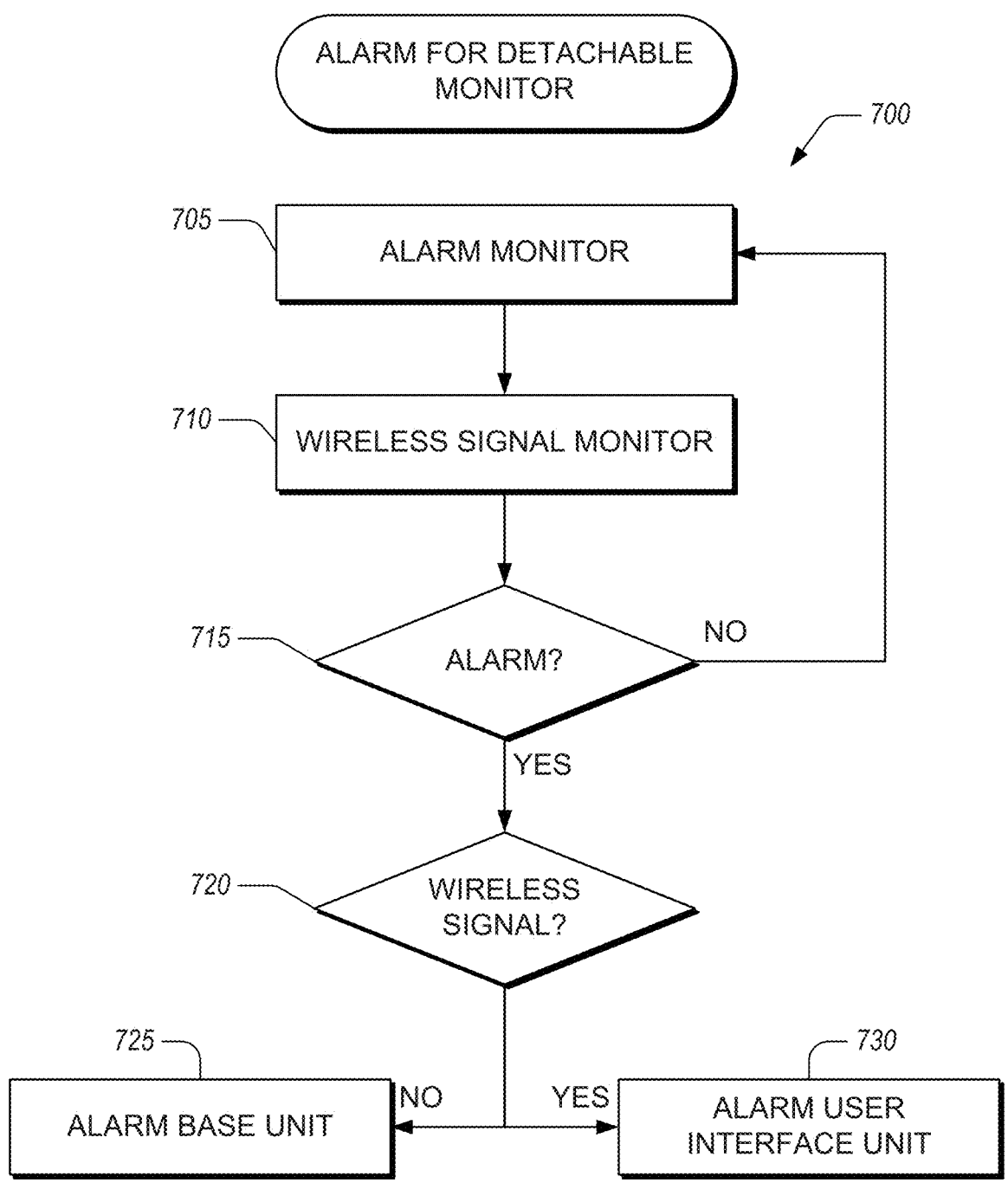
FIG. 7 illustrates a flow chart of an example method for providing alarms for a patient monitor that includes a base unit and a detachable user interface unit configured to display hemodynamic monitoring information provided by the base unit.

Example Method for Providing Alarms in a Patient Monitor with a Detachable Display FIG. 7 illustrates a flow chart of an example method 700 for providing alarms for a patient monitor that includes a base unit and a detachable user interface unit configured to display hemodynamic monitoring information provided by the base unit. The method 700 can be performed to decide which unit of a patient monitoring system to signal an alarm to ensure patient safety and to provide potentially urgent or critical information to appropriate personnel. For example, if the user interface unit becomes separated from the base unit to the point that wireless communications are no longer established between the two units, the base unit can be configured to indicate an alarm condition without the user interface unit. If, on the other hand, the user interface unit is in communication with the base unit, either wirelessly or wired (e.g., tethered or docked with the base unit), the base unit can be configured to send any alarms to the user interface unit for display. This can advantageously coordinate alarms so that they are signaled on only one unit rather than on both units. In some embodiments of the patient monitors disclosed herein, however, alarms can be configured to be provided on both the base unit and the user interface unit.

In block 705, the base unit monitors incoming patient sensor electrical information for potential alarm conditions. The base unit can also monitor other communication channels, such as a network channel, or analog signal channels, to determine if an alarm, warning, or other alert is to be provided on the patient monitor. For example, the base unit can be configured to calculate one or more hemodynamic parameters from the received information (e.g., from patient sensors and/or external monitor systems). The determined values can be compared to alarm conditions set on the base unit, where the alarm conditions can be automatically calculated, set, or determined and/or manually set.

In block 710, the base unit monitors a wireless signal from the user interface unit. The base unit can be configured to determine whether the user interface unit is still in communication with the base unit. For example, the base unit can send a request for acknowledgement to the user interface unit. If no reply is received within a tailored period of time, then the base unit decides that the user interface is not in communication with the base unit. Other methods of determining wireless connection can be used as well. For example, the user interface unit can be configured to periodically ping the base unit, and if the base unit determines that it has missed one or more pings from the user interface unit, then the base unit can decide that the user interface is not in communication with the base unit.

In block 715, the base unit determines whether an alarm condition exists. An alarm condition exists, for example, if one or more determined hemodynamic parameters, or a combination of parameters, triggers a selected, predetermined, or tailored alarm condition. An alarm condition may also exist where a peripheral device signals an alarm to the patient monitor. An alarm condition may also exist where a hospital communication network initiates an alarm condition through a network connection with the base unit. If no alarm condition exists, then the base unit can return to block 705 to monitor alarm conditions. If an alarm condition exists, then the base unit can proceed to block 720 to determine whether a wireless signal exists between the base unit and the user interface module.

If wireless communications are established and continuing between the base unit and the user interface unit as determined in block 720, then the base unit proceeds to block 730 where the base unit sends the alarm condition(s) to the user interface unit for display. If no wireless communications are currently established, then the base unit proceeds to block 725 to display and/or sound an alarm. For example, the base unit can include a speaker and/or a display or lights to indicate audibly and/or visually that an alarm condition has occurred. In this way, the patient monitor system can be configured to preferably alarm on the user interface unit and to fall back to the base unit where the user interface unit is out of communication with the base unit. This redundancy can ensure that alarms are signaled when they occur, regardless of whether the user interface unit is present in the room, on, or functioning. This can also reduce alarm fatigue, which may occur where users hear multiple alarms and/or frequent alarms to the point where the user begins to ignore the alarms.

In some embodiments, the base unit can be configured to track one or more alarms when the user interface unit is disconnected. Upon re-establishing a connection, the base unit can send the one or more alarms to the user interface unit.

Figure 8:
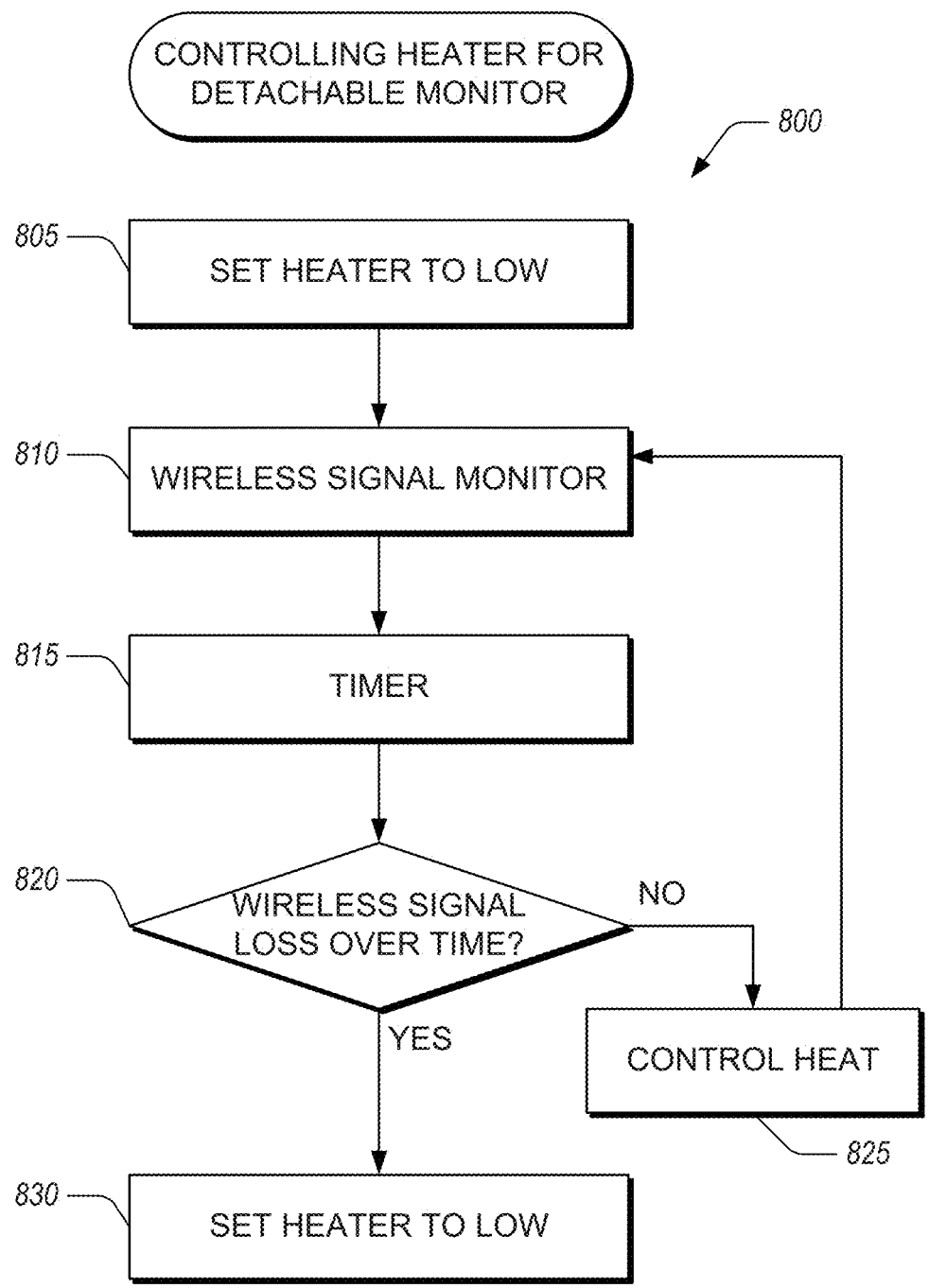
FIG. 8 illustrates a flow chart of an example method for controlling a heater in a patient monitor that includes a base unit and a detachable user interface unit configured to provide user interface elements to control a heater attached to the base unit.

Example Method for Controlling a Heater in a Patient Monitor with a Detachable Display FIG. 8 illustrates a flow chart of an example method 800 for controlling a heater in a patient monitor that includes a base unit and a detachable user interface unit configured to provide user interface elements to control a heater attached to the base unit. The base unit can be configured to control the heater for use, for example, in thermodilution measurements in a patient. It may be desirable, then, to be able to control the heater so as to not cause pain or damage to the patient. In general, the user interface unit is configured to be a command center for the base unit, where the user interface unit is used to provide commands to the base unit to control the heater, for example. If the base unit loses contact with the user interface unit, it can be advantageous to default to a safe condition for the heater to avoid or prevent the heater from causing harm to the patient by, for example, providing too much heat energy in the patient.

In block 805, the patient monitor sets the heater to a low power setting. For example, the low power setting can be less than or equal to about 150 mW, less than or equal to about 200 mW less than or equal to about 300 mW, or less than or equal to about 500 mW. This low power can be clinically safe to the patient even if the heater were to remain at this power for an extended period of time.

In block 810, the base unit monitors a wireless signal from the user interface unit. The base unit can be configured to determine whether the user interface unit is still in communication with the base unit. For example, the base unit can send a request for acknowledgement to the user interface unit. If no reply is received within a tailored period of time, then the base unit decides that the user interface is not in communication with the base unit. Other methods of determining wireless connection can be used as well. For example, the user interface unit can be configured to periodically ping the base unit, and if the base unit determines that it has missed one or more pings from the user interface unit, then the base unit can decide that the user interface is not in communication with the base unit.

In block 815, the base unit monitors a timer to determine the amount of time that the heater has been in a particular state (e.g., at a particular power level) and/or to determine the amount of time since the last wireless communication with the user interface unit.

If wireless communications are established and continuing between the base unit and the user interface unit as determined in block 820, then the base unit proceeds to block 825 to control the heater. To control the heater, the base unit can command the heater to turn on to a high setting (e.g., about 12 W) for a period of time (e.g., about 20 s) followed by turning the heater to a low setting (e.g., about 150 mW) for the same period of time (e.g., about 20 s). The amount of times that the heater is in the high setting and/or the low setting can vary and can be varied during operation to achieve targeted goals. For example, the high setting can comprise providing at least about 8 W of power to the heater, at least about 7.5 W of power to the heater, at least about 10 W of power to the heater, at least about 12 W of power to the heater, or at least about 15 W of power to the heater. The low power setting time can be different from the high power setting. The low power setting or the high power setting can be applied for at least about 10 s, at least about 15 s, at least about 20 s, at least about 30 s, or at least about 60 s.

If wireless communications have been determined to be down for longer than a threshold period of time, as determined in block 820, then the base unit proceeds to block 830 to set the heater to a low setting to reduce the chances of injury to the patient. In addition, the patient monitor can be configured to mark or label data acquired during this period as faulty or bad data. For example, the displayed trends or values on the user interface unit can be displayed with an asterisk, with a particular color, or the like to show that the data is unreliable and/or that there may be a problem with the communication between the user interface unit and the base unit. In some embodiments, the threshold period of time is at least about 40 s, at least about 60 s, at least about 80 s, at least about 100 s, at least about 120 s, or at least about 140 s. In some embodiments, the threshold period of time is at least about 40 s and/or less than about 140 s. In some embodiments, if wireless communications have not been reestablished before the timer indicates the threshold period of time has run, then the heater is set to low. If, however, wireless communications are re-established, then the heater can continue to be controlled in the same manner as before.

Example User Interfaces Displayed by the User Interface Unit

When the patient monitor 110 is initialized, the user interface unit 117 may display a user interface or screen requesting a practitioner or user to identify (e.g., via a touch screen input) whether a new patient is being monitored by the patient monitor 110, whether a previously entered patient (e.g., a current patient) is being monitored by the patient monitor 110, or whether a patient is being transferred to another area of a hospital (e.g., from an operating room to an intensive care unit). If the practitioner identifies that a current patient is being monitored, then the base unit 115 resumes monitoring the patient. If the practitioner identifies that a patient is being transferred, then the base unit 115 may transfer information associated with the patient to another base unit 115 (e.g., a base unit located in the area where the patient is being transferred) via a wired and/or wireless network. Otherwise, if the practitioner identifies that the patient is new, then the user interface unit 117 may display a user interface that allows the practitioner to input via a touch screen or external input device (e.g., a mouse, a keyboard, a stylus, etc.) patient information (e.g., patient ID, gender, height, weight, age, hemodynamic parameter values, etc.).

Once the patient information is entered or the current patient option is selected, the user interface unit 117 can display a main menu from which one of several user interfaces can be accessed. For example, the user interfaces can include various hemodynamic parameter monitoring user interfaces, an arterial waveform setup and calibration user interface, an oximetry calibration user interface, a hemodynamic calculator user interface, and/or a system configuration user interface. The main menu user interface displayed by the user interface unit 117 allows a practitioner to view entered patient information; perform a pre-insertion calibration, light intensity baseline, and/or in vivo calibration of a light intensity signal received from a cable; enter lab results; inspect, zero, and/or calibrate an arterial blood pressure waveform; mark events on a trend plot of hemodynamic parameter values; export hemodynamic parameter values stored in memory of the base unit 115 (e.g., hemodynamic parameter values for a current patient and/or one or more previous patients) via a wireless connection, a base unit 115 port (e.g., a universal serial bus (USB) port), and/or the like; and/or configure the patient monitor 110.

Figure 9:
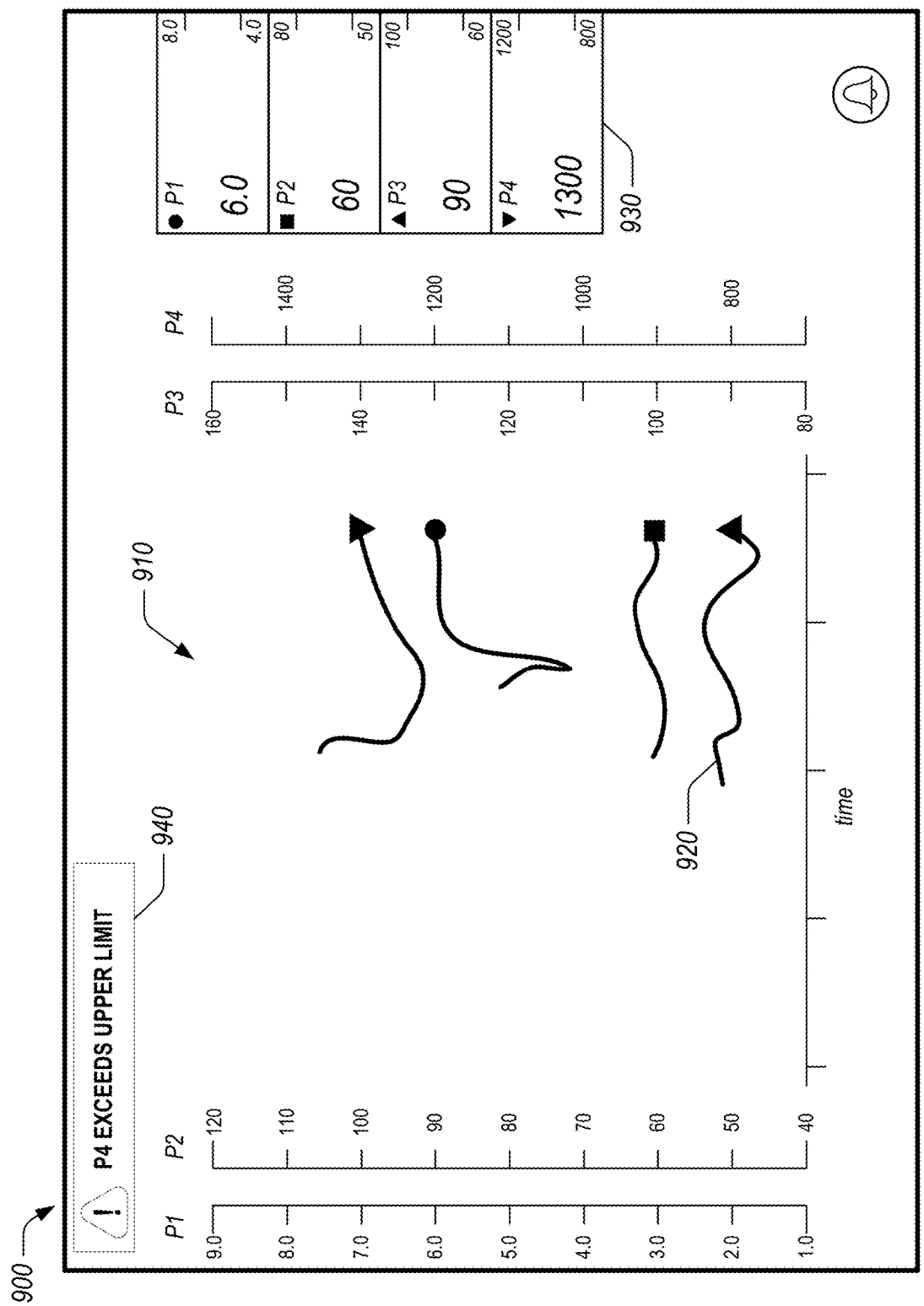
FIG. 9 illustrates an example user interface depicting trend data that is displayed by a user interface unit, such as the user interface unit of FIGS. 1A-1C.

FIG. 9 illustrates an example user interface 900 depicting trend data that is displayed by a user interface unit, such as the user interface unit 117 of FIGS. 1A-1C. The user interface 900 may be generated by the user interface unit 117 and be populated with data determined by the base unit 115. As illustrated in FIG. 9, the user interface 900 displays numerical values and historical trends for one or more hemodynamic parameters (e.g., P1, P2, P3, and P4). While the user interface 900 displays numerical values and historical trends for four hemodynamic parameters, this is not meant to be limiting. The user interface 900 may display numerical values, historical trends, or both numerical values and historical trends for any number of hemodynamic parameters (e.g., 1, 2, 3, 4, 5, 6, 7, etc.).

One or more of the hemodynamic parameters may be associated with a symbol or shape and/or a specific color. For example, hemodynamic parameter P1 is associated with a circle, hemodynamic parameter P2 is associated with a square, hemodynamic parameter P3 is associated with a triangle, hemodynamic parameter P4 is associated with an upside-down triangle, and each of the hemodynamic parameters P1-P4 is associated with a different color. Given that graph 910 depicted in the user interface 900 displays the historical trends for each of the hemodynamic parameters P1-P4, the symbols and/or colors can be used to differentiate between the different historical trends (e.g., the historical trend line can be a color associated with the appropriate hemodynamic parameter and/or the historical trend line can be shaded a color associated with the appropriate hemodynamic parameter).

In an embodiment, the historical trend for a hemodynamic parameter can be temporarily hidden from the user interface 900 via a selection (e.g., a touch screen selection) of the y-axis of the respective hemodynamic parameter. For example, if the practitioner would like to hide historical trend 920, which corresponds with hemodynamic parameter P3, the practitioner can select the y-axis corresponding to hemodynamic parameter P3.

The user interface 900 may also numerically indicate upper and/or lower limits for one or more of the hemodynamic parameters P1-P4. If the value of a hemodynamic parameter P1-P4 falls below a lower limit or exceeds an upper limit, then the base unit 115 may generate an alarm for display in the user interface 900 and/or for output via a speaker. For example, the upper limit for hemodynamic parameter P4 is 1200 and the lower limit for hemodynamic parameter P4 is 800 as shown in box 930. As depicted in FIG. 9, a current value of the hemodynamic parameter P4 is 1300 and thus the hemodynamic parameter P4 exceeds the upper limit. Accordingly, the user interface 900 displays an alarm 940 indicating that the hemodynamic parameter P4 has exceeded the upper limit.

Within the graph 910, a practitioner can pan or scroll through various hemodynamic parameter P1-P4 values. For example, the practitioner can select a pan or scroll mode. Selection of the pan or scroll mode may cause a movable vertical marker to appear in the graph 910. Thus, the vertical marker may correspond with various times depending on the location of the vertical marker. The value for one or more of the hemodynamic parameters P1-P4 that correspond to the time at which the vertical marker is located may be displayed in the graph 910. As the practitioner adjusts the location of the vertical marker (e.g., as the practitioner moves the vertical marker left or right), the hemodynamic parameter P1-P4 values may update accordingly.

Optionally, the user interface unit 117 displays a user interface that provides a practitioner with an option to pause or resume hemodynamic parameter monitoring. Pausing hemodynamic parameter monitoring may cause the user interface unit 117 to stop displaying hemodynamic parameter values and/or may cause the base unit 115 to stop generating alarms or notifications.

In further embodiments, the practitioner can adjust the time scale in the user interface 900 (e.g., the scale of the x-axis of the graph 910) by selecting the x-axis. Adjusting the time scale causes the graph 910 to display additional historical hemodynamic parameter values (e.g., if the time scale is increased) or fewer historical hemodynamic parameter values (e.g., if the time scale is decreased).

Optionally, the practitioner can add events to the graph 910. For example, the user interface unit 117 can generate and display a screen that allows the practitioner to select an event and a time that the event occurred. Events can include blood gas, drug titration, electrosurgical procedure, fluid challenge, miscellaneous, nursing maneuver, respirator/ventilator change, suction, x-ray/radiology, and/or the like. An event can be displayed as a vertical line or other symbol in the graph 910 at a time that the event occurred. The vertical line or symbol may be marked with another symbol or character that identifies the type of event that occurred at the time.

Figure 10:
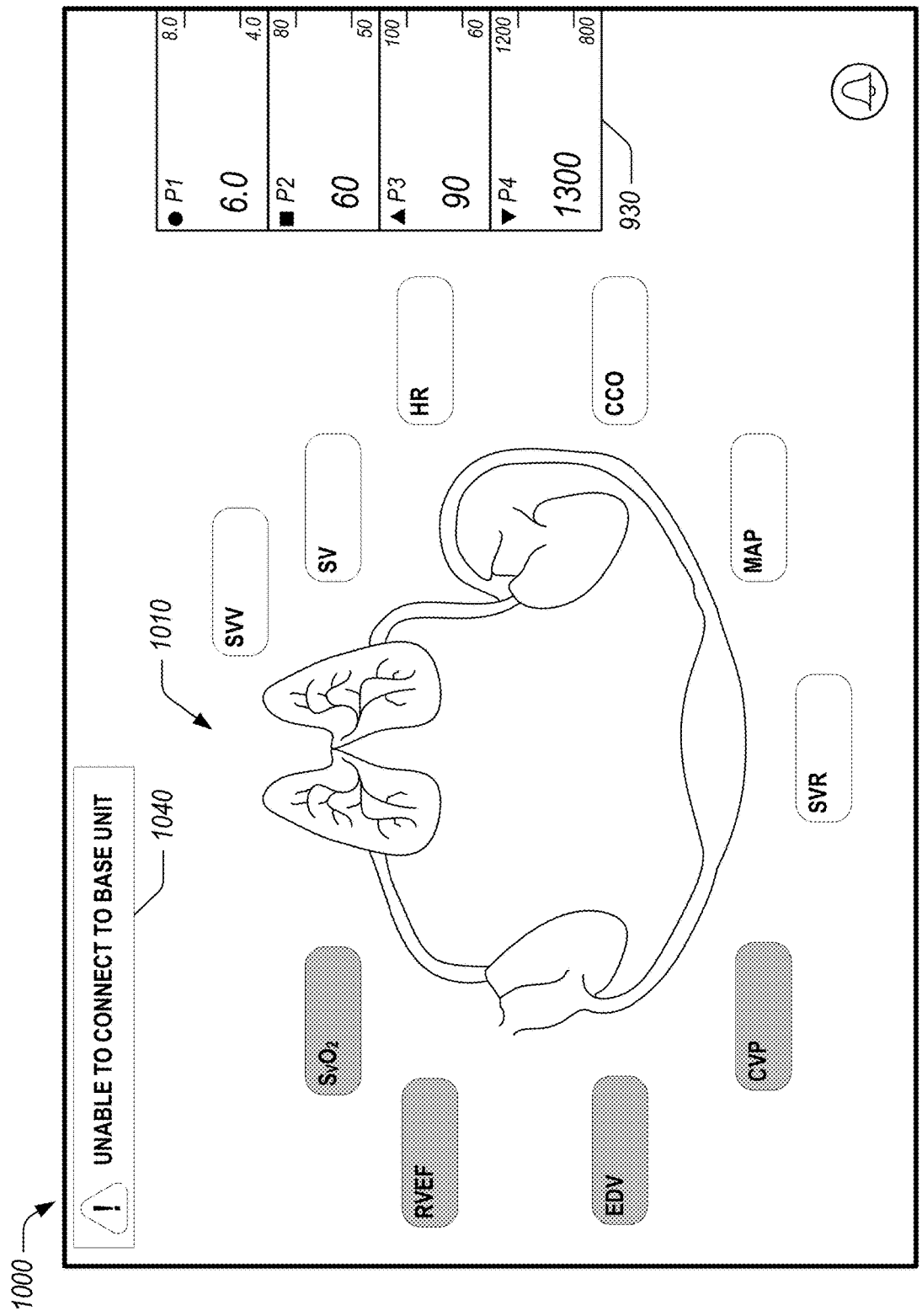
FIG. 10 illustrates an example user interface depicting a physiological schematic 1010 that is displayed by a user interface unit, such as the user interface unit of FIGS. 1A-1C.

FIG. 10 illustrates an example user interface 1000 depicting a physiological schematic 1010 that is displayed by a user interface unit, such as the user interface unit 117 of FIGS. 1A-1C. The user interface 1000 may be generated by the user interface unit 117 and be populated with data determined by the base unit 115. As illustrated in FIG. 10, the physiological schematic 1010 is of the circulatory loop. However, this is not meant to be limiting. The physiological schematic 1010 may be at least a portion of any physiological system in the human body.

One or more hemodynamic parameters may be indicated at various locations within the physiological schematic 1010. For example, the indicated hemodynamic parameters can include stroke volume variation (SVV), SV, heart rate (HR), CCO, mean arterial pressure (MAP), systemic vascular resistance (SVR), central venous pressure (CVP), end-diastolic volume (EDV), right ventricular ejection fraction (RVEF), mixed venous oxygen saturation ($SvO_2$), and/or other such parameters. Hemodynamic parameters for which live values are available can be lightly shaded (e.g., SVV, SV, HR, CCO, MAP, and SVR) and hemodynamic parameters for which no live values are available can be darkly shaded (e.g., CVP, EDV, RVEF, and $SvO_2$).

As described above with respect to FIGS. 7 and 8, the base unit 115 and/or the user interface unit 117 can periodically communicate with each other to determine whether a connection between the two units is still active. If, for example, the user interface unit 117 is not able to communicate with the base unit 115, the user interface unit 117 can generate and display a notification 1040 in the user interface 1000 indicating that the user interface unit 117 cannot connect to the base unit 115.

Figure 11:
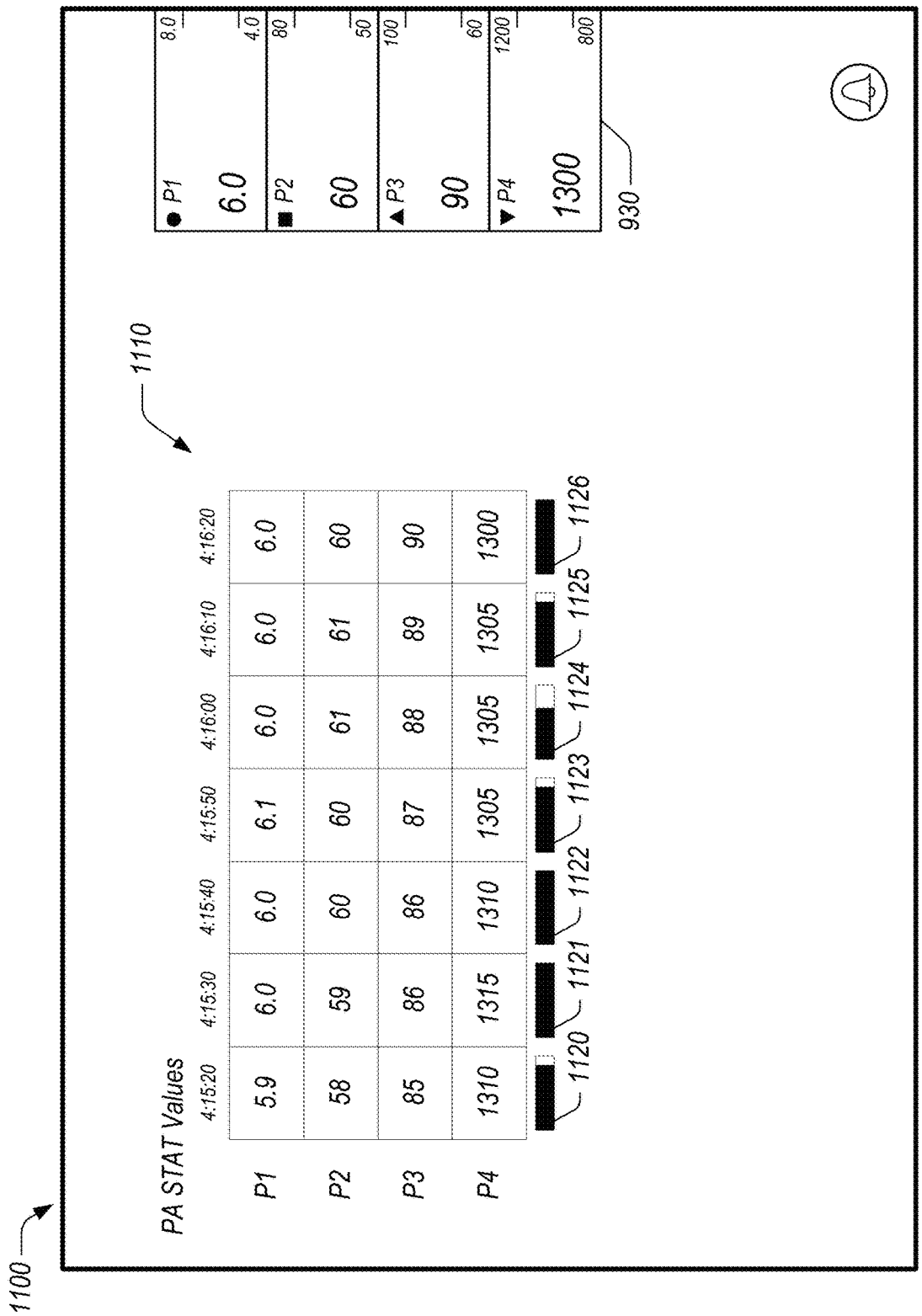
FIG. 11 illustrates an example user interface depicting a hemodynamic parameter value matrix that is displayed by a user interface unit, such as the user interface unit of FIGS. 1A-1C.

FIG. 11 illustrates an example user interface 1100 depicting a hemodynamic parameter value matrix 1110 that is displayed by a user interface unit, such as the user interface unit 117 of FIGS. 1A-1C. As illustrated in FIG. 11, the user interface 1100 displays numerical hemodynamic parameter values for one or more hemodynamic parameters over a period of time in the hemodynamic parameter value matrix 1110. While the hemodynamic parameter value matrix 1110 includes hemodynamic parameter values for hemodynamic parameters P1-P4, this is not meant to be limiting. The hemodynamic parameter value matrix 1100 can include hemodynamic parameter values for any number of hemodynamic parameters over any length of time.

Below the hemodynamic parameter value matrix 1110 are bars 1120-1126 that indicate the signal quality of the wireless or wired connection between the base unit 115 and the user interface unit 117 over the period of time identified in the hemodynamic parameter value matrix 1110. For example, the length of the darkly shaded bar in the bars 1120-1126 indicates the signal quality level.

In an embodiment, the base unit 115 may determine one or more hemodynamic parameter values in time intervals shorter than the time intervals between entries in the hemodynamic value matrix 1110. For example, the base unit 115 may determine values for hemodynamic parameter P1 every second. The hemodynamic parameter value matrix 1110, however, displays a value for hemodynamic parameter P1 every 10 seconds. Thus, the base unit 115 can aggregate the determined values that fall within each time interval of the hemodynamic parameter value matrix 1110 (e.g., determine an average the 10 values that fall within each 10 second time interval, determine a medium of the 10 values that fall within each 10 second time interval, determine a mode of the 10 values that fall within each 10 second time interval, etc.) and transmit the aggregate value to the user interface unit 117 for display in the hemodynamic parameter value matrix 1110.

Figure 12:
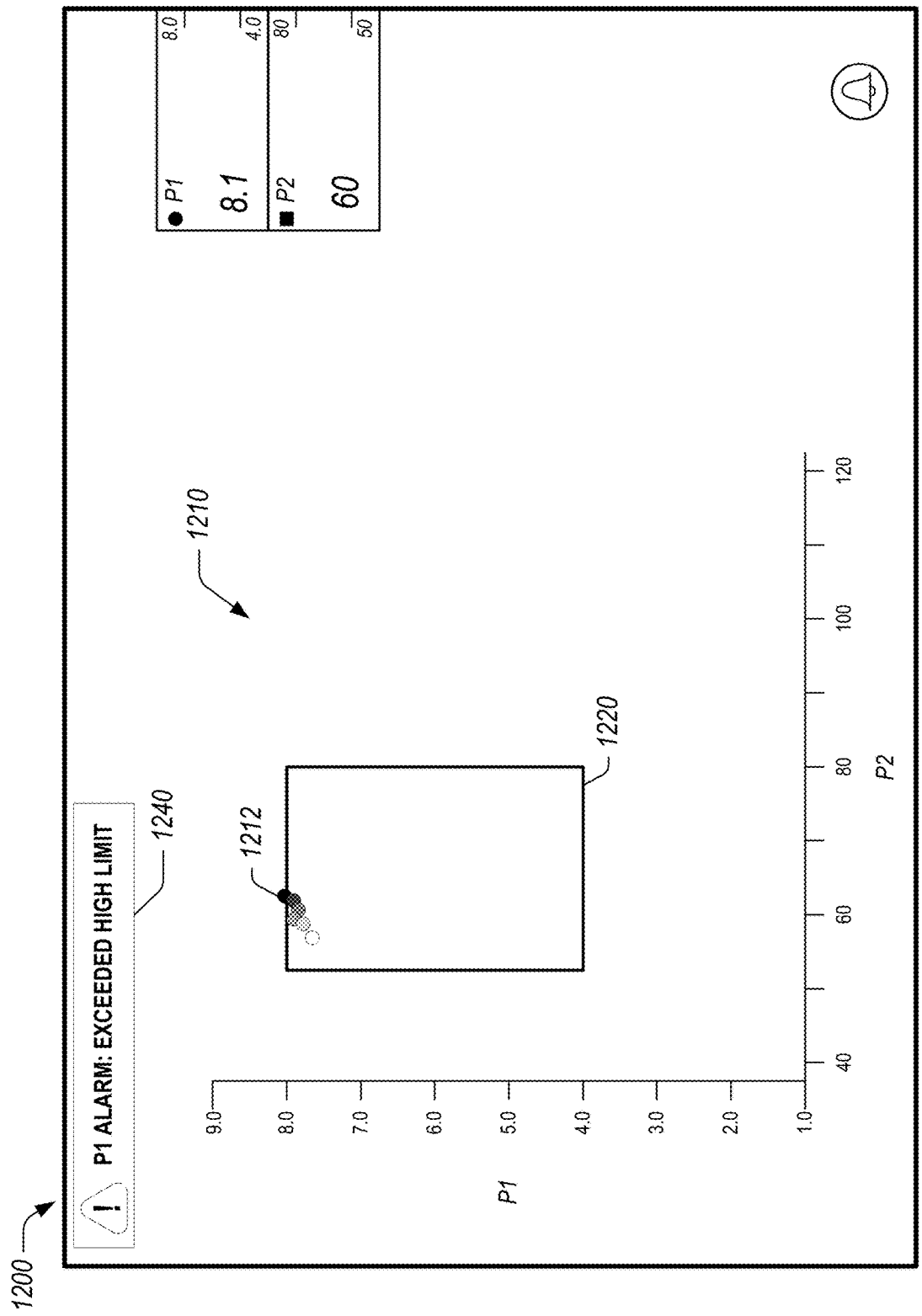
FIG. 12 illustrates an example user interface depicting a bi-variant plot that is displayed by a user interface unit, such as the user interface unit of FIGS. 1A-1C.

FIG. 12 illustrates an example user interface 1200 depicting a bi-variant plot 1210 that is displayed by a user interface unit, such as the user interface unit 117 of FIGS. 1A-1C. As illustrated in FIG. 12, the user interface 1200 displays the bi-variant plot 1210 that plots the values of one hemodynamic parameter (e.g., P1) against the values of another hemodynamic parameter (e.g., P2). The bi-variant plot 1210 may include shaded symbols (e.g., symbol 1212) that represent the plotted values of the two hemodynamic parameters over a period of time. The shading of the symbol may indicate newer and older plotted values. For example, darker shaded symbols may be newer than lighter shaded symbols. As new plotted values are determined by the base unit 115 for display, previous symbols may become lighter to indicate their respective age.

The bi-variant plot 1210 may also depict an optimal range represented by a shape, such as rectangle 1220 (or a circle, square, trapezoid, etc.). If the plotted values fall outside the optimal range, then the base unit 115 may generate a notification 1240 for display. A practitioner can set the limits that define the optimal range and the limits may only affect the bi-variant plot 1210 or may determine when the base unit 115 generates an alarm or notification. In some embodiments, the alarm limits (e.g., limits that, if exceeded, cause the base unit 115 to generate a notification) and the optimal range limits can be the same or different. The notification 1240 may indicate which of the hemodynamic parameter values caused the plotted value to fall outside the optimal range and/or a reason why the hemodynamic parameter value caused the plotted value to fall outside the optimal range. For example, as shown in FIG. 12, symbol 1212 falls outside the rectangle 1220. The notification 1240 indicates that the value for hemodynamic parameter P1 caused the plotted value to fall outside the optimal range because the value exceeded a high limit.

In an embodiment, the user interface unit 117 generates and displays a user interface that allows a practitioner to configure a catheter and injectate volume to be used when performing Bolus CO measurements (e.g., set a catheter type, an injectate volume, an injectate temperature, a type of injectate probe, etc.). Some settings, such as injectate temperature and injectate probe type, may be automatically determined by the base unit 115.

Figure 13:
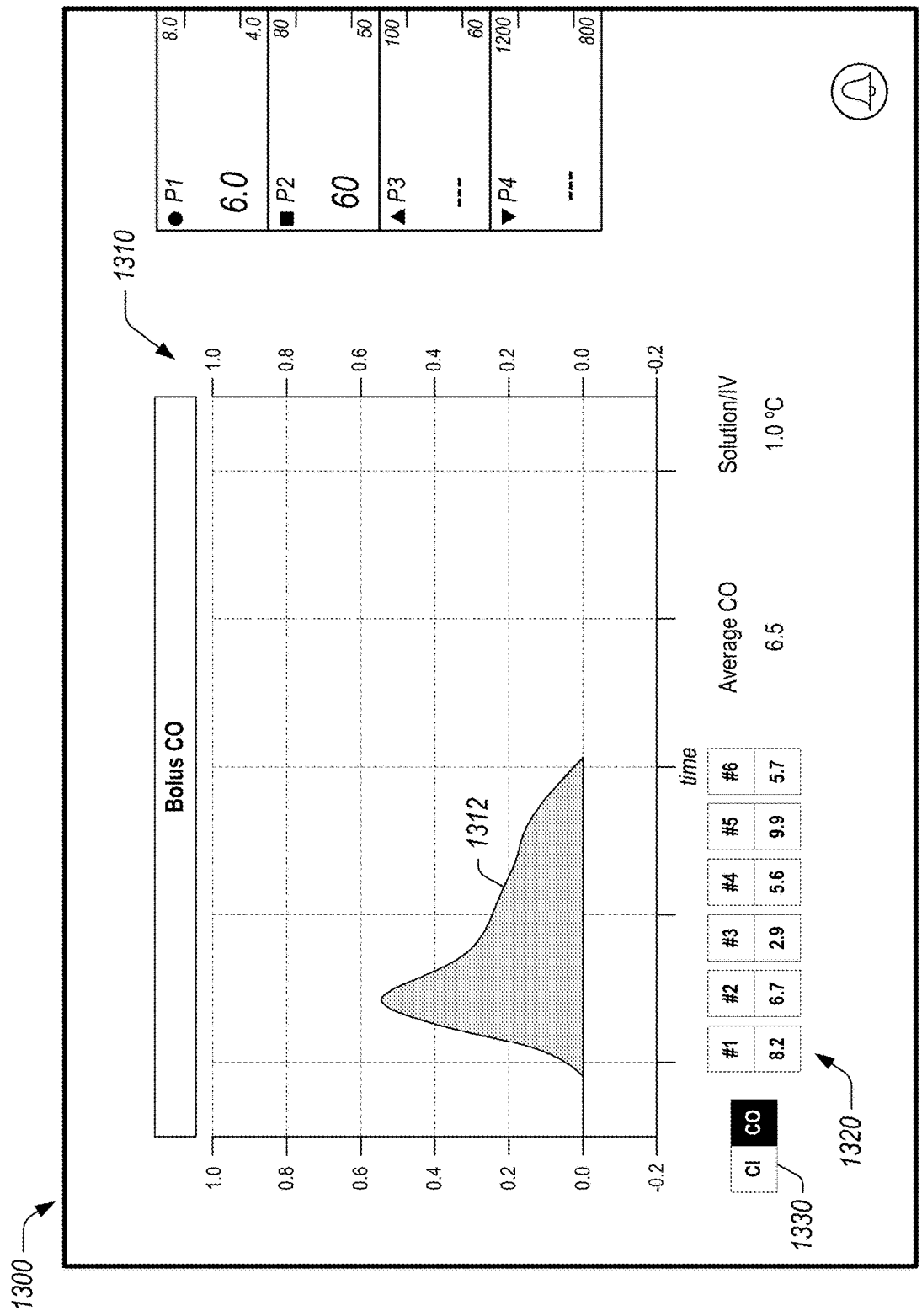
FIG. 13 illustrates an example user interface depicting a Bolus CO graph that is displayed by a user interface unit, such as the user interface unit of FIGS. 1A-1C.

Once the settings are determined, the user interface unit 117 can display a Bolus CO measurement user interface. FIG. 13 illustrates an example user interface 1300 depicting a Bolus CO graph 1310 that is displayed by a user interface unit, such as the user interface unit 117 of FIGS. 1A-1C. As illustrated in FIG. 13, the Bolus CO graph 1310 includes a Bolus curve 1312 that indicates a Bolus CO level over a period of time. When the base unit 115 is initialized, the user interface 1300 can display a start button (not shown) that, when selected, causes the Bolus curve 1312 to begin displaying in the Bolus CO graph 1310. As the start button is selected, the user interface 1300 begins to plot one or more Bolus curves (e.g., 4, 5, 6, 7, etc.), such as the Bolus curve 1312, automatically. The practitioner may select a stop or pause button to stop the automatic plotting of the Bolus curves.

As Bolus CO values are determined by the base unit 115, the determined Bolus CO values are displayed below the Bolus CO graph 1310 under the corresponding curve number in boxes 1320. A practitioner can select button 1330 to cause the boxes 1320 to instead display Bolus cardiac index (CI) values that are also determined by the base unit 115. The user interface 1300 can also display an average Bolus CO (or average Bolus CI) and/or a solution/IV temperature below the Bolus CO graph 1310.

In some embodiments, not shown, the user interface 1300 can numerically display current and/or historical Bolus CO and/or CI values. Along with the current and/or historical Bolus CO and/or CI values, the user interface 1300 can display the Bolus volume at different times.

Figure 14:
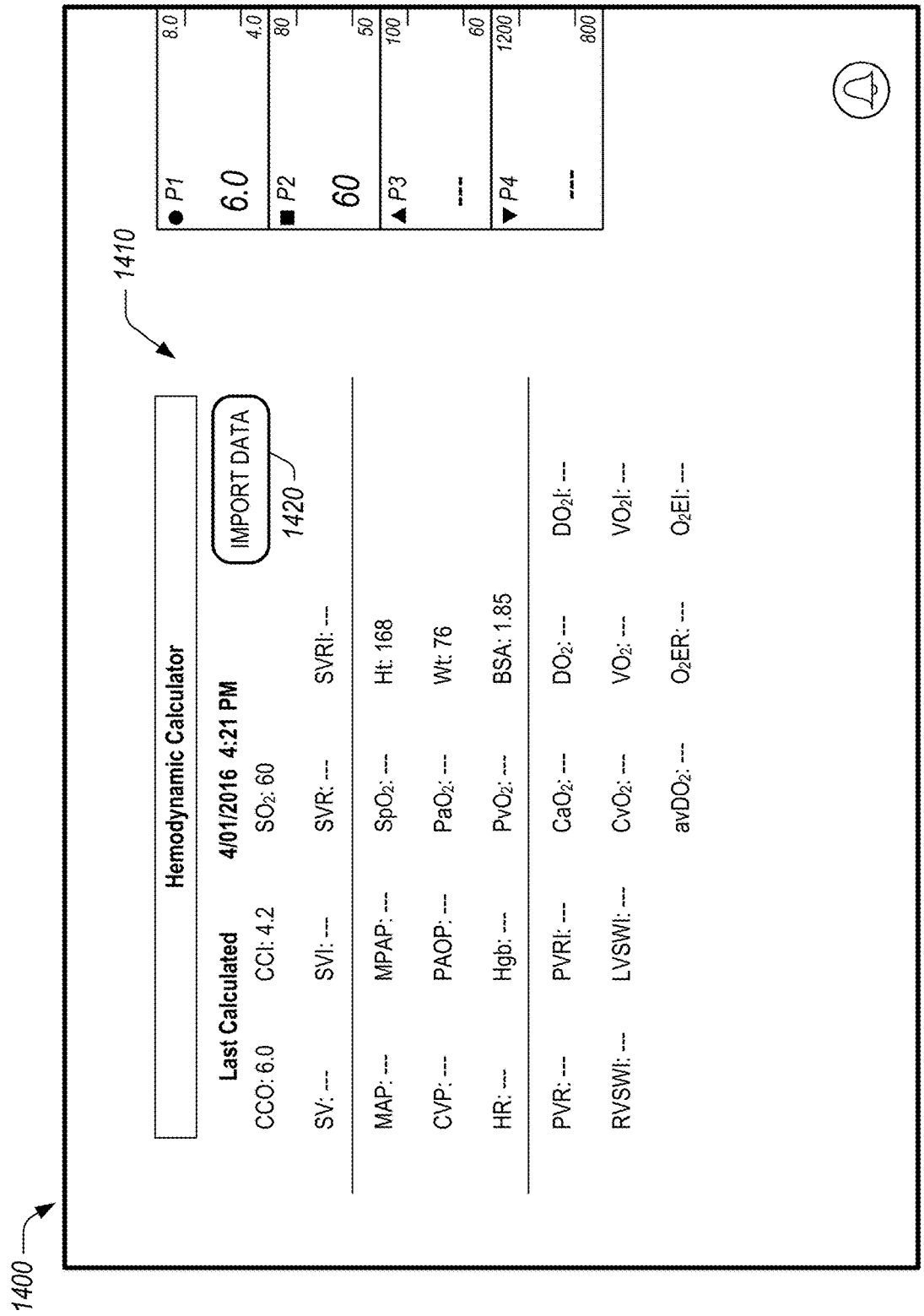
FIG. 14 illustrates an example user interface depicting a hemodynamic calculator that is displayed by a user interface unit, such as the user interface unit of FIGS. 1A-1C.

FIG. 14 illustrates an example user interface 1400 depicting a hemodynamic calculator 1410 that is displayed by a user interface unit, such as the user interface unit 117 of FIGS. 1A-1C. The hemodynamic calculator 1410 allows a practitioner to understand the adjustments in various input parameters that may be necessary to achieve targeted output parameter values. Patient information, such as height and weight, can be imported from the patient information settings or manually entered, and such information along with imported hemodynamic parameter values (e.g., as determined by the base unit 115) or manually entered hemodynamic parameter values can be used by the base unit 115 to determine associated hemodynamic output parameters.

As illustrated in FIG. 14, the hemodynamic calculator 1410 is divided into three horizontal sections. The top and middle sections include input parameters for which values can be entered or imported (e.g., via import button 1420) and adjusted. Such input parameters can include CCO, continuous cardiac index (CCI), oxygen saturation ($SO_2$), SV, stroke volume index (SVI), SVR, systemic vascular resistance index (SVRI), MAP, mean pulmonary artery pressure (MPAP), arterial oxygen saturation ($S_pO_2$), height, CVP, pulmonary artery occlusion pressure (PAOP), partial pressure of oxygen in arterial blood ($PaO_2$), HR, Hemoglobin (Hgb), mixed venous oxygen tension ($PvO_2$), and/or body surface area (BSA). The lowest section includes output parameters determined by the base unit 115 based on the input parameters in the top and middle sections. Such output parameters can include pulmonary vascular resistance (PVR), pulmonary vascular resistance index (PVRI), arterial oxygen content ($CaO_2$), oxygen delivery ($DO_2$), oxygen delivery index ($DO_2I$), right ventricular stroke work index (RVSWI), left ventricular stroke work index (LVSWI), mixed venous oxygen content ($CvO_2$), oxygen volume ($VO_2$), oxygen volume index ($VO_2I$), arterio-jugular differences of oxygen (avDO$_2$), oxygen extraction ratio (O$_2$ER), and/or oxygen extraction index (O$_2$EI).

When a practitioner navigates to the user interface 1400, current patient information (e.g., determined hemodynamic parameter values and/or patient information like weight and height) may be automatically imported for use as input parameters. Input parameter values can be manually entered (either via the user interface unit 117 or by selecting import button 1420) and/or changed by selecting a parameter in the hemodynamic calculator 1410. A marking, such as an asterisk, may appear next to an input parameter that has a value that has been manually entered. The date and/or time of the latest update may be displayed at the top of the hemodynamic calculator 1410.

Base Unit and User Interface Unit Pairing Process

In an embodiment, the base unit 115 and the user interface unit 117 implement a pairing process such that the user interface unit 117 can display data generated by the base unit 115 and/or any one user interface unit 117 can display data generated by a specific base unit 115 (in situations, for example, in which multiple patient monitors 110 are present). FIGS. 15 through 25 describe the pairing process in more detail below.

Figure 15:
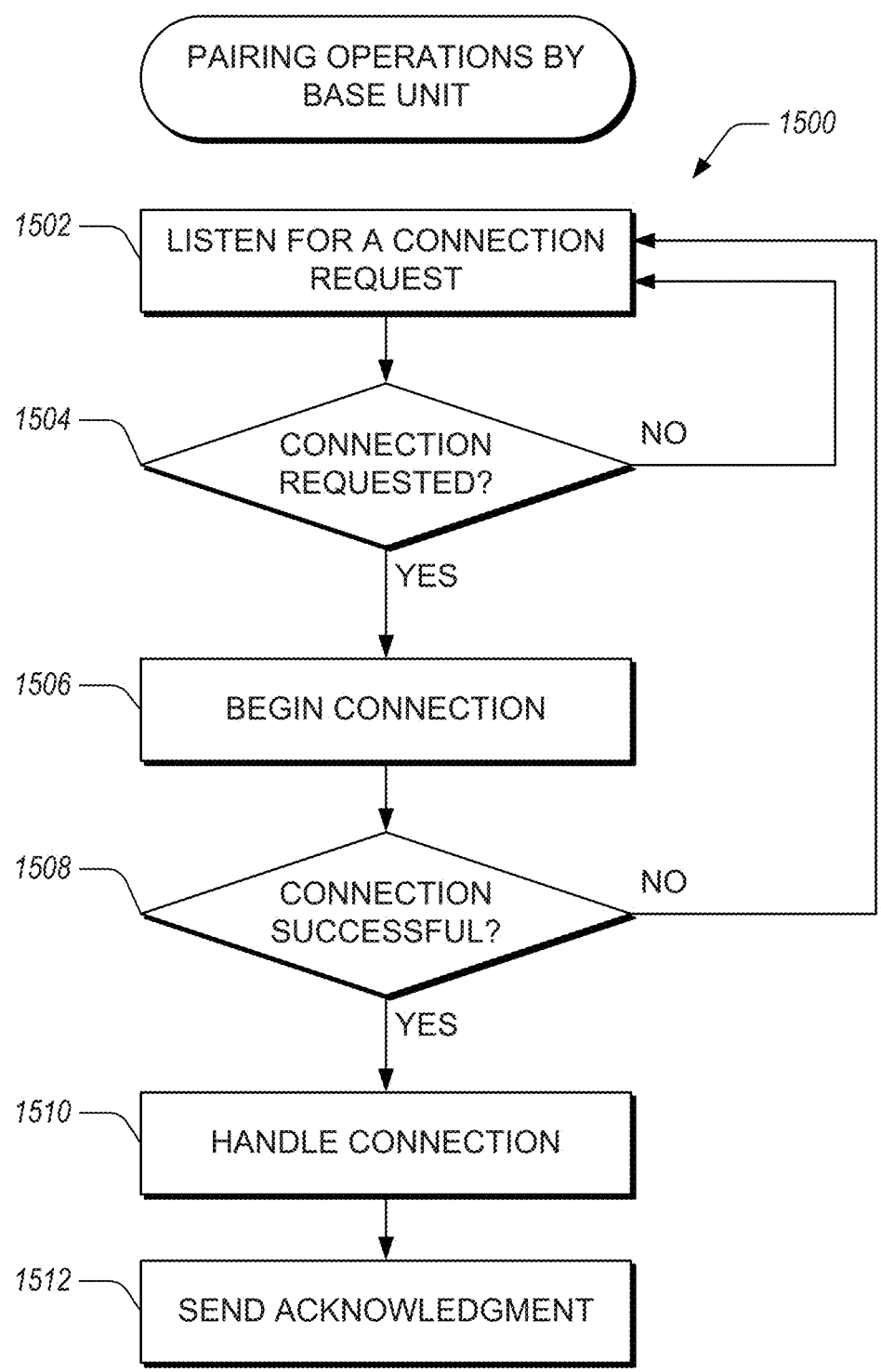
FIG. 15 illustrates a flow chart of an example method for pairing a base unit with a user interface unit.

FIG. 15 illustrates a flow chart of an example method 1500 for pairing a base unit with a user interface unit. In an embodiment, the method 1500 is implemented by a first thread executed by a processor housed in the base unit 115. For example, the first thread, and thus the method 1500, may be initiated at startup of the base unit 115. The first thread may be referred to as an IpServer thread. While the method 1500 depicts several steps, this is not meant to be limiting. Method 1500 may include fewer or more steps than depicted in FIG. 15. The method 1500 begins at block 1502.

At block 1502, the base unit may enter a listening state, waiting for the user interface unit to request a connection. The user interface unit may transmit a connection request to the base unit at some time after the user interface unit starts up. For example, the user interface unit 117 may transmit a connection request at startup or after being disconnected from the base unit. In some embodiments, the user interface unit 117 broadcasts the connection request using a wired or wireless transmission protocol, such as the user datagram protocol (UDP).

At block 1504, the base unit determines whether a connection has been requested by a user interface unit. If a connection has not been requested, then the method 1500 reverts back to block 1502 and the base unit returns to the listening state to wait for another connection request. Otherwise, if a connection has been requested, then the method 1500 proceeds to block 1506.

At block 1506, the base unit begins attempts to connect with the user interface unit. In some embodiments, the connection attempt includes the base unit and/or the user interface unit transmitting authentication, association, and/or other like messages to each other using a wired or wireless transmission protocol, such as transmission control protocol (TCP).

At bock 1508, the base unit determines whether a connection is successfully established with the user interface unit. If the attempt to connect with the user interface unit fails, then the method 1500 reverts back to block 1502 and the base unit returns to the listening state to wait for another connection request. Otherwise, if the connection attempt succeeds, then the method 1500 proceeds to block 1510.

At block 1510, the base unit can set up send and/or receive message handlers and/or various other connection listeners. The send and/or receive message handlers and/or the various other connection listeners may allow the base unit to transmit data to, receive data from, and/or process data received from the user interface unit.

At block 1512, the base unit transmits an acknowledgement message to the user interface unit confirming that the connection attempt succeeded. After transmitting the acknowledgement message, the executing thread may transmit a message to one or more applications executing on the base unit indicating that the base unit has successfully paired with the user interface unit.

Figure 16A:
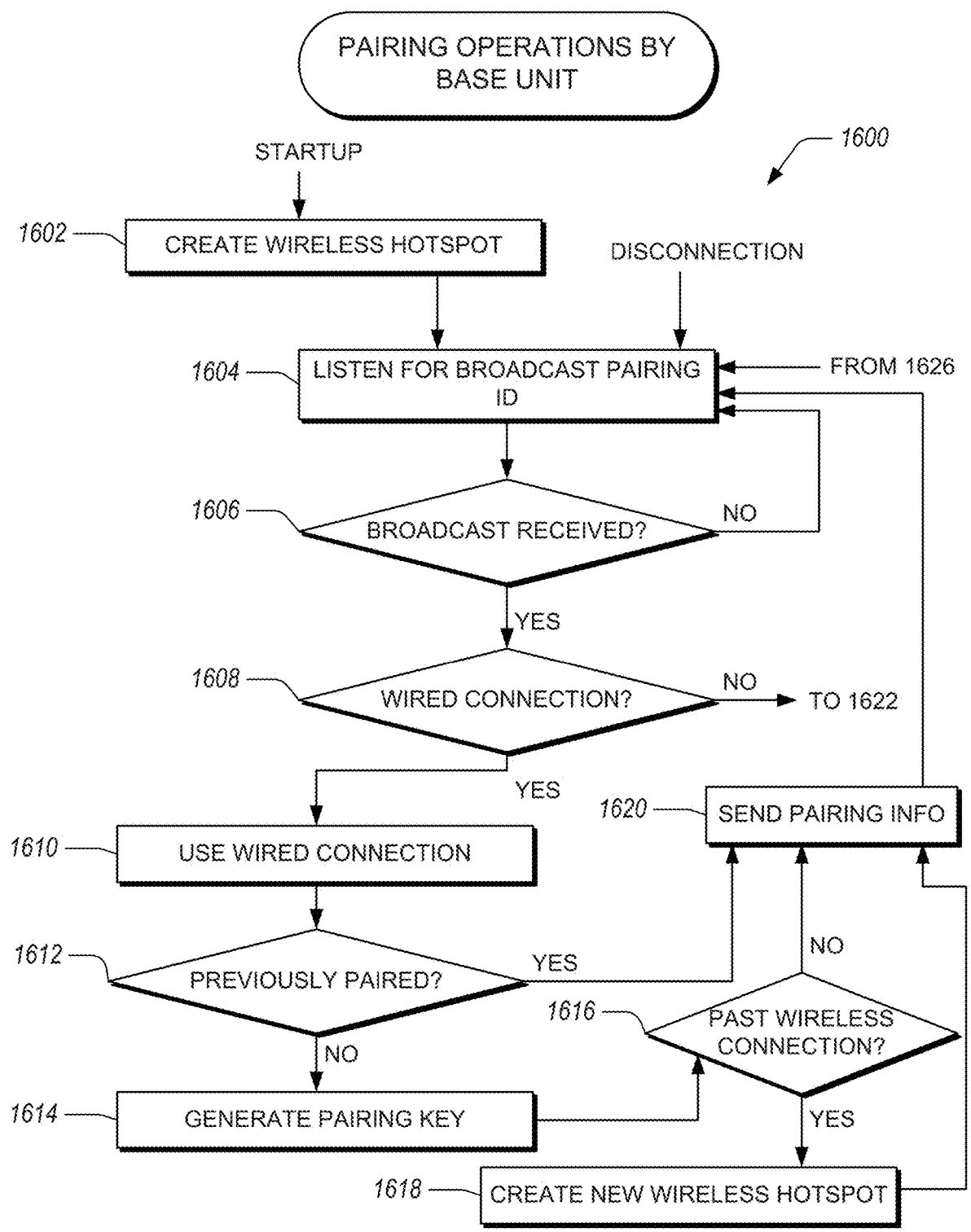
FIGS. 16A-16B illustrate another flow chart of an example method for pairing a base unit with a user interface unit.
Figure 16B:
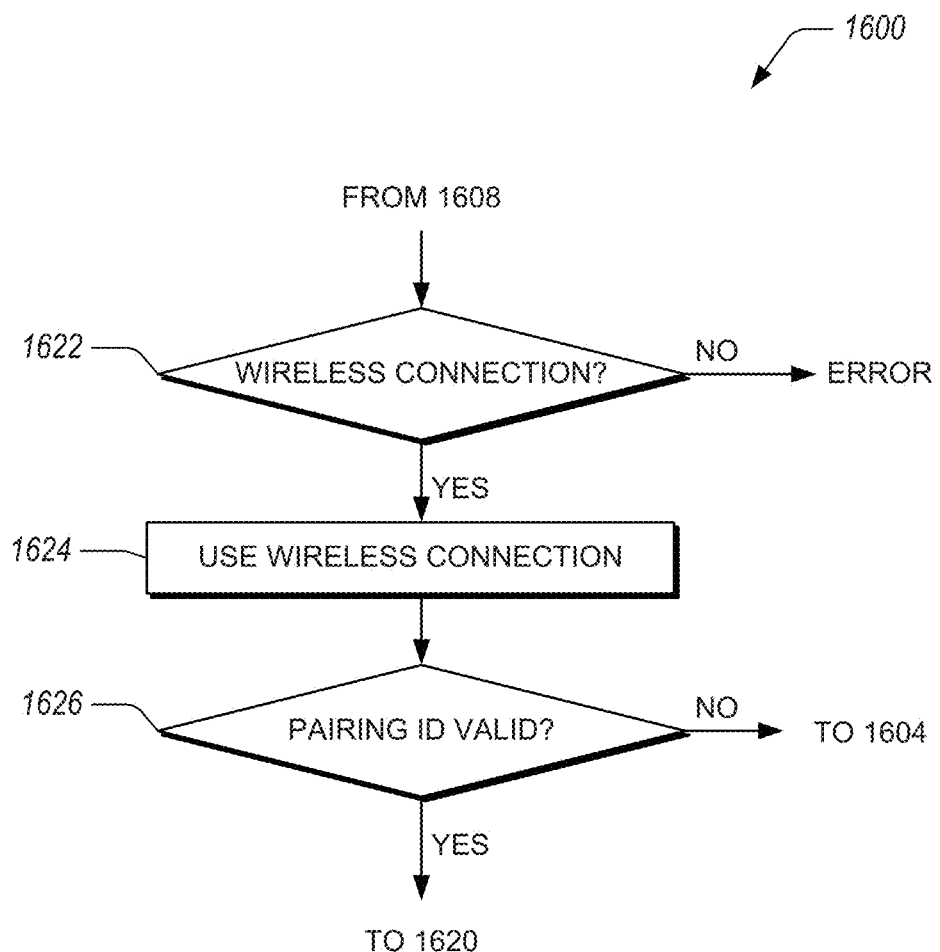

FIGS. 16A-16B illustrate another flow chart of an example method 1600 for pairing a base unit with a user interface unit. In an embodiment, the method 1600 is implemented by a second thread executed by a processor housed in the base unit 115. For example, the second thread, and thus the method 1600, may be started and/or stopped by the first thread based on a connection or disconnection of the user interface unit 117 from the base unit 115. The second thread may be referred to as a PairingReceiver thread. While the method 1600 depicts several steps, this is not meant to be limiting. Method 1600 may include fewer or more steps than depicted in FIGS. 16A-16B. The method 1600 begins at block 1602.

At block 1602, the base unit creates a wireless hotspot (e.g., WIFI, BLUETOOTH, etc.) at startup of the base unit. The wireless hotspot may be created to allow the user interface unit to connect to the wireless hotspot. A name of the hotspot may be determined by a service set identifier (SSID) listed in a configuration file stored on the base unit or may be auto-generated if a SSID is not stored. Whether creation of the hotspot succeeds or fails, the method 1600 proceeds to block 1604 (e.g., because a wireless connection may not be necessary for the base unit and the user interface unit to communicate).

At block 1604, the base unit starts listening for a broadcast pairing ID. The base unit may start listening for the broadcast pairing ID after a wireless hotspot is created upon startup or after the user interface unit is disconnected from the base unit.

At block 1606, the base unit determines whether a broadcast pairing ID transmitted by a user interface unit is detected. If a broadcast pairing ID is not detected, then the method 1600 reverts back to block 1604 and the base unit continues to listen for a broadcast pairing ID. Otherwise, if a broadcast pairing ID is detected, then the method 1600 proceeds to block 1608 and the base unit determines whether wired (e.g., local area network (LAN) created via Ethernet or another cable) or wireless communications should be used to establish the connection with the user interface unit. In some embodiments, a wired connection source takes priority over a wireless connection source if both are available.

At block 1608, the base unit determines whether a wired connection source exists. If a wired connection source exists, then the method 1600 proceeds to block 1610. Otherwise, if a wired connection source does not exist, then the method 1600 proceeds to block 1622.

At block 1610, the base unit uses the wired connection source to establish the connection with the user interface unit. After block 1610 is complete, the method 1600 proceeds to block 1612.

At block 1612, the base unit determines whether the base unit and the user interface unit were previously paired. For example, the base unit and the user interface unit may have previously paired if the pairing key of the user interface unit matches the pairing key of the base unit. The pairing key of the user interface unit may have been included in or be equivalent to the transmitted broadcast pairing ID. If the base unit and the user interface unit were previously paired, then the method 1600 proceeds to block 1620. Otherwise, if the base unit and the user interface unit were not previously paired, then the method 1600 proceeds to block 1614.

At block 1614, the base unit generates a new pairing key for eventual transmission to the user interface unit. For example, the new pairing key can be a guaranteed unique ID. After block 1614 is complete, the method 1600 proceeds to block 1616.

At block 1616, the base unit determines whether the base unit was previously wirelessly connected to a user interface unit. If the base unit was previously wirelessly connected to a user interface unit, then the method 1600 proceeds to block 1618. Otherwise, if the base unit was not previously wirelessly connected to a user interface unit, then the method 1600 proceeds to block 1620.

At block 1618, the base unit creates a new wireless hotspot. The base unit may create a new wireless hotspot to disallow a previously connected user interface unit from communicating with the base unit.

At block 1620, the base unit transmits pairing information to the user interface unit. The pairing information can include the pairing key (e.g., a previous pairing key or the new pairing key generated at block 1614), the hotspot SSID, a version of the base unit, a wired address of the base unit if a wired connection source is available (e.g., a LAN internet protocol (IP) address), and/or a wireless address of the base unit if a wireless connection source is available (e.g., a wireless IP address). After block 1620 is complete, the method 1600 reverts back to block 1604 and the base unit continues to listen for a broadcast pairing ID.

At block 1622, the base unit determines whether a wireless connection source is available. If a wireless connection source is not available, then an error may have occurred. Otherwise, if a wireless connection source is available, then the method 1600 proceeds to block 1624.

At block 1624, the base unit uses the wireless connection source to establish a connection with the user interface unit. After block 1624 is complete, the method 1600 proceeds to block 1626.

At block 1626, the base unit determines whether the pairing key of the user interface unit matches the pairing key of the base unit. If the pairing keys do not match, then the method 1600 reverts back to block 1604 and the base unit continues to listen for a broadcast pairing ID. Otherwise, if the pairing keys do match, then the method 1600 proceeds to block 1620.

Figure 17A:
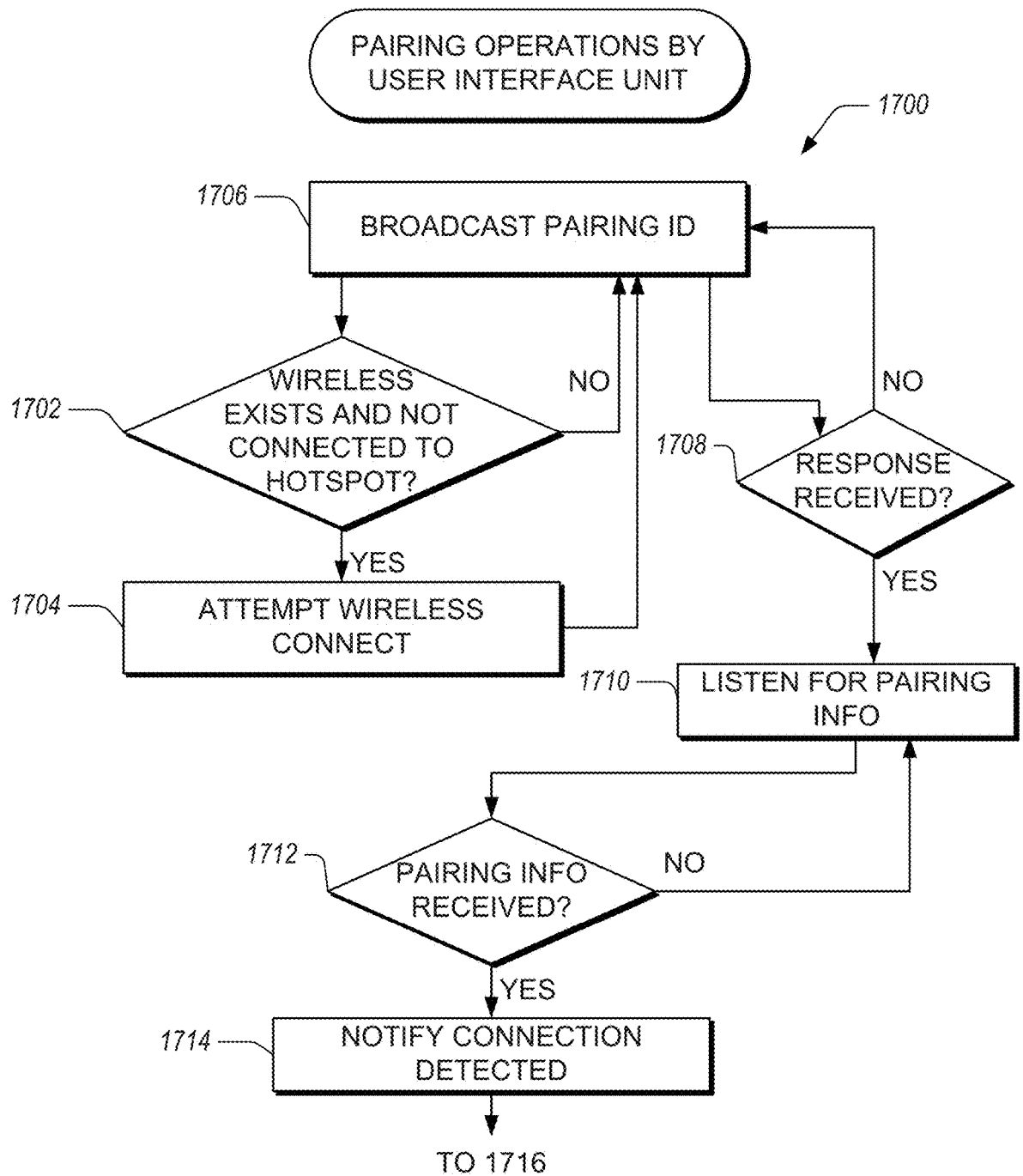
FIGS. 17A-17B illustrate another flow chart of an example method for pairing a base unit with a user interface unit.
Figure 17B:
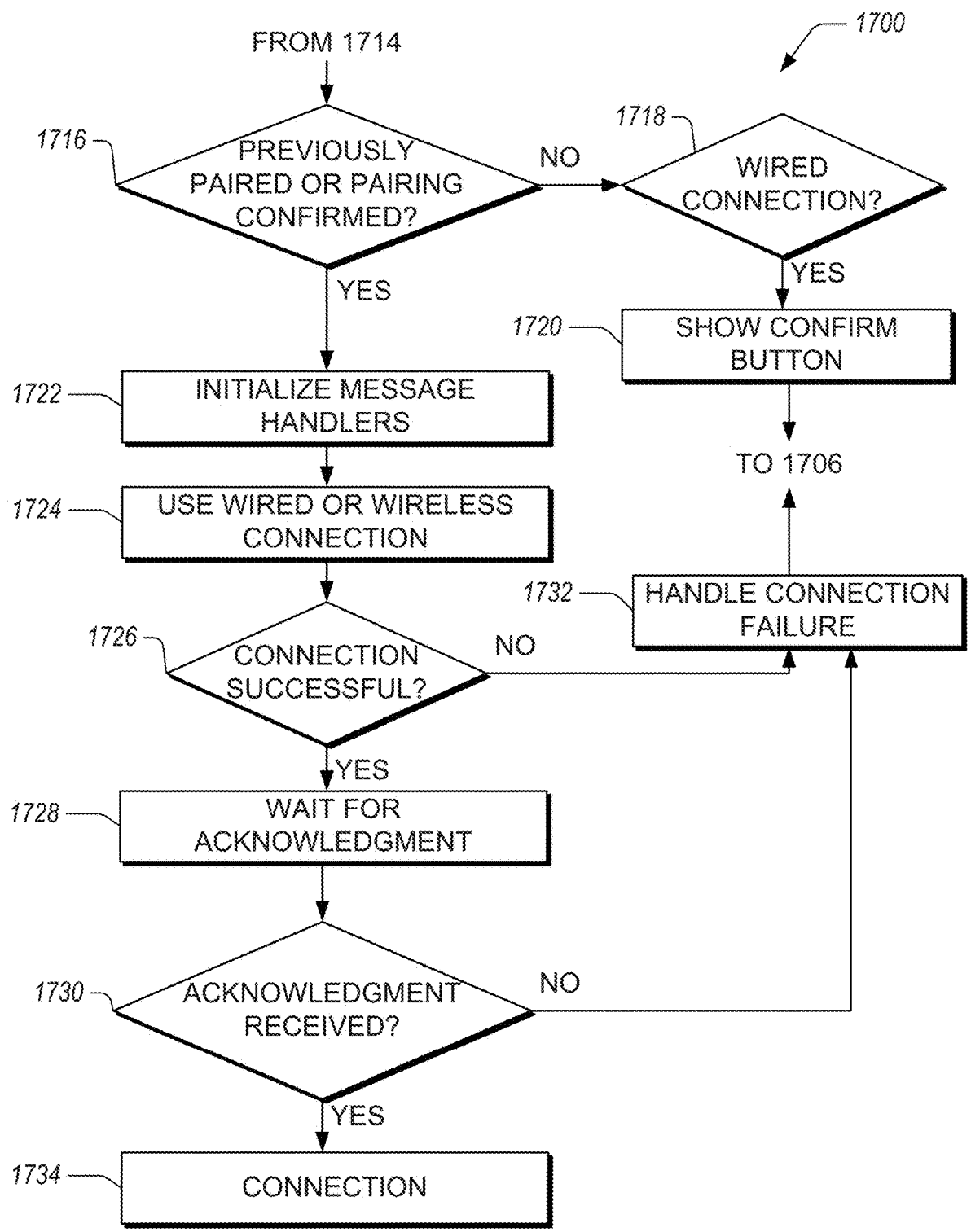

FIGS. 17A-17B illustrate another flow chart of an example method 1700 for pairing a base unit with a user interface unit. In an embodiment, the method 1700 is implemented by a first thread executed by a processor housed in the user interface unit 117. For example, the first thread, and thus the method 1700, may be initiated based on the connection or disconnection of the user interface unit 117 from the base unit 115. While the method 1700 depicts several steps, this is not meant to be limiting. Method 1700 may include fewer or more steps than depicted in FIGS. 17A-17B. The method 1700 begins at block 1702.

At block 1702, the user interface unit determines whether a valid wireless hotspot exists and whether the user interface is not currently connected to a wireless hotspot. The user interface unit may make this determination after startup of the user interface unit or after a network disconnection (e.g., a disconnection from the base unit). If a valid wireless hotspot exists and the user interface unit is not currently connected to a wireless hotspot, then the method 1700 proceeds to block 1704. Otherwise, the method 1700 proceeds to block 1706.

At block 1704, the user interface unit attempts to connect to the wireless hotspot. After block 1704 is complete, the method 1700 proceeds to block 1706.

At block 1706, the user interface unit broadcast a pairing ID. The user interface unit may broadcast the pairing ID over all available connections (e.g., wired and wireless connections).

At block 1708, the user interface unit determines whether a broadcast response is received from the base unit. For example, the broadcast response may be an acknowledgment that the broadcasted pairing ID was received. If a broadcast response is not received, the method 1700 reverts back to block 1706 and the user interface unit continues to broadcast the pairing ID. Otherwise, if a broadcast response is received, the method 1700 proceeds to block 1710.

At block 1710, the user interface unit starts listening for pairing information transmitted by the base unit. If no pairing information has been received after a threshold period of time (e.g., a timeout period, such as 5 seconds or any like time period) expires, then the method 1700 reverts back to block 1706 and the user interface unit again broadcasts the pairing ID.

At block 1712, the user interface unit determines whether the pairing information is received from the base unit before the threshold period of time expires. If the pairing information is not received and the threshold period of time has not expired, then the method 1700 reverts back to block 1710 and the user interface unit continues to listen for the pairing information. If the pairing information is received before the threshold period of time expires, then the method 1700 proceeds to block 1714.

At block 1714, the user interface unit notifies other threads or applications executed by the processor housed in the user interface unit that a base unit has been found and a connection attempt should be made. After block 1714 is complete, the method 1600 proceeds to block 1716.

At block 1716, the user interface unit determines whether the user interface unit previously paired with the base unit or whether a pairing with the base unit has been confirmed (e.g., by selection of a confirm button by a user). For example, the user interface may determine whether the user interface unit has previously paired with the base unit by comparing the pairing key of the user interface unit with the pairing key of the base unit received as part of the pairing information. The user interface unit and the base unit previously paired if the pairing keys match. If the user interface unit and the base unit were not previously paired and a pairing has not been confirmed, then the method 1700 proceeds to block 1718. Otherwise, if the user interface unit and the base unit were previously paired or a pairing has been confirmed, then the method 1700 proceeds to block 1722.

At block 1718, the user interface unit determines whether a wired connection source is available. If a wired connection source is not available, then the user interface unit does not proceed with a connection and the method 1700 may revert back to block 1702 or 1706. Otherwise, if a wired connection source is available, then the method 1700 proceeds to block 1720.

At block 1720, the user interface unit displays a confirm button. The user can select the confirm button to verify that the user interface unit and the base unit should pair. After block 1720 is complete, the method 1700 either proceeds to block 1722 (e.g., if the confirm button is selected before a timeout period, such as 5 seconds or any like time period) or reverts back to block 1706 and the user interface unit can broadcast the pairing ID to ensure that the base unit remains available for pairing while the user interface unit waits for the user to select the confirm button. If the confirm button is selected after the timeout period, the user interface unit may complete blocks 1706 through 1714 again before proceeding to block 1722 because the pairing has been confirmed.

At block 1722, the user interface unit initializes send and/or receive message handlers to handle communications transmitted to or received from the base unit. After block 1722 is complete, the method 1700 proceeds to block 1724.

At block 1724, the user interface unit decides whether to use a wired connection source or a wireless connection source. In some embodiments, a wired connection source supersedes a wireless connection source such that the user interface unit uses the wired connection source to establish a connection with the base unit if both a wired and wireless connection source are available.

At block 1726, the user interface unit attempts to connect with the base unit using the chosen connection source and determines whether a connection with the base unit is successful. If the connection with the base unit is unsuccessful, then the method 1700 proceeds to block 1732. Otherwise, if the connection with the base unit is successful, then the method 1700 proceeds to block 1728.

At block 1728, the user interface unit waits for an acknowledgment to be transmitted by the base unit. The user interface unit may wait for a timeout period, such as 7 seconds (or any other like time period). A connection may not be considered complete until the acknowledgement is received.

At block 1730, the user interface unit determines whether the acknowledgement has been received from the base unit. If the acknowledgment has not been received or has not been received before the timeout period expires, then the method 1700 proceeds to block 1732. Otherwise, if the acknowledgment has been received (e.g., before the timeout period expires), then the method 1700 proceeds to block 1734.

At block 1732, the user interface unit handles a connection failure. After block 1732 is complete, the method 1700 reverts to block 1706 and the user interface unit starts over by broadcasting the pairing ID.

At block 1734, the user interface unit confirms that a connection with the base unit is established. The user interface unit may then begin displaying data received from the base unit.

Figure 18:
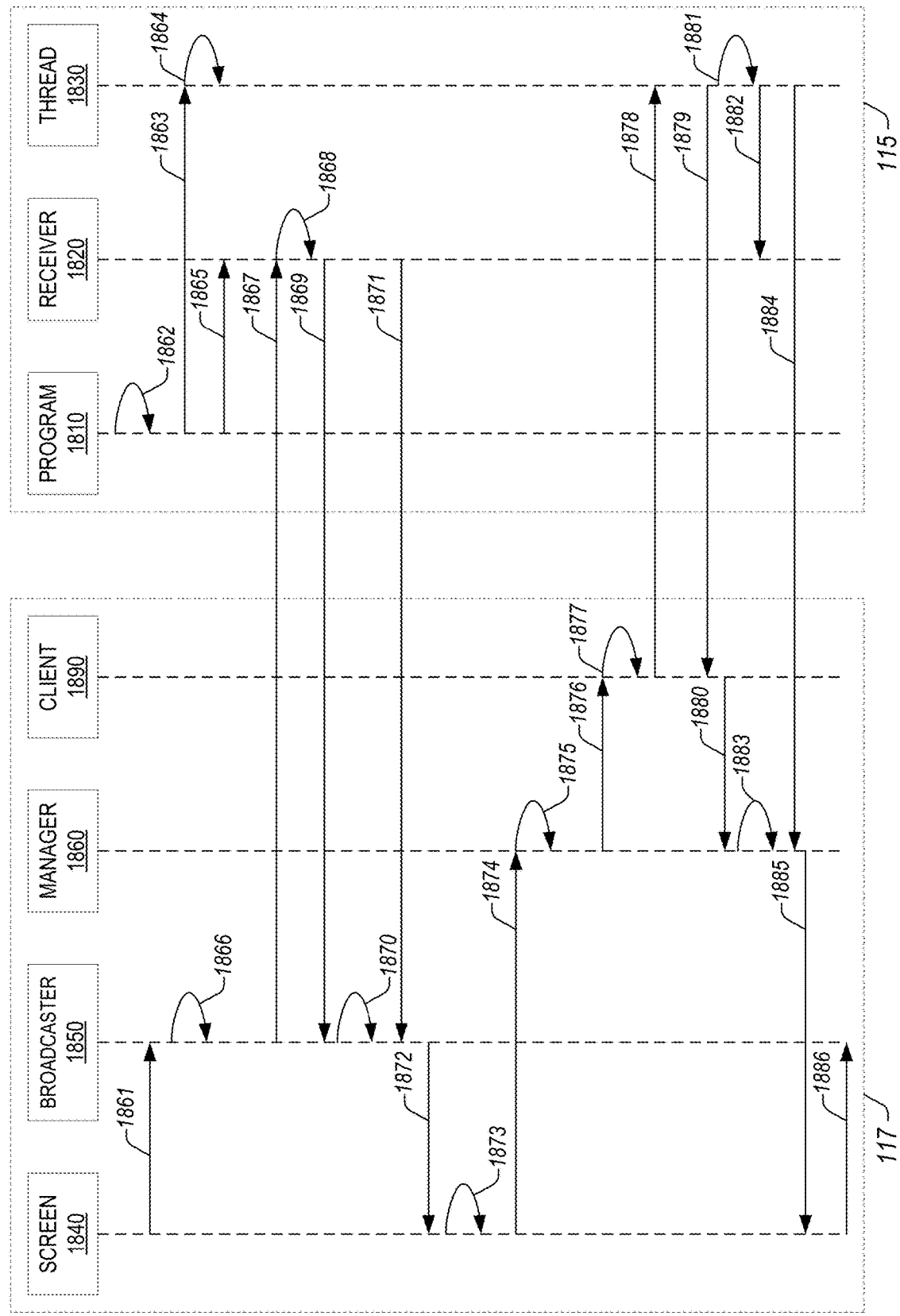
FIG. 18 illustrates a sequence diagram depicting a chronological order of events executed by the base unit and the user interface unit when the user interface unit is connected to the base unit over a wired connection source and attempts to pair with the base unit for the first time.

FIG. 18 illustrates a sequence diagram depicting a chronological order of events executed by the base unit 115 and the user interface unit 117 when the user interface unit 117 is connected to the base unit 115 over a wired connection source and attempts to pair with the base unit 115 for the first time. As illustrated in FIG. 18, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

At startup, such as when the user interface unit 117 is turned on, the screen 1840 may display a pairing screen. The screen 1840 may then instruct the broadcaster 1850 to listen and broadcast a pairing ID at 1861. Similarly, at startup, such as when the base unit 115 is turned on, the program 1810 may launch a wireless host so as to create a wireless hotspot at 1862. The program 1810 may then instruct the thread 1830 to start listening for a broadcast pairing ID at 1863. Receipt of the instruction may cause the thread 1830 to create a listener (e.g., a TCP listener) at 1864. The program 1810 may also instruct the receiver 1820 to start listening for a broadcast pairing ID at 1865.

The broadcaster 1850 may attempt to connect to the wireless hotspot at 1866. After some time, the broadcaster 1850 may also transmit the pairing ID at 1867. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection.

After receiving the pairing ID, the receiver 1820 can determine whether to use a wired or wireless connection source at 1868 as described above. Here, the receiver 1820 selected the wired connection source. Once this is determined, the receiver 1820 can transmit a response over the wired connection source acknowledging that the pairing ID was received and/or indicating that the base unit 115 is attempting a connection at 1869.

The broadcaster 1850 can then begin to listen for the pairing information at 1870. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 1871. At 1872, the broadcaster 1850 notifies the screen 1840 that a connection is detected, which causes the screen 1840 to start a connection detected function that causes the screen 1840 to display the pairing information at 1873. In addition, the screen 1840 may display the confirm button. The broadcaster 1850 may continue to broadcast the pairing ID until the confirm button is selected to ensure that the base unit 115 is still available for a connection. Once the confirm button is selected, then the screen 1840 notifies the manager 1860 at 1874 and the manager 1860 initializes the send and/or receive message handlers at 1875.

The manager 1860 then notifies the client 1890 that the message handlers are initialized at 1876 and the client 1890 determines whether to use a wired or wireless connection source at 1877. Here, the client 1890 uses the wired connection source. After the determination is made, the client 1890 transmits a connection request over the wired connection source to the thread 1830 at 1878. At 1879, the thread 1830 sends a message to the client 1890 accepting the connection. The client 1890 then notifies the manager 1860 of the connection acceptance at 1880. Before or after message 1880, the thread 1830 initializes send and/or receive message handlers to handle the connection at 1881 and instructs the receiver 1820 to stop listening for pairing IDs at 1882. After receiving the connection acceptance at 1880, the manager 1860 starts listening for the acknowledgment message at 1883. At 1884, the thread 1830 transmits the acknowledgment message to the manager 1860. This may cause the manager 1860 to transmit a notification to the screen 1840 that the connection is successful at 1885. The screen 1840 may then instruct the broadcaster 1850 to stop broadcasting the pairing ID at 1886.

Figure 19:
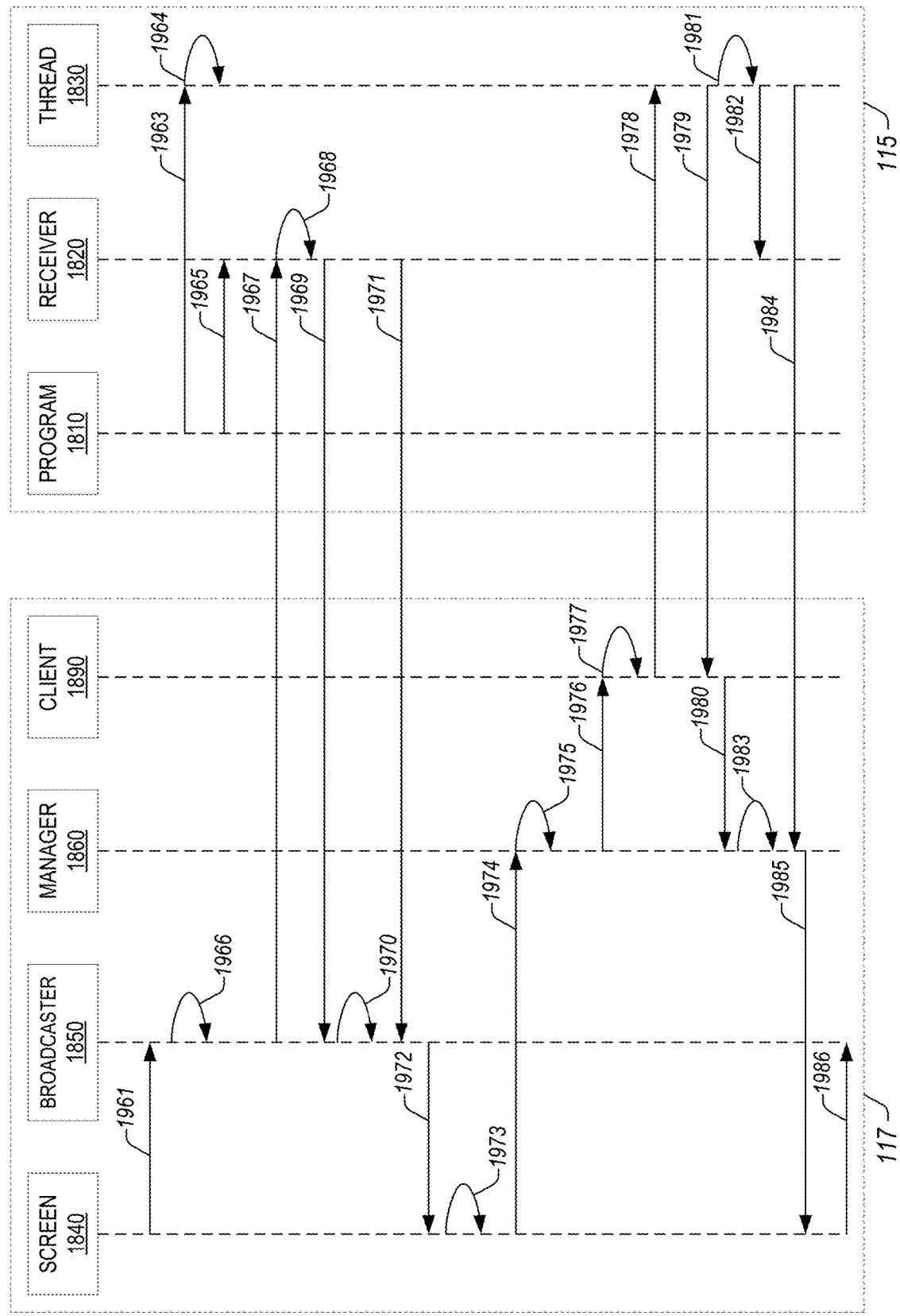
FIG. 19 illustrates a sequence diagram depicting a chronological order of events executed by the base unit and the user interface unit when the user interface unit is connected to the base unit over a wired connection source and attempts to re-pair with the base unit.

FIG. 19 illustrates a sequence diagram depicting a chronological order of events executed by the base unit 115 and the user interface unit 117 when the user interface unit 117 is connected to the base unit 115 over a wired connection source and attempts to re-pair with the base unit 115. As illustrated in FIG. 19, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the screen 1840 may instruct the broadcaster 1850 (e.g., on any screen) to listen and broadcast a pairing ID at 1961. Similarly, after the user interface unit 117 is removed from a dock or tether connecting the user interface unit 117 with the base unit 115, the program 1810 may instruct the thread 1830 to start listening for a broadcast pairing ID at 1963. Receipt of the instruction may cause the thread 1830 to create a listener (e.g., a TCP listener) at 1964. The program 1810 may also instruct the receiver 1820 to start listening for a broadcast pairing ID at 1965.

The broadcaster 1850 may attempt to connect to the wireless hotspot at 1966. After some time, the broadcaster 1850 may also transmit the pairing ID at 1967. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection.

After receiving the pairing ID, the receiver 1820 can determine whether to use a wired or wireless connection source at 1968 as described above. Here, the receiver 1820 selected the wired connection source. Once this is determined, the receiver 1820 can transmit a response over the wired connection source acknowledging that the pairing ID was received and/or indicating that the base unit 115 is attempting a connection at 1969.

The broadcaster 1850 can then begin to listen for the pairing information at 1970. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 1971. At 1972, the broadcaster 1850 notifies the screen 1840 that a connection is detected, which causes the screen 1840 to start a connection detected function at 1973. The screen 1840 then notifies the manager 1860 at 1974 to connect and the manager 1860 initializes the send and/or receive message handlers at 1975.

The manager 1860 then notifies the client 1890 that the message handlers are initialized at 1976 and the client 1890 determines whether to use a wired or wireless connection source at 1977. Here, the client 1890 uses the wired connection source. After the determination is made, the client 1890 transmits a connection request over the wired connection source to the thread 1830 at 1978. At 1979, the thread 1830 sends a message to the client 1890 accepting the connection. The client 1890 then notifies the manager 1860 of the connection acceptance at 1980. Before or after message 1980, the thread 1830 initializes send and/or receive message handlers to handle the connection at 1981 and instructs the receiver 1820 to stop listening for pairing IDs at 1982. After receiving the connection acceptance at 1980, the manager 1860 starts listening for the acknowledgment message at 1983. At 1984, the thread 1830 transmits the acknowledgment message to the manager 1860. This may cause the manager 1860 to transmit a notification to the screen 1840 that the connection is successful at 1985. The screen 1840 may then instruct the broadcaster 1850 to stop broadcasting the pairing ID at 1986.

Figure 20:
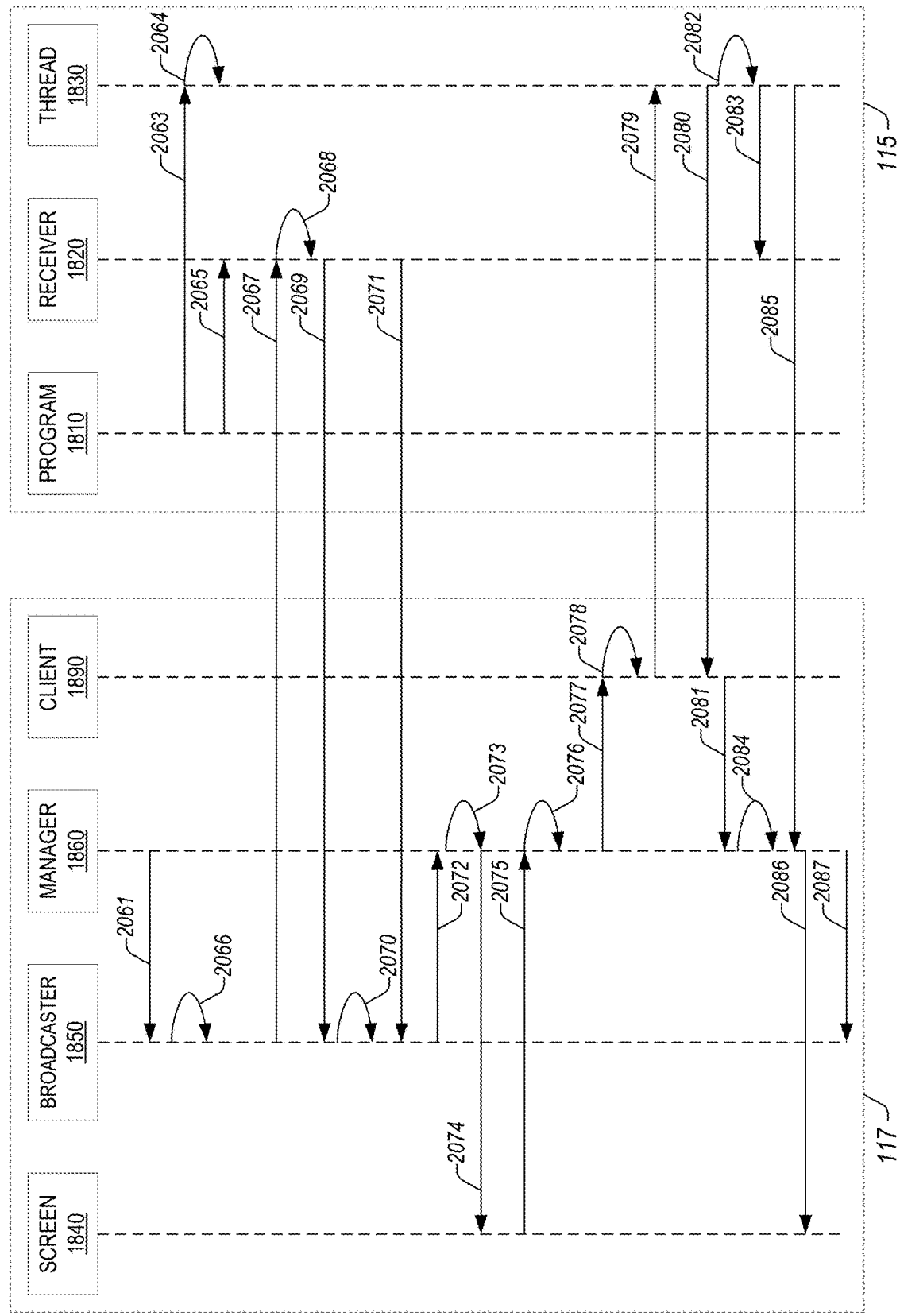
FIG. 20 illustrates a sequence diagram depicting a chronological order of events executed by the base unit and the user interface unit when the user interface unit is connected to the base unit over a wired connection source and is a new user interface unit reconnecting with the base unit.

FIG. 20 illustrates a sequence diagram depicting a chronological order of events executed by the base unit 115 and the user interface unit 117 when the user interface unit 117 is connected to the base unit 115 over a wired connection source and is a new user interface unit reconnecting with the base unit 115. As illustrated in FIG. 20, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the manager 1860 may instruct the broadcaster 1850 to listen and broadcast a pairing ID at 2061. Similarly, after the user interface unit 117 is removed from a dock or tether connecting the user interface unit 117 with the base unit 115, the program 1810 may instruct the thread 1830 to start listening for a broadcast pairing ID at 2063. Receipt of the instruction may cause the thread 1830 to create a listener (e.g., a TCP listener) at 2064. The program 1810 may also instruct the receiver 1820 to start listening for a broadcast pairing ID at 2065.

The broadcaster 1850 may attempt to connect to the wireless hotspot at 2066. After some time, the broadcaster 1850 may also transmit the pairing ID at 2067. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection.

After receiving the pairing ID, the receiver 1820 can determine whether to use a wired or wireless connection source at 2068 as described above. Here, the receiver 1820 selected the wired connection source. Once this is determined, the receiver 1820 can transmit a response over the wired connection source acknowledging that the pairing ID was received and/or indicating that the base unit 115 is attempting a connection at 2069.

The broadcaster 1850 can then begin to listen for the pairing information at 2070. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2071. At 2072, the broadcaster 1850 notifies the manager 1860 that a connection is detected, which causes the manager 1860 to start a connection detected function at 2073. The manager 1860 then instructs the screen 1840 to show the pairing screen at 2074, where the pairing screen includes the confirm button. Once the confirm button is selected, the screen 1840 notifies the manager 1860 accordingly at 2075.

Selection of the confirm button causes the manager 1860 at 2076 to connect and initialize the send and/or receive message handlers.

The manager 1860 then notifies the client 1890 that the message handlers are initialized at 2077 and the client 1890 determines whether to use a wired or wireless connection source at 2078. Here, the client 1890 uses the wired connection source. After the determination is made, the client 1890 transmits a connection request over the wired connection source to the thread 1830 at 2079. At 2080, the thread 1830 sends a message to the client 1890 accepting the connection. The client 1890 then notifies the manager 1860 of the connection acceptance at 2081. Before or after message 2081, the thread 1830 initializes send and/or receive message handlers to handle the connection at 2082 and instructs the receiver 1820 to stop listening for pairing IDs at 2083. After receiving the connection acceptance at 2081, the manager 1860 starts listening for the acknowledgment message at 2084. At 2085, the thread 1830 transmits the acknowledgment message to the manager 1860. This may cause the manager 1860 to transmit an instruction to the screen 1840 to close the pairing screen at 2086 and an instruction to the broadcaster 1850 to stop broadcasting the pairing ID at 2087.

Figure 21:
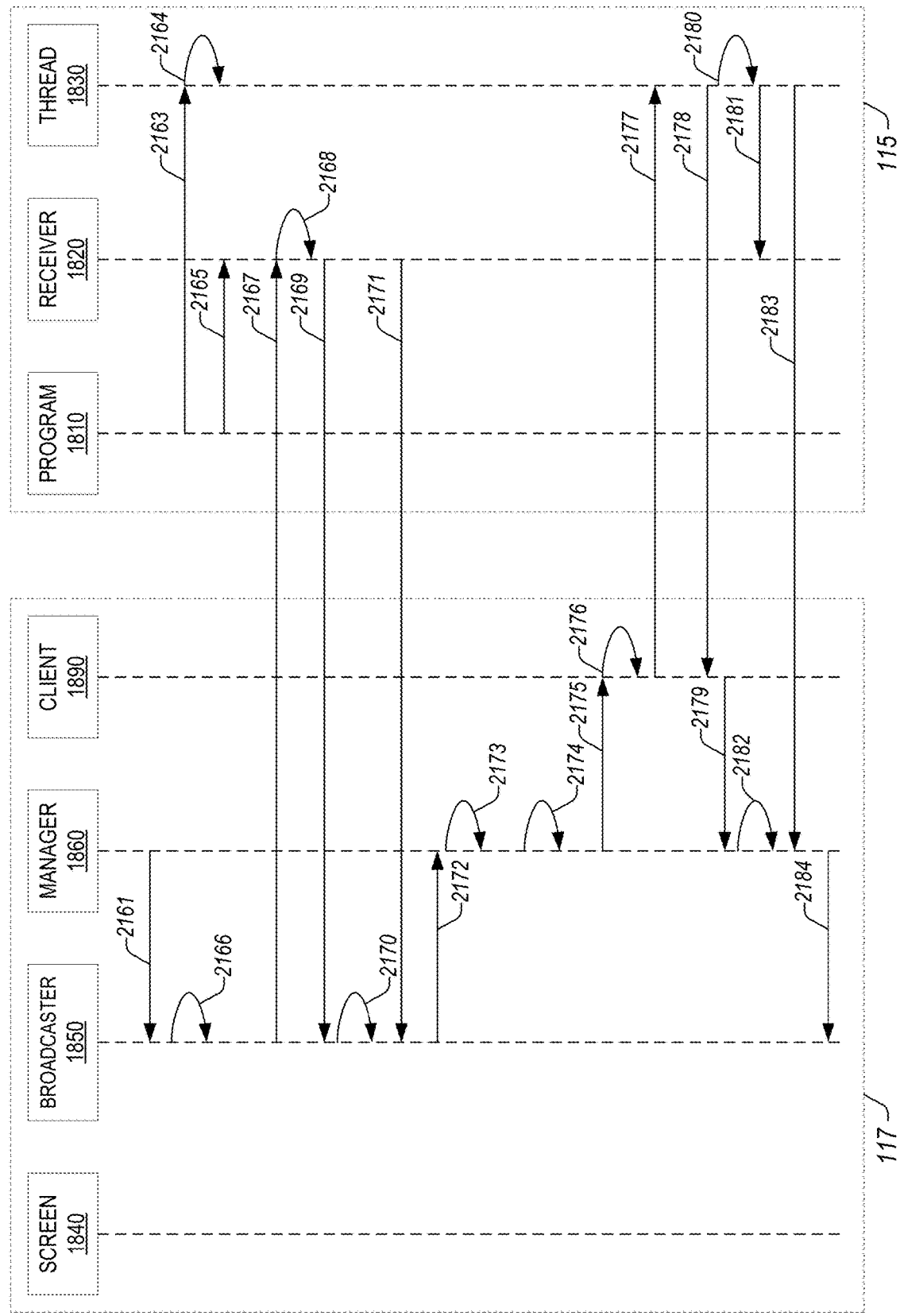
FIG. 21 illustrates a sequence diagram depicting a chronological order of events executed by the base unit and the user interface unit when the user interface unit is connected to the base unit over a wired connection source and is the same user interface unit reconnecting with the base unit.

FIG. 21 illustrates a sequence diagram depicting a chronological order of events executed by the base unit 115 and the user interface unit 117 when the user interface unit 117 is connected to the base unit 115 over a wired connection source and is the same user interface unit reconnecting with the base unit 115. As illustrated in FIG. 21, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the manager 1860 may instruct the broadcaster 1850 to listen and broadcast a pairing ID at 2161. Similarly, after the user interface unit 117 is removed from a dock or tether connecting the user interface unit 117 with the base unit 115, the program 1810 may instruct the thread 1830 to start listening for a broadcast pairing ID at 2163. Receipt of the instruction may cause the thread 1830 to create a listener (e.g., a TCP listener) at 2164. The program 1810 may also instruct the receiver 1820 to start listening for a broadcast pairing ID at 2165.

The broadcaster 1850 may attempt to connect to the wireless hotspot at 2166. After some time, the broadcaster 1850 may also transmit the pairing ID at 2167. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection.

After receiving the pairing ID, the receiver 1820 can determine whether to use a wired or wireless connection source at 2168 as described above. Here, the receiver 1820 selected the wired connection source. Once this is determined, the receiver 1820 can transmit a response over the wired connection source acknowledging that the pairing ID was received and/or indicating that the base unit 115 is attempting a connection at 2169.

The broadcaster 1850 can then begin to listen for the pairing information at 2170. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2171. At 2172, the broadcaster 1850 notifies the manager 1860 that a connection is detected, which causes the manager 1860 to start a connection detected function at 2173. The manager 1860 at 2174 then connects and initializes the send and/or receive message handlers.

The manager 1860 then notifies the client 1890 that the message handlers are initialized at 2175 and the client 1890 determines whether to use a wired or wireless connection source at 2176. Here, the client 1890 uses the wired connection source. After the determination is made, the client 1890 transmits a connection request over the wired connection source to the thread 1830 at 2177. At 2178, the thread 1830 sends a message to the client 1890 accepting the connection. The client 1890 then notifies the manager 1860 of the connection acceptance at 2179. Before or after message 2179, the thread 1830 initializes send and/or receive message handlers to handle the connection at 2180 and instructs the receiver 1820 to stop listening for pairing IDs at 2181. After receiving the connection acceptance at 2179, the manager 1860 starts listening for the acknowledgment message at 2182. At 2183, the thread 1830 transmits the acknowledgment message to the manager 1860. This may cause the manager 1860 to transmit an instruction to the broadcaster 1850 to stop broadcasting the pairing ID at 2184.

Figure 22:
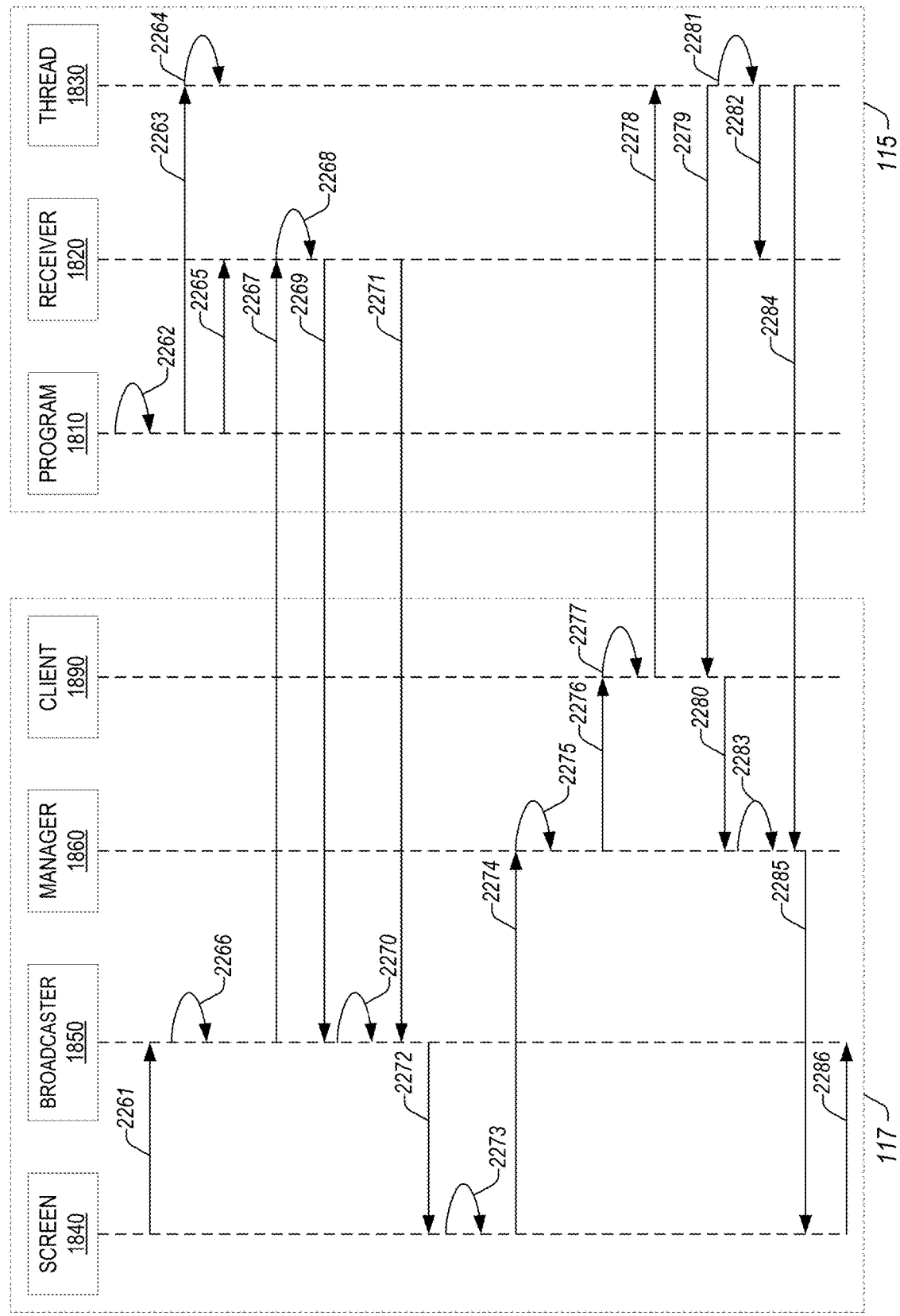
FIG. 22 illustrates a sequence diagram depicting a chronological order of events executed by the base unit and the user interface unit when the user interface unit is connected to the base unit over a wireless connection source and attempts to pair with the base unit for the first time.

FIG. 22 illustrates a sequence diagram depicting a chronological order of events executed by the base unit 115 and the user interface unit 117 when the user interface unit 117 is connected to the base unit 115 over a wireless connection source and attempts to pair with the base unit 115 for the first time. As illustrated in FIG. 22, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

At startup, such as when the user interface unit 117 is turned on, the screen 1840 may display a pairing screen. The screen 1840 may then instruct the broadcaster 1850 to listen and broadcast a pairing ID at 2261. Similarly, at startup, such as when the base unit 115 is turned on, the program 1810 may launch a wireless host so as to create a wireless hotspot at 2262. The program 1810 may then instruct the thread 1830 to start listening for a broadcast pairing ID at 2263. Receipt of the instruction may cause the thread 1830 to create a listener (e.g., a TCP listener) at 2264. The program 1810 may also instruct the receiver 1820 to start listening for a broadcast pairing ID at 2265.

The broadcaster 1850 may attempt to connect to the wireless hotspot at 2266. After some time, the broadcaster 1850 may also transmit the pairing ID at 2267. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection if the pairing ID of the user interface unit 117 matches the pairing ID of the base unit 115. Otherwise, if the pairing IDs do not match, then the receiver 1820 may not send an acknowledgment.

After receiving the pairing ID, the receiver 1820 can determine whether to use a wired or wireless connection source at 2268 as described above. Here, the receiver 1820 selected the wireless connection source. Once this is determined, the receiver 1820 can check to ensure that the pairing IDs match. If the pairing IDs match, then the receiver 1820 can transmit a response over the wireless connection source acknowledging that the pairing ID was received and/or indicating that the base unit 115 is attempting a connection at 2269. If the pairing IDs do not match, then the receiver 1820 does not transmit a response and the remaining messages described below are not transmitted. Rather, the broadcaster 1850 resumes broadcasting the pairing ID.

The broadcaster 1850 can then begin to listen for the pairing information at 2270. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2271. At 2272, the broadcaster 1850 notifies the screen 1840 that a connection is detected, which causes the screen 1840 to start a connection detected function that causes the screen 1840 to display the pairing information at 2273. In addition, the screen 1840 may display the confirm button. The broadcaster 1850 may continue to broadcast the pairing ID until the confirm button is selected to ensure that the base unit 115 is still available for a connection. Once the confirm button is selected, then the screen 1840 notifies the manager 1860 at 2274 and the manager 1860 initializes the send and/or receive message handlers at 2275.

The manager 1860 then notifies the client 1890 that the message handlers are initialized at 2276 and the client 1890 determines whether to use a wired or wireless connection source at 2277. Here, the client 1890 uses the wireless connection source. After the determination is made, the client 1890 transmits a connection request over the wireless connection source to the thread 1830 at 2278. At 2279, the thread 1830 sends a message to the client 1890 accepting the connection. The client 1890 then notifies the manager 1860 of the connection acceptance at 2280. Before or after message 1880, the thread 1830 initializes send and/or receive message handlers to handle the connection at 2281 and instructs the receiver 1820 to stop listening for pairing IDs at 2282. After receiving the connection acceptance at 2280, the manager 1860 starts listening for the acknowledgment message at 2283. At 2284, the thread 1830 transmits the acknowledgment message to the manager 1860. This may cause the manager 1860 to transmit a notification to the screen 1840 that the connection is successful at 2285. The screen 1840 may then instruct the broadcaster 1850 to stop broadcasting the pairing ID at 2286.

Figure 23:
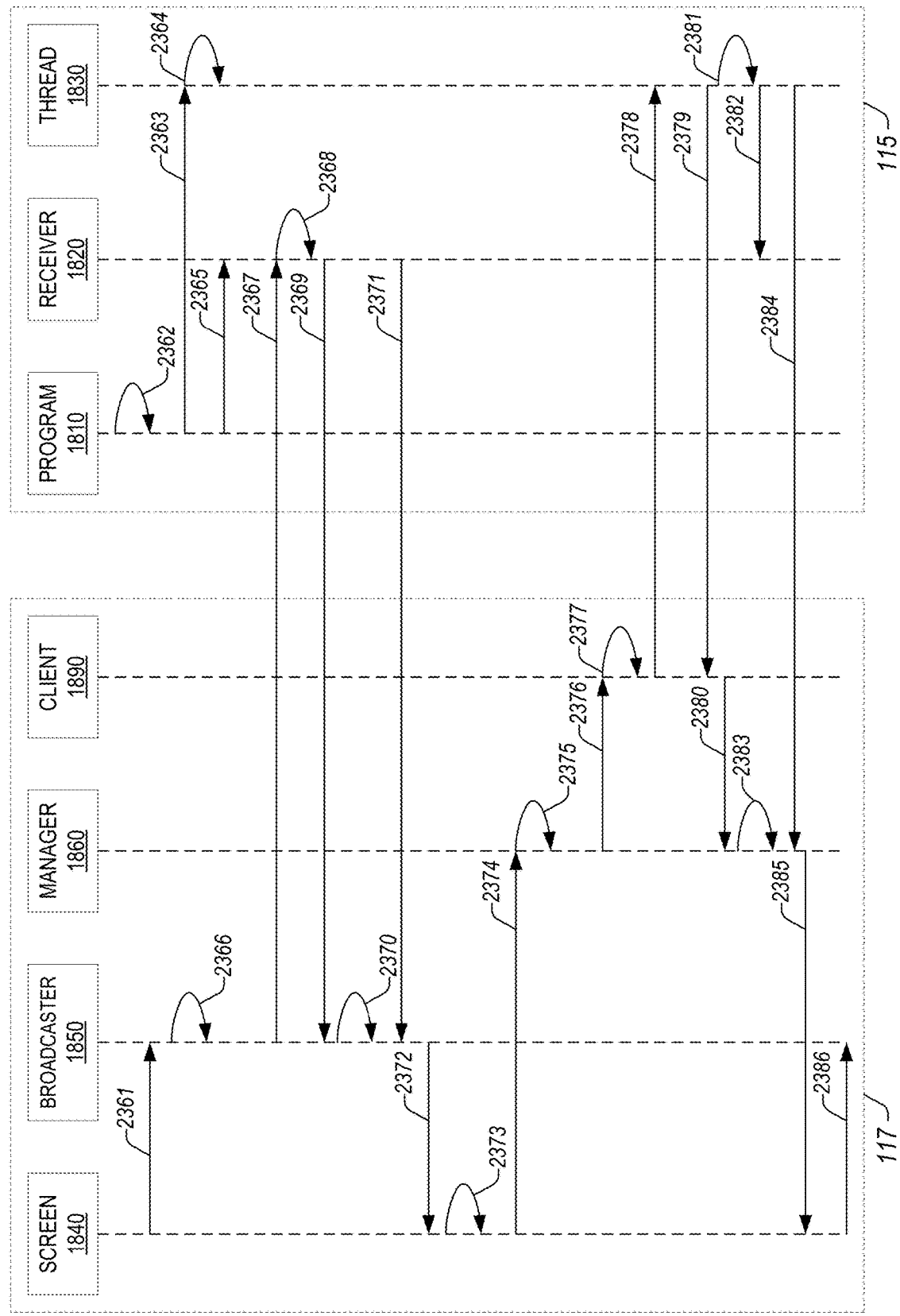
FIG. 23 illustrates a sequence diagram depicting a chronological order of events executed by the base unit and the user interface unit when the user interface unit is connected to the base unit over a wireless connection source and attempts to re-pair with the base unit.

FIG. 23 illustrates a sequence diagram depicting a chronological order of events executed by the base unit 115 and the user interface unit 117 when the user interface unit 117 is connected to the base unit 115 over a wireless connection source and attempts to re-pair with the base unit 115. As illustrated in FIG. 23, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the screen 1840 may instruct the broadcaster 1850 (e.g., on any screen) to listen and broadcast a pairing ID at 2361. Similarly, after the user interface unit 117 is removed from a dock or tether connecting the user interface unit 117 with the base unit 115, the program 1810 may launch a wireless host so as to create a wireless hotspot at 2362 and the program 1810 may instruct the thread 1830 to start listening for a broadcast pairing ID at 2363. Receipt of the instruction may cause the thread 1830 to create a listener (e.g., a TCP listener) at 2364. The program 1810 may also instruct the receiver 1820 to start listening for a broadcast pairing ID at 2365.

The broadcaster 1850 may attempt to connect to the wireless hotspot at 2366. After some time, the broadcaster 1850 may also transmit the pairing ID at 2367. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection if the pairing ID of the user interface unit 117 matches the pairing ID of the base unit 115. Otherwise, if the pairing IDs do not match, then the receiver 1820 may not send an acknowledgment.

After receiving the pairing ID, the receiver 1820 can determine whether to use a wired or wireless connection source at 2368 as described above. Here, the receiver 1820 selected the wireless connection source. Once this is determined, the receiver 1820 can check to ensure that the pairing IDs match. If the pairing IDs match, then the receiver 1820 can transmit a response over the wireless connection source acknowledging that the pairing ID was received and/or indicating that the base unit 115 is attempting a connection at 2369. If the pairing IDs do not match, then the receiver 1820 does not transmit a response and the remaining messages described below are not transmitted. Rather, the broadcaster 1850 resumes broadcasting the pairing ID.

The broadcaster 1850 can then begin to listen for the pairing information at 2370. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2371. At 2372, the broadcaster 1850 notifies the screen 1840 that a connection is detected, which causes the screen 1840 to start a connection detected function at 2373. The screen 1840 then notifies the manager 1860 at 2374 to connect and the manager 1860 initializes the send and/or receive message handlers at 2375.

The manager 1860 then notifies the client 1890 that the message handlers are initialized at 2376 and the client 1890 determines whether to use a wired or wireless connection source at 2377. Here, the client 1890 uses the wireless connection source. After the determination is made, the client 1890 transmits a connection request over the wireless connection source to the thread 1830 at 2378. At 2379, the thread 1830 sends a message to the client 1890 accepting the connection. The client 1890 then notifies the manager 1860 of the connection acceptance at 2380. Before or after message 2380, the thread 1830 initializes send and/or receive message handlers to handle the connection at 2381 and instructs the receiver 1820 to stop listening for pairing IDs at 2382. After receiving the connection acceptance at 2380, the manager 1860 starts listening for the acknowledgment message at 2383. At 2384, the thread 1830 transmits the acknowledgment message to the manager 1860. This may cause the manager 1860 to transmit a notification to the screen 1840 that the connection is successful at 2385. The screen 1840 may then instruct the broadcaster 1850 to stop broadcasting the pairing ID at 2386.

Figure 24:
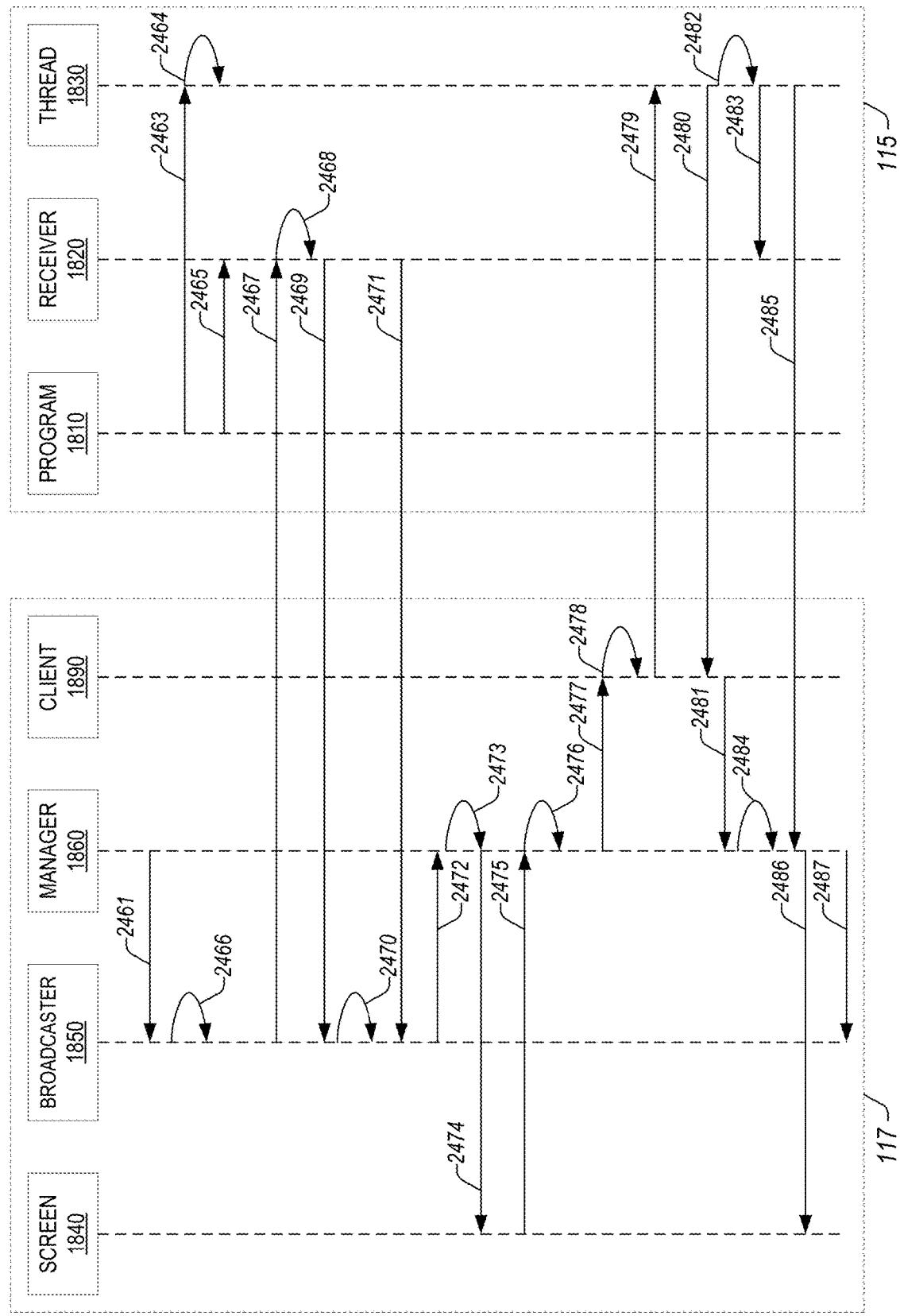
FIG. 24 illustrates a sequence diagram depicting a chronological order of events executed by the base unit and the user interface unit when the user interface unit is connected to the base unit over a wireless connection source and is a new user interface unit reconnecting with the base unit.

FIG. 24 illustrates a sequence diagram depicting a chronological order of events executed by the base unit 115 and the user interface unit 117 when the user interface unit 117 is connected to the base unit 115 over a wireless connection source and is a new user interface unit reconnecting with the base unit 115. As illustrated in FIG. 24, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the manager 1860 may instruct the broadcaster 1850 to listen and broadcast a pairing ID at 2461. Similarly, after the user interface unit 117 is removed from a dock or tether connecting the user interface unit 117 with the base unit 115, the program 1810 may instruct the thread 1830 to start listening for a broadcast pairing ID at 2463. Receipt of the instruction may cause the thread 1830 to create a listener (e.g., a TCP listener) at 2464. The program 1810 may also instruct the receiver 1820 to start listening for a broadcast pairing ID at 2465.

The broadcaster 1850 may attempt to connect to the wireless hotspot at 2466. After some time, the broadcaster 1850 may also transmit the pairing ID at 2467. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection if the pairing ID of the user interface unit 117 matches the pairing ID of the base unit 115. Otherwise, if the pairing IDs do not match, then the receiver 1820 may not send an acknowledgment.

After receiving the pairing ID, the receiver 1820 can determine whether to use a wired or wireless connection source at 2468 as described above. Here, the receiver 1820 selected the wireless connection source. Once this is determined, the receiver 1820 can check to ensure that the pairing IDs match. If the pairing IDs match, then the receiver 1820 can transmit a response over the wireless connection source acknowledging that the pairing ID was received and/or indicating that the base unit 115 is attempting a connection at 2469. If the pairing IDs do not match, then the receiver 1820 does not transmit a response and the remaining messages described below are not transmitted. Rather, the broadcaster 1850 resumes broadcasting the pairing ID.

The broadcaster 1850 can then begin to listen for the pairing information at 2470. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2471. At 2472, the broadcaster 1850 notifies the manager 1860 that a connection is detected, which causes the manager 1860 to start a connection detected function at 2473. The manager 1860 then instructs the screen 1840 to show the pairing screen at 2474, where the pairing screen includes the confirm button. Once the confirm button is selected, the screen 1840 notifies the manager 1860 accordingly at 2475. Selection of the confirm button causes the manager 1860 at 2476 to connect and initialize the send and/or receive message handlers.

The manager 1860 then notifies the client 1890 that the message handlers are initialized at 2477 and the client 1890 determines whether to use a wired or wireless connection source at 2478. Here, the client 1890 uses the wireless connection source. After the determination is made, the client 1890 transmits a connection request over the wireless connection source to the thread 1830 at 2479. At 2480, the thread 1830 sends a message to the client 1890 accepting the connection. The client 1890 then notifies the manager 1860 of the connection acceptance at 2481. Before or after message 2481, the thread 1830 initializes send and/or receive message handlers to handle the connection at 2482 and instructs the receiver 1820 to stop listening for pairing IDs at 2483. After receiving the connection acceptance at 2481, the manager 1860 starts listening for the acknowledgment message at 2484. At 2485, the thread 1830 transmits the acknowledgment message to the manager 1860. This may cause the manager 1860 to transmit an instruction to the screen 1840 to close the pairing screen at 2486 and an instruction to the broadcaster 1850 to stop broadcasting the pairing ID at 2487.

Figure 25:
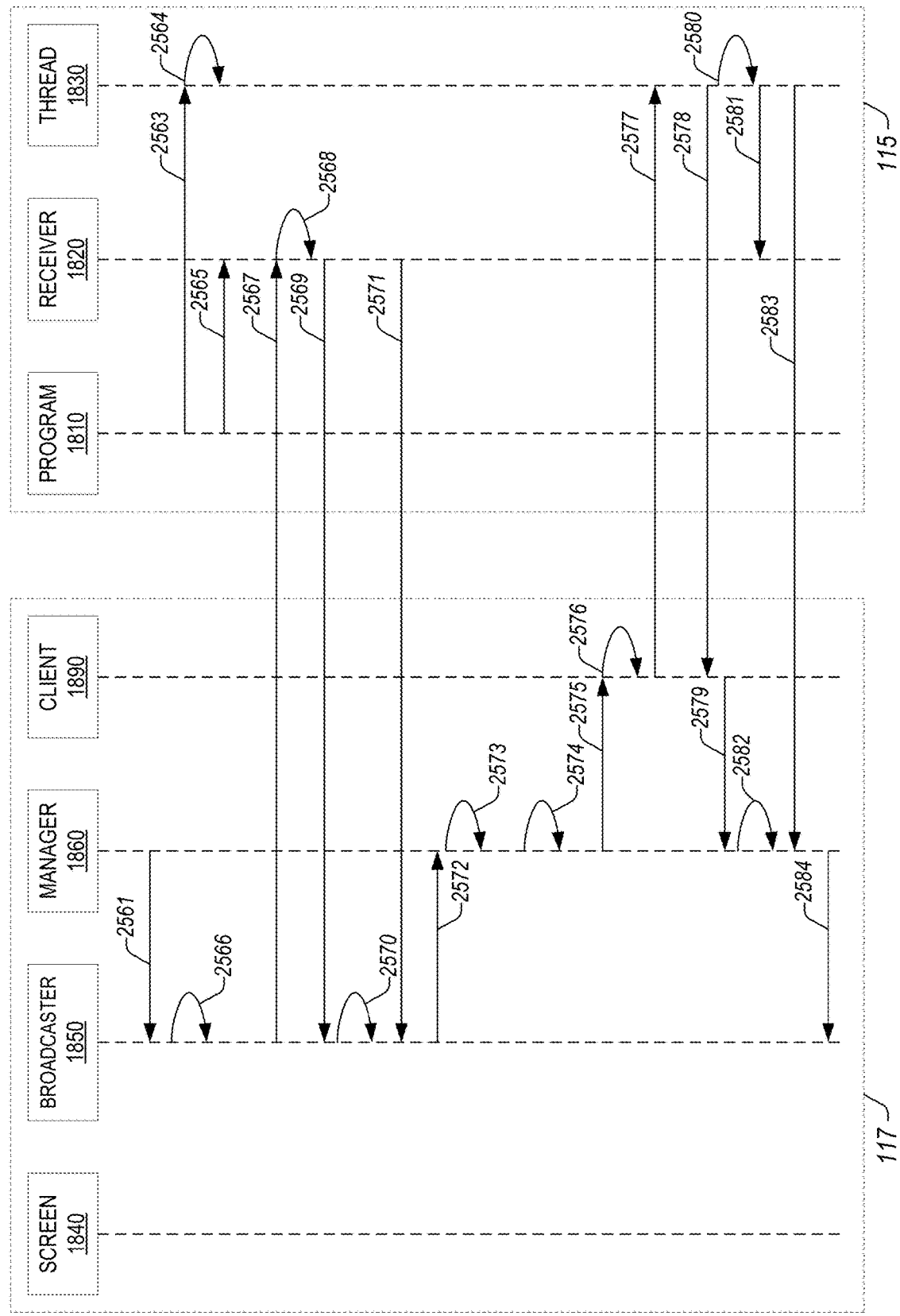
FIG. 25 illustrates a sequence diagram depicting a chronological order of events executed by the base unit and the user interface unit when the user interface unit is connected to the base unit over a wireless connection source and is the same user interface unit reconnecting with the base unit.

FIG. 25 illustrates a sequence diagram depicting a chronological order of events executed by the base unit 115 and the user interface unit 117 when the user interface unit 117 is connected to the base unit 115 over a wireless connection source and is the same user interface unit reconnecting with the base unit 115. As illustrated in FIG. 25, the base unit 115 executes a series of processes, including program 1810, receiver 1820, and thread 1830. The receiver 1820 may be the second thread described above and the thread 1830 may be the first thread described above. The user interface unit 117 can execute a series of processes, including screen 1840 (e.g., information displayed on the screen), broadcaster 1850, manager 1860, and client 1890.

After the user interface unit 117 is removed from a dock or tether connecting the user interface unit 117 with the base unit 115, the manager 1860 may instruct the broadcaster 1850 to listen and broadcast a pairing ID at 2561. Similarly, after the user interface unit 117 is removed from a dock or tether connecting the user interface unit 117 with the base unit 115, the program 1810 may instruct the thread 1830 to start listening for a broadcast pairing ID at 2563. Receipt of the instruction may cause the thread 1830 to create a listener (e.g., a TCP listener) at 2564. The program 1810 may also instruct the receiver 1820 to start listening for a broadcast pairing ID at 2565.

The broadcaster 1850 may attempt to connect to the wireless hotspot at 2566. After some time, the broadcaster 1850 may also transmit the pairing ID at 2567. For example, the broadcaster 1850 may broadcast the pairing ID. The broadcaster 1850 may periodically transmit the pairing ID (e.g., every 3 seconds or other like time period) until pairing information is received from the base unit 115. Receipt of the pairing ID may cause the receiver 1820 to transmit a response acknowledging that the pairing ID was received and/or indicating that the base unit 115 is attempting a connection if the pairing ID of the user interface unit 117 matches the pairing ID of the base unit 115. Otherwise, if the pairing IDs do not match, then the receiver 1820 may not send an acknowledgment.

After receiving the pairing ID, the receiver 1820 can determine whether to use a wired or wireless connection source at 2568 as described above. Here, the receiver 1820 selected the wireless connection source. Once this is determined, the receiver 1820 can check to ensure that the pairing IDs match. If the pairing IDs match, then the receiver 1820 can transmit a response over the wireless connection source acknowledging that the pairing ID was received and/or indicating that the base unit 115 is attempting a connection at 2569. If the pairing IDs do not match, then the receiver 1820 does not transmit a response and the remaining messages described below are not transmitted. Rather, the broadcaster 1850 resumes broadcasting the pairing ID.

The broadcaster 1850 can then begin to listen for the pairing information at 2570. The broadcaster 1850 may listen for a timeout period (e.g., 5 seconds or other like time periods). If the pairing information is not received before the timeout period expires, then the broadcaster 1850 may again broadcast the pairing ID. Here, the receiver 1820 transmits the pairing information before the timeout period expires at 2571. At 2572, the broadcaster 1850 notifies the manager 1860 that a connection is detected, which causes the manager 1860 to start a connection detected function at 2573. The manager 1860 at 2574 then connects and initializes the send and/or receive message handlers.

The manager 1860 then notifies the client 1890 that the message handlers are initialized at 2575 and the client 1890 determines whether to use a wired or wireless connection source at 2576. Here, the client 1890 uses the wireless connection source. After the determination is made, the client 1890 transmits a connection request over the wireless connection source to the thread 1830 at 2577. At 2578, the thread 1830 sends a message to the client 1890 accepting the connection. The client 1890 then notifies the manager 1860 of the connection acceptance at 2579. Before or after message 2579, the thread 1830 initializes send and/or receive message handlers to handle the connection at 2580 and instructs the receiver 1820 to stop listening for pairing IDs at 2581. After receiving the connection acceptance at 2579, the manager 1860 starts listening for the acknowledgment message at 2582. At 2583, the thread 1830 transmits the acknowledgment message to the manager 1860. This may cause the manager 1860 to transmit an instruction to the broadcaster 1850 to stop broadcasting the pairing ID at 2584.

Terminology

Many variations on the patient monitoring systems and methods described above are possible. For example, the user interface unit can be implemented using different design aesthetics as well as different physical elements for docking with a compatible base unit. In addition, the base unit can be configured to receive information and send it directly to the user interface unit for further processing prior to display (e.g., determining a measured hemodynamic parameter from patient sensor electrical information).

Each of the processes, methods, and algorithms described in the preceding sections may be embodied in, and fully or partially automated by, code modules executed by one or more specialized or dedicated computers, computer processors, or machines configured to execute specialized computer instructions. The code modules may be implemented using a combination of hardware (e.g., programmable logic circuits, application specific integrated circuits, microprocessors, etc.) and software stored on any type of non-transitory computer-readable medium or tangible computer storage device, such as hard drives, solid state memory, optical disc, and/or the like. The systems and modules may also be transmitted as generated data signals (e.g., as part of a carrier wave or other analog or digital propagated signal) on a variety of computer-readable transmission mediums, including wireless-based and wired/cable-based mediums, and may take a variety of forms (e.g., as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described tasks or events may be performed in an order other than that specifically disclosed, or multiple may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

Conditional language used herein, such as, among others, "can," "could," "might," "may," "e.g.," and the like, is not generally intended to imply that features, elements and/or steps are required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present. The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (e.g., measurement value) is close to a targeted value, where close can mean, for example, the result is within 80% of the value, within 90% of the value, within 95% of the value, or within 99% of the value.

While certain example embodiments have been described, these embodiments have been presented by way of example only, and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the inventions disclosed herein.

What is claimed is:

1. A patient monitor configured to receive electrical signals from an invasive patient sensor and a minimally invasive patient sensor, the patient monitor comprising:
    a base unit comprising:
        a housing forming a docking base and a front plate, the docking base including a base unit connector;
        a plurality of sensor input connectors on an exterior portion of the housing, at least one sensor input connector configured to receive electrical signals from the invasive patient sensor and at least one sensor input connector configured to receive electrical signals from the minimally invasive patient sensor;
        a processor;
        a wireless communication system comprising an antenna and a transceiver enclosed within the housing; and
        a latch attached to the housing; and
    a user interface unit comprising:
        a housing with a bottom portion and a rear portion;
        a display on a front portion of the user interface unit, the display configured to display hemodynamic parameters determined by the base unit based on the electrical signals received from the invasive patient sensor;
        a wireless communication system enclosed within the housing; and
        a user interface connector on the bottom portion of the housing, the user interface connector configured to mate with the base unit connector,
    wherein, in a docked configuration, the user interface connector is configured to directly couple to the base unit connector and the bottom portion of the housing of the user interface unit is configured to contact the docking base of the base unit and at least a portion of the rear portion of the housing of the user interface unit is configured to contact the front plate of the housing of the base unit, and the latch is configured to secure the user interface unit to the base unit,
    wherein, in a tethered configuration, the user interface connector is electrically coupled to the base unit connector using a cable, the cable conducting electrical power between the base unit and the user interface unit,
    wherein, in a detached configuration, the wireless communication system of the user interface unit is configured to wirelessly communicate with the wireless communication system of the base unit,
    wherein the processor is configured to switch between determining a hemodynamic parameter of a patient based on the electrical signals received from the invasive patient sensor and determining the hemodynamic parameter of the patient based on the electrical signals received from the minimally invasive patient sensor, and
    wherein the processor is configured to cause display of the hemodynamic parameter derived from the invasive patient sensor after the switch from the invasive patient sensor to the minimally invasive patient sensor until the hemodynamic parameters derived from the minimally invasive patient sensor are calibrated.

2. The patient monitor of claim 1, wherein the minimally invasive patient sensor comprises at least one pressure sensor configured to be in fluid communication with the patient's blood vessel through a fluid-receiving region in the pressure sensor and configured to be in electrical communication with the base unit, the pressure sensor being configured to sense a pressure wave in the patient's vasculature and being configured to transmit at least one electrical signal to the base unit that indicates a hemodynamic parameter of the patient.

3. The patient monitor of claim 1, wherein the processor is configured to determine the hemodynamic parameter of the patient based on the electrical signals received from the invasive patient sensor during a first time period and to determine the hemodynamic parameter of the patient based on the electrical signals received from the minimally invasive patient sensor during a second time period after the first time period, wherein the hemodynamic parameter based on the electrical signals received from the minimally invasive patient sensor is calibrated using the electrical signals received from the invasive patient sensor.

4. The patient monitor of claim 1, wherein the docking base is sloped so that liquid flows off of the docking base when the user interface unit is docked on the base unit.

5. The patient monitor of claim 1, further comprising a plurality of analog signal input connectors configured to receive an analog input signal from an external patient monitor system.

6. The patient monitor of claim 5, wherein the processor is configured to automatically convert received signals to a physiological parameter based on a maximum expected value of the physiological parameter and a received maximum analog signal from the external patient monitor system.

7. The patient monitor of claim 6, wherein the user interface unit receives an indication of the maximum expected value of the physiological parameter through an interaction of a user with the display.

8. The patient monitor of claim 1, wherein the base unit further comprises a conducting portion configured to act as a ground plane for the antenna of the wireless communication system so that a resulting radiation pattern of the antenna preferentially transmits electromagnetic energy in a forward direction relative to the base unit.

9. The patient monitor of claim 1, wherein the docking base and base unit connector are configured so that the user interface unit cannot be docked on the base unit with the display portion adjacent to the front plate.

10. The patient monitor of claim 1, wherein the user interface unit and the base unit are configured such that, in the tethered configuration, the user interface unit cannot be seated in the docking base so that the latch secures the user interface unit in place on the base unit.

* * * * *